(12) United States Patent
Frysz et al.

(10) Patent No.: US 11,633,612 B2
(45) Date of Patent: *Apr. 25, 2023

(54) ECA OXIDE-RESISTANT CONNECTION TO A HERMETIC SEAL FERRULE FOR AN ACTIVE IMPLANTABLE MEDICAL DEVICE

(71) Applicant: Greatbatch Ltd., Clarence, NY (US)

(72) Inventors: Christine A. Frysz, Orchard Park, NY (US); Robert A. Stevenson, Canyon County, CA (US); Jason Woods, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 202 days.

This patent is subject to a terminal disclaimer.

(21) Appl. No.: 17/181,542

(22) Filed: Feb. 22, 2021

(65) Prior Publication Data
US 2021/0283404 A1 Sep. 16, 2021

Related U.S. Application Data

(63) Continuation-in-part of application No. 17/077,337, filed on Oct. 22, 2020, now Pat. No. 11,185,705, (Continued)

(51) Int. Cl.
*A61N 1/375* (2006.01)
*H01G 4/224* (2006.01)
(Continued)

(52) U.S. Cl.
CPC ......... *A61N 1/3754* (2013.01); *A61N 1/3758* (2013.01); *A61N 1/37512* (2017.08);
(Continued)

(58) Field of Classification Search
CPC ............. A61N 1/3754; A61N 1/37512; A61N 1/3758; A61N 1/3956; A61N 1/3718;
(Continued)

(56) References Cited

U.S. PATENT DOCUMENTS 4,424,551 A   1/1984   Stevenson et al.
5,333,095 A   7/1994   Stevenson et al.
(Continued)

FOREIGN PATENT DOCUMENTS

EP   3081258 A1   10/2016
EP   3569284 A1   11/2019

OTHER PUBLICATIONS

Camm, "Editor-in-Chief", European Pacing, Arrhythmias and Cardiac Electrophysiology, Sep. 1, 2009, 1238-1239.
(Continued)

*Primary Examiner* — Mark W. Bockelman
(74) *Attorney, Agent, or Firm* — Michael F. Scalise

(57) ABSTRACT

A hermetically sealed feedthrough assembly for an active implantable medical device having an oxide-resistant electrical attachment for connection to an EMI filter, an EMI filter circuit board, an AIMD circuit board, or AIMD electronics. The oxide-resistant electrical attachment, including an oxide-resistant sputter layer 165 is disposed on the device side surface of the hermetic seal ferrule over which an ECA stripe is provided. The ECA stripe may comprise one of a thermal-setting electrically conductive adhesive, an electrically conductive polymer, an electrically conductive epoxy, an electrically conductive silicone, an electrically conductive polyimides, or an electrically conductive polyimide, such as those manufactured by Ablestick Corporation. The oxide-free electrical attachment between the ECA stripe and the filter or AIMD circuits may comprise one of gold, platinum, palladium, silver, iridium, rhenium, rhodium, tantalum, tungsten, niobium, zirconium, vanadium, and combinations or alloys thereof.

20 Claims, 44 Drawing Sheets

Related U.S. Application Data which is a continuation of application No. 16/854,138, filed on Apr. 21, 2020, now Pat. No. 10,828,498.

(60) Provisional application No. 63/021,858, filed on May 8, 2020, provisional application No. 62/979,600, filed on Feb. 21, 2020.

(51) Int. Cl.
| | |
|---|---|
| *H01G 4/35* | (2006.01) |
| *H01B 17/62* | (2006.01) |
| *H01G 2/12* | (2006.01) |
| *H01G 4/228* | (2006.01) |
| *H01G 13/00* | (2013.01) |
| *H01B 19/04* | (2006.01) |
| *H01G 2/10* | (2006.01) |

(52) U.S. Cl.
CPC ............. *H01B 17/62* (2013.01); *H01B 19/04* (2013.01); *H01G 2/103* (2013.01); *H01G 2/12* (2013.01); *H01G 4/224* (2013.01); *H01G 4/228* (2013.01); *H01G 4/35* (2013.01); *H01G 13/003* (2013.01)

(58) Field of Classification Search
CPC .... A61N 1/36053; H01B 17/62; H01B 19/04; H01G 2/103; H01G 2/12; H01G 4/224; H01G 4/228; H01G 4/35; H01G 13/003
See application file for complete search history.

(56) References Cited

U.S. PATENT DOCUMENTS

| | | | |
|---|---|---|---|
| 5,896,267 | A | 4/1999 | Hittman et al. |
| 5,905,627 | A | 5/1999 | Brendel et al. |
| 5,959,829 | A | 9/1999 | Stevenson et al. |
| 5,973,906 | A | 10/1999 | Stevenson et al. |
| 6,275,369 | B1 | 8/2001 | Stevenson et al. |
| 6,529,103 | B1 | 3/2003 | Brendel et al. |
| 6,765,779 | B2 | 7/2004 | Stevenson et al. |
| 6,888,715 | B2 | 5/2005 | Stevenson et al. |
| 7,038,900 | B2 | 5/2006 | Stevenson et al. |
| 8,352,033 | B2 | 1/2013 | Kroll |
| 8,457,760 | B2 | 6/2013 | Dabney et al. |
| 8,700,156 | B2 | 4/2014 | Kroll |
| 8,812,103 | B2 | 8/2014 | Kroll et al. |
| 8,825,158 | B2 | 9/2014 | Swerdlow |
| 9,272,150 | B2 | 3/2016 | Kroll et al. |
| 9,427,577 | B2 | 8/2016 | Kroll et al. |
| 9,486,624 | B2 | 11/2016 | Swerdlow |
| 9,492,659 | B2 | 11/2016 | Brendel et al. |
| 9,636,500 | B2 | 5/2017 | Swerdlow et al. |
| 9,675,799 | B2 | 6/2017 | Kroll et al. |
| 9,757,558 | B2 | 9/2017 | Stevenson et al. |
| 9,814,876 | B2 | 11/2017 | Swerdlow |
| 9,821,156 | B2 | 11/2017 | Kroll et al. |
| 9,827,416 | B2 | 11/2017 | Swerdlow |
| 2004/0235549 | A1 | 11/2004 | Struble et al. |
| 2007/0123949 | A1 | 5/2007 | Dabney et al. |
| 2009/0163980 | A1 | 6/2009 | Stevenson |
| 2009/0322632 | A1 | 12/2009 | Milosevic |
| 2010/0191236 | A1 | 7/2010 | Johnson et al. |
| 2010/0208397 | A1 | 8/2010 | Johnson et al. |
| 2014/0155947 | A1 | 6/2014 | Kroll et al. |
| 2014/0168917 | A1 | 6/2014 | Marzano |
| 2015/0217111 | A1 | 8/2015 | Stevenson et al. |
| 2016/0301369 | A1 | 10/2016 | Heaney |

OTHER PUBLICATIONS

Extendedepsearch, Extended European Search Report, Application No. 19154697.7, dated Jun. 4, 2019.
"Extended European Search Report dated Dec. 15, 2020, Application No. 20180915.9".

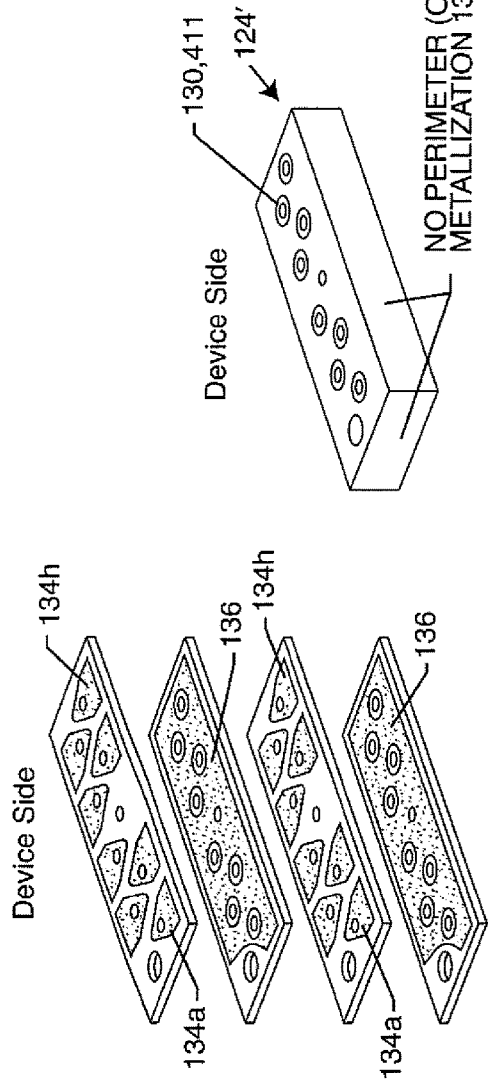
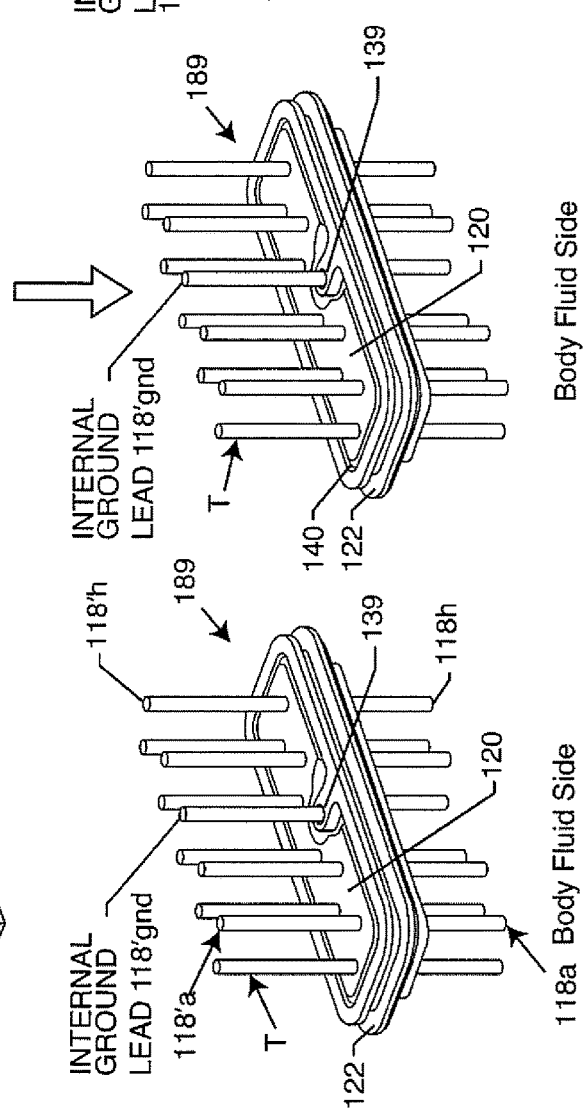
FIG. 13A PRIOR ART
FIG. 13B PRIOR ART
FIG. 13C PRIOR ART

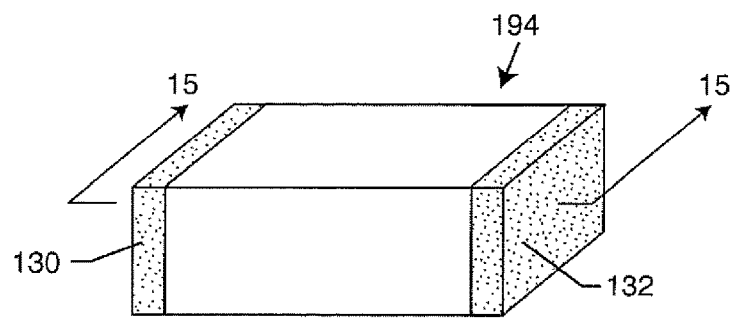
FIG. 14
PRIOR ART
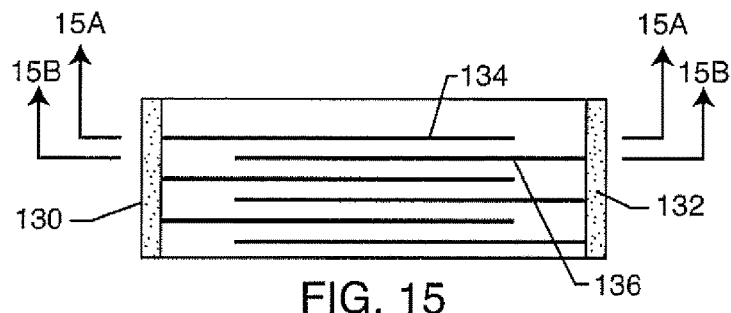
FIG. 15
PRIOR ART
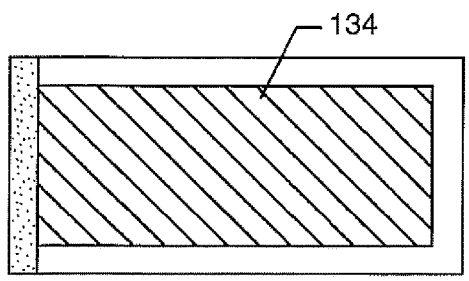 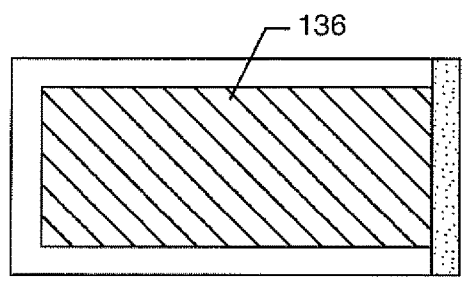
FIG. 15A    FIG. 15B
PRIOR ART      PRIOR ART ESR = resistive losses (R) plus dielctric losses (DL)

$$X_C = \frac{1}{j\omega C}$$

$$\text{Impedance, } Z = \sqrt{(ESR)^2 + \left(\omega L - \frac{1}{j\omega C}\right)^2}$$

FLAT-THRU

X2Y

X2Y

X2Y

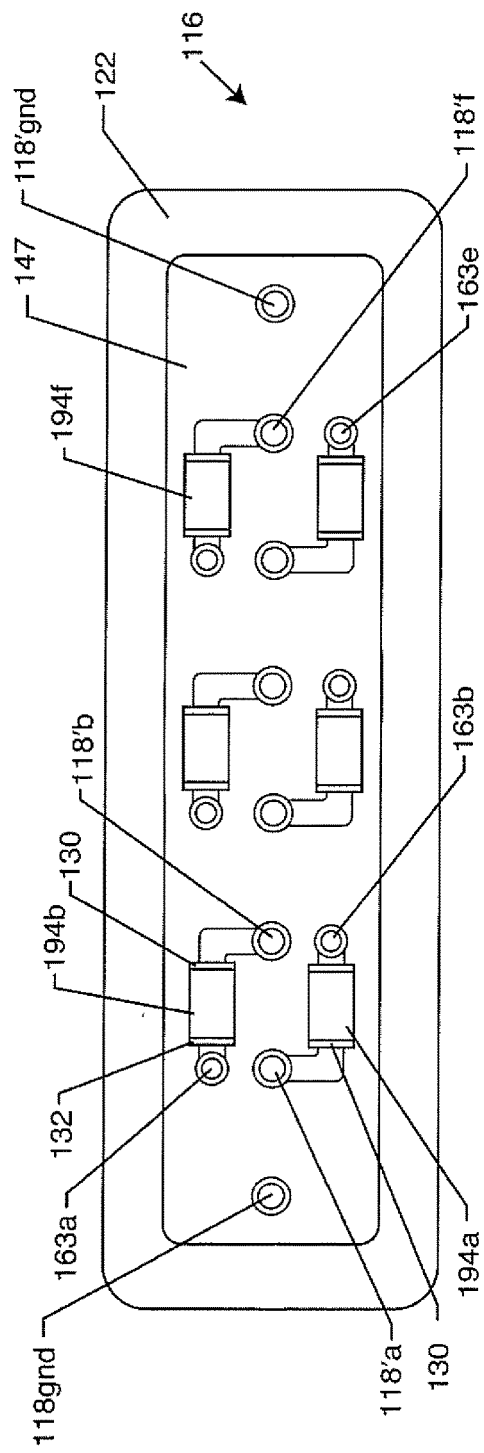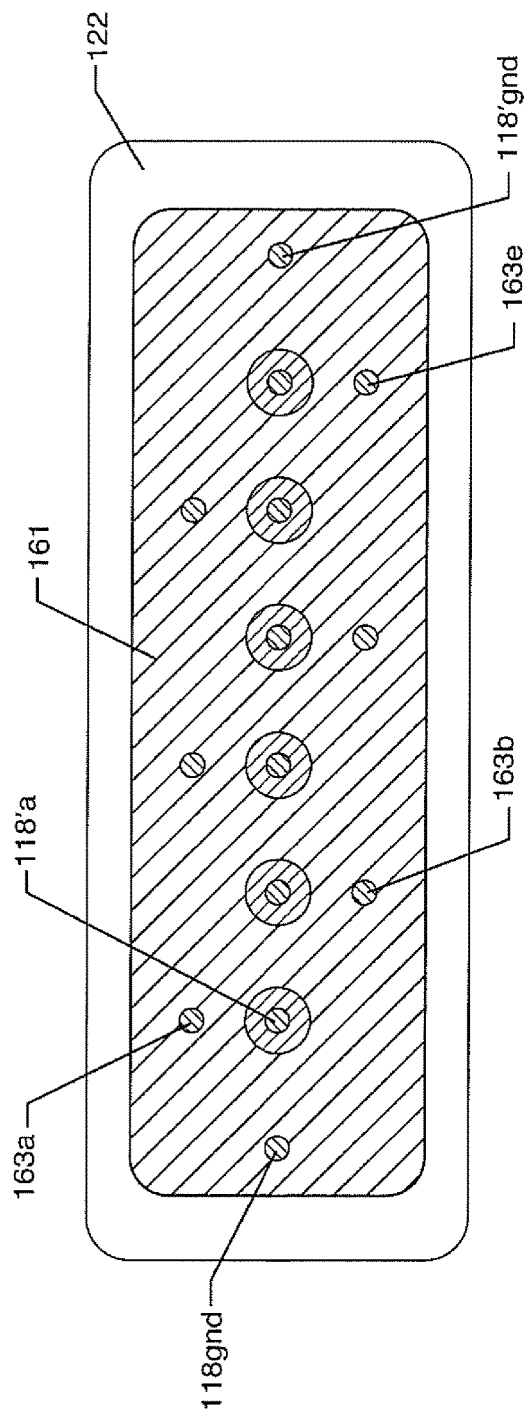
FIG. 23A
FIG. 23B (POOR PRACTICE)

BODY FLUID SIDE

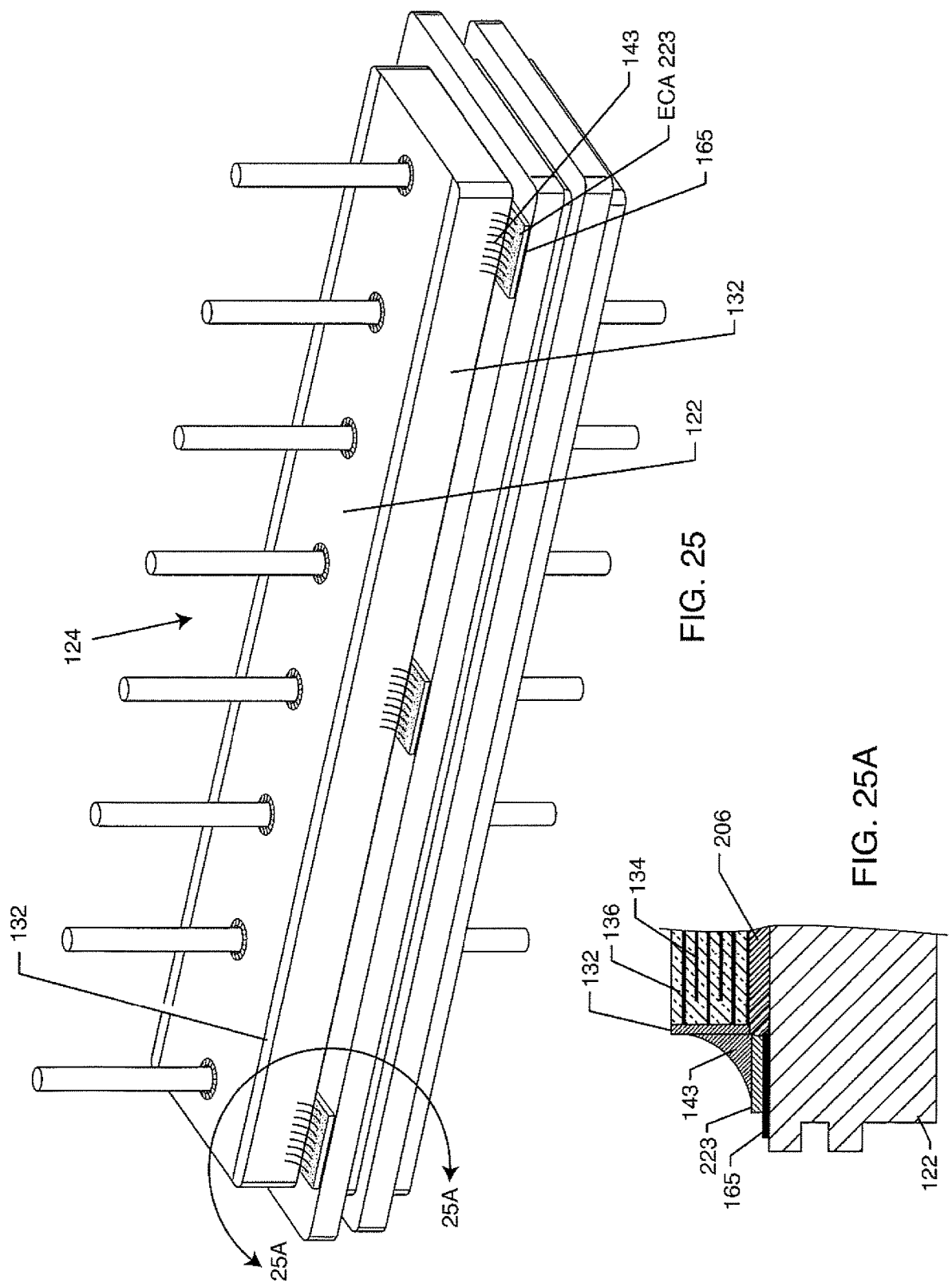

BODY FLUID SIDE

X2Y
PRIOR ART

| MLCC EMI FILTER CIRCUIT BOARDS AND FEEDTHROUGH FILTER CAPACITORS INCLUDING LOW IMPEDANCE LOW RESISTANCE OXIDE-FREE ELECTRICAL CONNECTIONS TO GROUND AND TO THE FERRULE | | | CIED FILTER CAPACITORS MADE WITH DIELECTRICS k<1000 & k<200 | HERMETIC SEAL CO-SINTERED PASTE-FILLED VIAS |
|---|---|---|---|---|
| 10,912,945 | 9,295,828 | 8,761,895 | 8,301,243 | 7,310,216 | 10,596,369 | 10,561,837 |
| 10,874,866 | 9,251,960 | 8,751,013 | 8,272,466 | 7,199,995 | 10,561,837 | 10,559,409 |
| 10,857,369 | 9,248,283 | 8,712,544 | 8,244,370 | 7,113,387 | 10,559,409 | 10,500,402 |
| 10,828,498 | 9,119,968 | 8,670,841 | 8,195,295 | 7,038,900 | 10,272,253 | 10,420,949 |
| 10,625,084 | 9,071,221 | 8,660,645 | 8,180,448 | 7,035,076 | 10,249,415 | 10,272,253 |
| 10,589,107 | 9,042,999 | 8,659,870 | 8,160,705 | 6,999,818 | 10,092,749 | 10,272,252 |
| 10,449,375 | 9,037,258 | 8,649,857 | 8,145,324 | 6,985,347 | 9,764,129 | 10,249,415 |
| 10,350,421 | 9,031,670 | 8,577,453 | 8,116,862 | 6,888,715 | 9,757,558 | 10,046,166 |
| 10,249,415 | 9,008,799 | 8,509,913 | 8,095,224 | 6,882,248 | 9,014,808 | 9,889,306 |
| 10,124,164 | 9,002,471 | 8,483,840 | 7,966,075 | 6,765,780 | 8,855,768 | 9,511,220 |
| 10,099,051 | 8,996,126 | 8,463,375 | 7,957,806 | 6,765,779 | | 9,492,659 |
| 10,080,889 | 8,977,355 | 8,457,760 | 7,945,322 | 6,567,259 | | 9,463,329 |
| 10,016,596 | 8,918,189 | 8,447,414 | 7,917,219 | 6,566,978 | | 9,352,150 |
| 10,016,595 | 8,903,505 | 8,437,865 | 7,853,324 | 6,529,103 | | 9,233,253 |
| 9,993,650 | 8,897,887 | 8,433,410 | 7,765,005 | 6,456,481 | | 8,938,309 |
| 9,931,514 | 8,868,189 | 8,422,195 | 7,702,387 | RE46,699 | | RE47,624 |
| 9,895,534 | 8,855,785 | 8,364,283 | 7,623,335 | RE48348 | | |
| 9,427,596 | 8,855,768 | 8,321,032 | 7,535,693 | | | |
| 9,312,075 | 8,788,057 | 8,311,628 | 7,489,495 | | | |

FIG. 43

ECA OXIDE-RESISTANT CONNECTION TO A HERMETIC SEAL FERRULE FOR AN ACTIVE IMPLANTABLE MEDICAL DEVICE

CROSS REFERENCE TO RELATED APPLICATIONS

The present application claims priority to U.S. provisional application Ser. No. 62/979,600, filed on Feb. 21, 2020 and U.S. provisional application Ser. No. 63/021,858, filed on May 8, 2020.

The present application is also a continuation-in-part of U.S. application Ser. No. 17/077,337, filed on Oct. 22, 2020, now U.S. Pat. No. 11,185,705, which is a continuation of U.S. App. Ser. No. 16/854,138, filed on Apr. 21, 2020, now U.S. Pat. No. 10,828,498.

The contents of all the above applications are fully incorporated herein by these references.

FIELD OF THE INVENTION

The present invention generally relates to hermetic seal subassemblies for active implantable medical devices (AIMDs). More particularly, the present invention relates to an oxide-resistant, low impedance (low resistance) and very stable electrical connection to an ECA stripe disposed on a hermetic seal ferrule. The oxide-resistant and low resistance KA stripe provides for connection of EMI filters, EMI filter circuit boards, AIMD active electronics or circuit boards.

BACKGROUND

Most present day active implantable medical devices (AIMDs) have one or more electronic circuits enclosed in a hermetically sealed conductive housing or casing. Common prior art AIMDs, including cardiac pacemakers and implantable defibrillators, have a housing that is made of titanium. Titanium, and two of its alloys, titanium-niobium and titanium-tantalum, are biocompatible and they exhibit physical and mechanical properties superior to many other metals. For example, titanium exhibits excellent corrosion resistance because, when titanium comes in contact oxygen or water, instead of corroding, titanium produces an oxide on its surface, which gets stronger over time, which constantly enhances its resilience against corrosive agents. Few substances can breach or even damage this protective oxide film, and even if the oxide film is mechanically fractured, the oxide film almost immediately regenerates. Hence, titanium is the material of choice for applications requiring biocompatibility and biostability, such as AIMDs.

For electromagnetic compatibility (EMC) and resistance to electromagnetic interference (EMI), it is typical that AIMDs comprise one or more filters at or near leadwire ingress or egress into an AIMD housing. A hermetically sealed feedthrough or a or feedthrough subassembly is typically located at the point of ingress into the AIMD housing. This hermetically sealed feedthrough typically comprises a metallic ferrule, such as titanium, and an insulator, such as an alumina ceramic, a glass, or a glass-ceramic. One or more electrical conductors pass through the insulator in non-conductive relationship with the ferrule, which are hermetically sealed to the insulator. The insulator is also hermetically sealed to the ferrule. The AIMD EMI (or MRI) filters divert undesirable EMI signals that are coupled to an implanted lead to the AIMD housing where such signals are harmlessly dissipated as a few milliwatts of heat energy. Thus, dangerous EMI is prevented from entering into the housing of the AIMD where it may disrupt the proper operation of biological sensing circuits or therapy delivery circuits. The ferrule of the hermetically sealed feedthrough is typically laser welded into the opening of the housing or casing of the AIMD. The laser welding process generates a great deal of localized heat, which leads to thickening of the surface titanium oxides, particularly the titanium oxides on the ferrule of the hermetically sealed feedthrough. This makes electrical connection of a filter, a filter circuit board, an AIMD active filter, or an AIMD active circuit board to the ferrule very challenging. For an EMI or MRI filter to work properly, the electrical connection of the filter to the ferrule must have a very low equivalent series resistance (ESR) so that a maximum amount of EMI energy is dissipated (filtered) to the AIMD housing thereby preventing the EMI energy from entering into the inside of the AIMD housing, where the EMI energy can cause undesirable, even dangerous life-threatening, device therapy delivery issues [a particular concern for cardiac implantable electronic devices (CIEDs)]. The AIMD housing, which is thermally and electrically conductive and generally of titanium, provides both an EMI shield and a hermetic seal to the AIMD. High frequency energy, such as that from microwave ovens, is reflected and absorbed by this titanium housing or shield. In addition, EMI filters intercept undesirable signals that are coupled to or radiated onto AIMD implanted leads (which act as antennas) and divert such undesirable signals to the titanium housing, thereby preventing entry into the AIMD electronics.

Referring once again to titanium and EMI diversion, it is the excellent corrosion resistance and biocompatibility of titanium that causes concern regarding the efficacy of EMI filter electrical connections. As previously noted, titanium's excellent corrosion resistance is due to the formation of a thermodynamically stable, continuous, highly adherent, and protective surface oxide film. Since titanium metal is highly reactive and has an extremely high affinity for oxygen, this surface oxide film is formed spontaneously and instantly when a fresh titanium metal surface is exposed to air and/or moisture. In fact, a damaged titanium oxide film can generally re-heal itself instantaneously if even at least traces (that is, a few parts per million) of oxygen or water are present in the environment. Researchers have proven that within a millisecond of exposure of titanium to air, a 10 nm titanium oxide layer will be formed on the cut surface of the exposed titanium metal. This titanium oxide layer will grow to about 100 nm thick within a minute. While a titanium oxide layer on the highly reactive titanium metal surface imparts good corrosion resistance and provides high biocompatibility and biostability as noted, such a titanium oxide layer can and does undesirably impact AIMD EMI filter performance. It is further noted that, besides affecting EMI filters, the undesirable impact is even more observable at higher frequency applications, such as switching applications, coupling applications, and bypass applications.

Prior art addresses oxidation layers on metals, such as a titanium oxide layer, by cleaning the surface of a metal component, for example, a titanium ferrule or a titanium casing of an AIMD, and then disposing a stripe of a thermal-setting conductive adhesive, in other words, an electrically conductive adhesive (ECA) stripe, atop the "cleaned" metal surface. The problem with this approach is that (1) the ECA stripe must be cured at an elevated temperature of between 200° C. and 300° C.; and (2) the casing must be laser welded to hermetically seal the AIMD. During curing of the ECA stripe, which is conducted in air, the titanium oxide, which is initially cleaned from the titanium surface of the exemplary ferrule of the feedthrough, almost immediately reforms. In other words, a titanium oxide layer is now present between the ECA stripe and the cleaned titanium ferrule surface. Similarly, when the casing of the pulse generator of the AIMD is laser welded, a temperature rise to the surrounding area results. The laser weld, which is typically in close proximity of the ECA stripe, can thereby directly cause additional titanium oxide formation at the attachment point between the ECA stripe and the initially cleaned but subsequently oxidized titanium post ECA cure, as elevated temperature exposure of an ECA, such as an epoxy or a polymer, typically allows the release or outgassing of oxygen and/or oxygen-containing constituents or residues that are often present within the ECA material itself. More importantly, this additional exposure to oxygen or oxygen-containing constituents causes potentially harmful thickening of the titanium oxide layer that was previously created during the ECA curing process. Hence, during AIMD manufacturing, the equivalent series resistance (ESR) of the EMI filter can dangerously increase such that EMI filtering is significantly compromised or even fails. Such potentially unsafe ESR increases are particularly observable at frequencies above 10 MHz. More importantly, and of most concern, is that the unsafe ESR increases (in other words, EMI capacitor ohmic losses) are often masked (essentially, totally hidden/indistinguishable) at low frequencies by an EMI filter's dielectric losses. Such masking is particularly egregious to present day CIEDs, such as pacemakers and implantable cardioverter-defibrillators, which are considered/labelled MRI conditionally approved, as in an MRI environment, EMI filters divert substantial, potentially dangerous, RE current generated in implanted therapy delivery leads of an AIMD during MRI to the AIMD casing for dissipation. Hence, reliance solely on KA stripe attachment to an oxidizable metal surface, such as a titanium surface, is considered to be dangerous and of poor practice by the inventors. It is known to one skilled in the art that electrical connection of AIMD passive EMI filters to a system ground must be a very low impedance connection, which means that no significant titanium oxides are allowable on any connection surface of said system ground.

For AIMDs, there are two types of electronic components. These are passive components or active components. Passive components do not require a source of energy and include capacitors, resistors and inductors. Active components do require an energy source and include microelectronic chips, microprocessors, ASIC electronics and the like. For AIMDs, energy sources are typically either a primary or a secondary battery. However, AIMD energy sources can be coupled energy sources through either inductive or wireless charging, energy harvesting (for example, by motion of the myocardium) or even ultrasonic induced energy that is captured.

Accordingly, there is a need for a low resistance and low impedance electrical connection having an electrically conductive adhesive stripe and an oxide-resistant layer for attachment of an EMI of active implantable medical device.

SUMMARY OF THE INVENTION

The present invention resides in applying an oxide-resistant sputter layer to device side surface of the ferrule, which has been either mechanically, chemically or grit blast cleaned of all surface oxides. An ECA stripe, in accordance with the present invention, is disposed over the oxide-resistant sputter layer to provide a robust electrical attachment pad or stripe for low impedance, low resistance and very stable electrical connection to EMI filters, such as feedthrough capacitors, internally grounded feedthrough capacitors, MLCC filter circuit boards, X2Y attenuators, flat-thru capacitors, internal electronic components, or AMID active circuit boards.

BRIEF DESCRIPTION OF THE DRAWINGS

FIG. 6C is an electrical schematic diagram showing how a proper filter works to divert high frequency EMI to the cardiac implantable electronic devices (CIEDs) housing, including the family of cardiac pacemakers, implantable defibrillators, implantable loop recorders and the like;

FIG. 13A illustrates an exploded perspective view of an internally grounded prior art feedthrough capacitor;

FIG. 13B illustrates the structure of FIG. 13A where now the capacitor is formed as a monolithic structure;

FIG. 13C illustrates the structure of FIG. 13B fully assembled into a feedthrough filtered hermetic terminal;

FIG. 14 illustrates a prior art monolithic ceramic capacitor (MLCC), which is also known in the art as a multilayer ceramic capacitor;

FIG. 15 is a sectional view from the MLCC chip capacitor of FIG. 14 showing its internal electrode plates;

FIG. 15A is a top sectional view from the MLCC chip capacitor showing its left-hand active electrode plates;

FIG. 15B is a similar sectional view to FIG. 15A, except in this case, showing the right-hand connected active electrode plates;

FIG. 23A is taken from section 23A-23A from FIG. 23;

FIG. 23B is taken from section 23B-23B from FIG. 23 illustrating a circuit board and internal ground plate;

FIG. 23I is the schematic diagram for the oxide-resistant filter attachments previously described in FIG. 23 and FIGS. 23A through 23H;

FIG. 25 illustrates an inline feedthrough capacitor that is grounded to an ECA stripe and an oxide-resistant sputter layer in accordance with the present invention;

FIG. 25A is taken from section 25A-25A from FIG. 25 illustrating the oxide-free connection to the ferrule;

FIG. 43 is a table and listing of all the patents that are herein incorporated fully by reference.

DETAILED DESCRIPTION OF THE INVENTION

Figure 1:
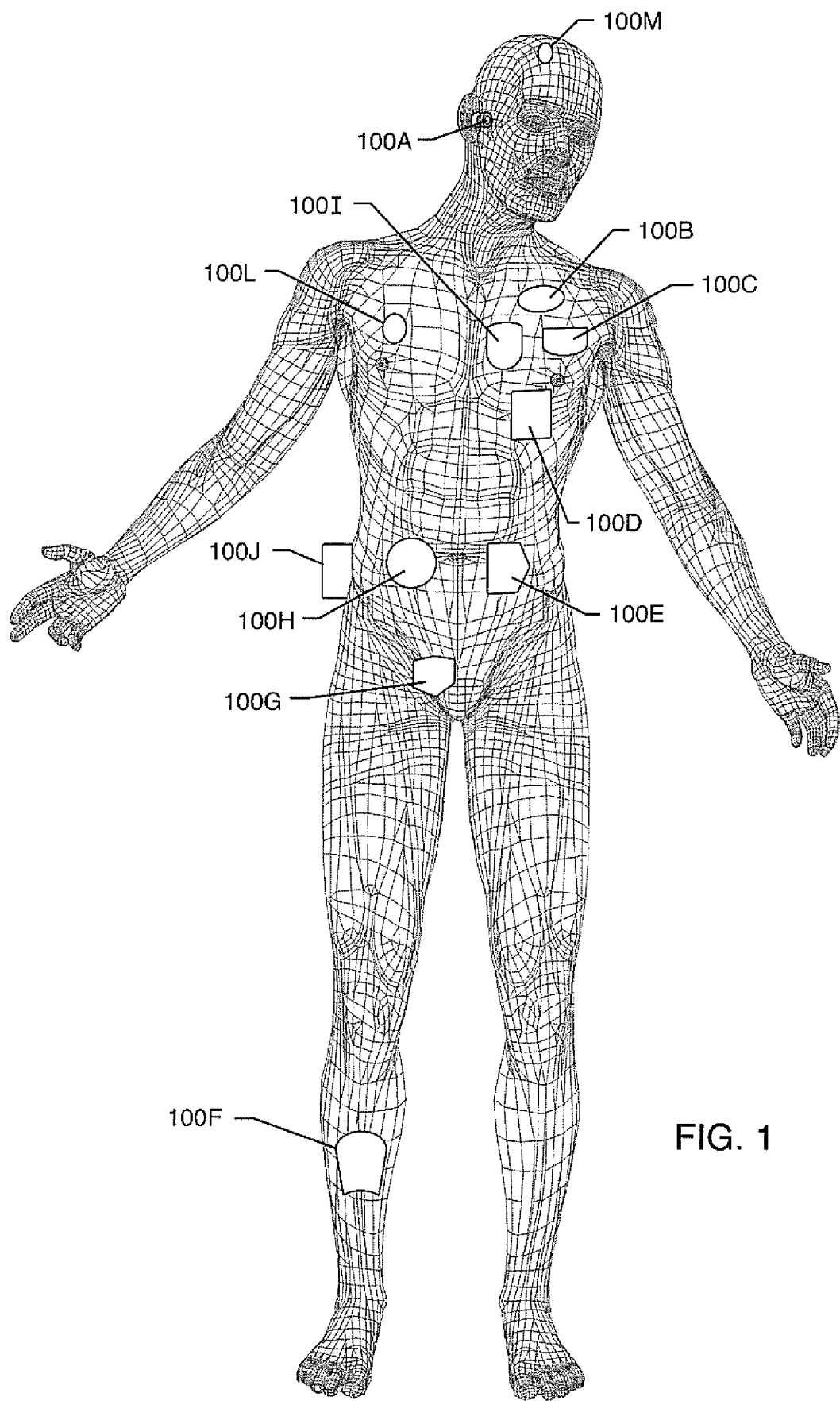
FIG. 1 is a wire-formed diagram of a generic human body showing a number of exemplary implantable medical devices.

FIG. 1 illustrates various types of active implantable and external medical devices 100 that are currently in use. FIG. 1 is a wire formed diagram of a generic human body showing a number of implanted medical devices. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of a seizure and also providing electrical stimulation to brain tissue to prevent the seizure from actually happening. The leadwires that come from a deep brain stimulator are often placed using real time imaging. Most commonly such leadwires are placed during real time MRI. 100C shows a cardiac pacemaker, which is well-known in the art and may have endocardial or epicardial leads. Implantable pacemakers may also be leadless. The family of cardiac pacemakers 100C includes the cardiac resynchronization therapy devices (CRT-P and CRT-D) and leadless pacemakers. CRT-P devices are unique in that they pace both the right and left ventricles of the heart to help them contract at the same time to help the heart pump more efficiently. A CRT-D device is a special device for heart failure patients who are also at high risk for sudden cardiac death. While functioning like a normal pacemaker to treat slow heart rhythms and also delivering small electrical impulses to the left and right ventricles to help them contract at the same time, the CRT-D device is also capable of delivering shock to the heart to treat dangerously fast heart rhythms that can lead to sudden death. The 100C device family also includes all types of implantable loop recorders or biologic monitors, such as cardiac monitors. 100D includes the family of left ventricular assist devices (LVAD's) and artificial hearts. 100E includes an entire family of drug pumps, which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillator (ICD) devices and also includes the family of congestive heart failure devices (CHF). This is also known in the art as cardiac resynchronization therapy devices, otherwise known as CRT devices. 100J illustrates an externally worn pack. This pack could be an external insulin pump, an external drug pump, an external neurostimulator, a Holter monitor with skin electrodes or even a ventricular assist device power pack. Referring once again to element 100C, the cardiac pacemaker could also be any type of biologic monitoring and/or data recording device. This would include loop recorders or the like. Referring once again to FIG. 1, 100I is described as an implantable defibrillator. It should be noted that these could be defibrillators with either endocardial or epicardial leads. This also includes a new family of subcutaneous defibrillators.

Figure 2:
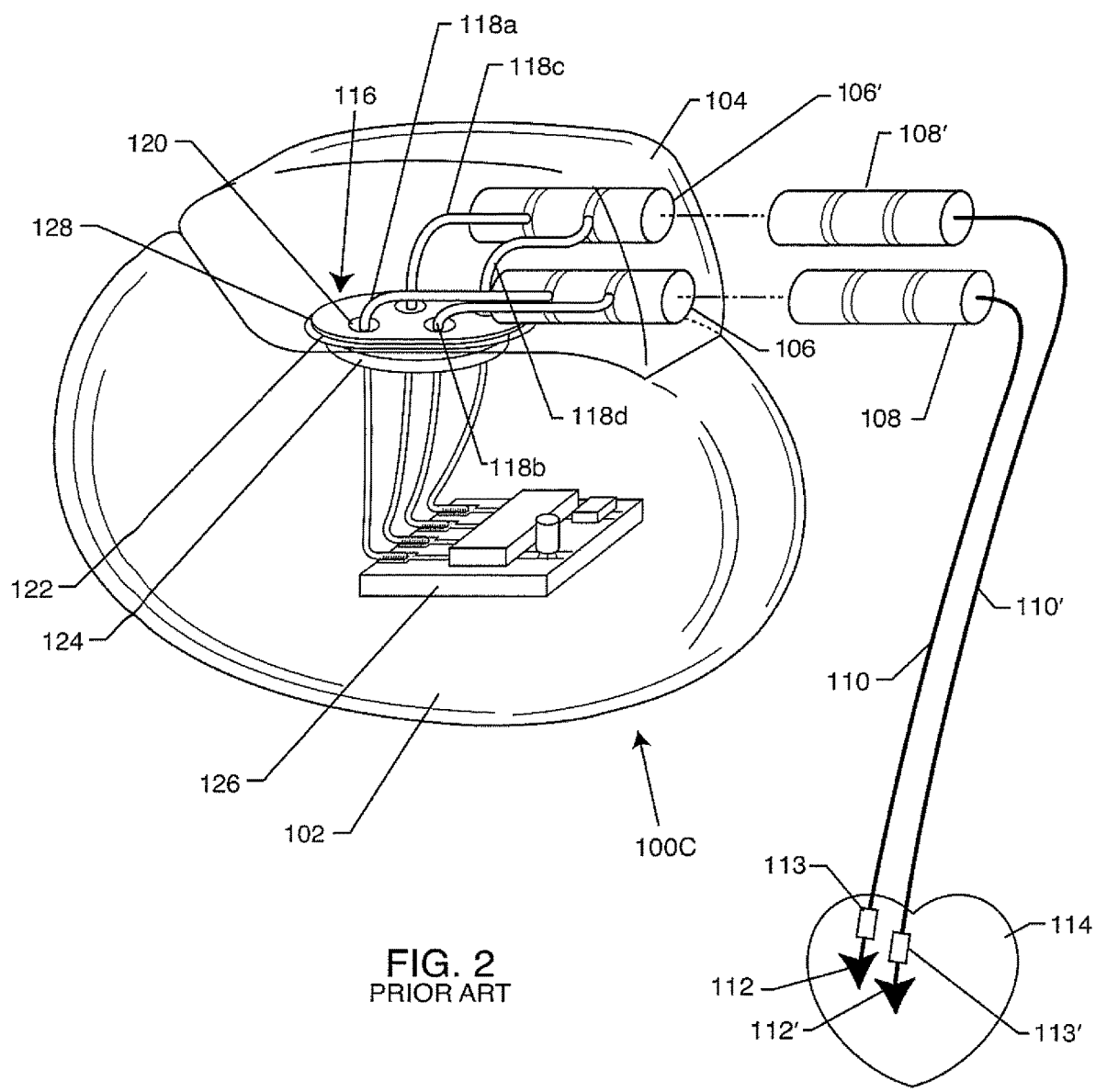
FIG. 2 is a side view of a prior art cardiac pacemaker.

FIG. 2 illustrates a side cutaway view of a prior art cardiac pacemaker 100C. The pacemaker electronic circuits are housed in a hermetically sealed and conductive electromagnetic shield 102 (typically titanium). There is a header block assembly 104 generally made of thermal-setting non-conductive plastic, such as Tecothane™. This header block assembly 104 houses one or more connector assemblies generally in accordance with ISO Standards IS-1, IS-2, or more modern standards, such as IS4 or DF4. The header block connector port assemblies are shown as 106 and 106'. Implantable leadwires 110, 110' have proximal plugs 108, 108' and are designed to insert into and mate with the header block connector cavities 106 and 106', or, alternatively, directly into the pulse generator itself for devices that do not have header block assemblies.

Referring once again to FIG. 2, one can see an active electronics AIMD circuit board 126. Active circuit boards require a source of electrical energy, energy storage, power, and combinations thereof. The electrical energy source comprises a primary battery, a secondary battery, or both; the energy storage source comprises an energy storage capacitor, and the power source comprises an electrical energy system, a power system, or both. Active electronics include at least one microelectronic or microchip component, for example, but not limited to, an application-specific integrated circuit (ASIC) chip or an integrated circuit (IC) chip. As will be further discussed, a passive electronics electromagnetic interference (EMI) filter chip may alternatively be disposed in the location of the feedthrough capacitor 124.

As used herein, the term "lead" refers to an implantable lead containing a lead body and one or more internal lead conductors. A "lead conductor" refers to the conductor that is inside of an implanted lead body. The term "leadwire" or "lead wire" refers to wiring that is either inside of the active implantable medical device (AIMD) housing or inside of the AIMD header block assembly or both. Furthermore, as used herein, in general, the terms lead, leadwire and pin are all used interchangeably. Importantly, they are all electrical conductors. This is why, in the broad sense of the term, lead, leadwire or pin can all be used interchangeably since they are all conductors. The term "conductive pathway" can also be used to be synonymous with lead conductor, lead, leadwire or pin or even a circuit trace. As described herein, composite conductive sintered paste filled vias passing through an insulator in nonconductive relation with a ferrule electrically acts the same as leadwire, lead wire, or pin. These sintered paste filled vias may also incorporate co-fired solid leadwires. As used herein, the term paste generally refers to pastes, inks, gels, paints, cermets, and other such metal and/or metal/ceramic sinterable material combinations that can be flowable, injectable, pressed, pulled, pushed or otherwise movable into an orifice or via. Post-sintering, the solvents and binders are baked out and, after sintering, the paste becomes a densified solid with monolithic structure. Additionally, AIMD, as defined herein, includes electronic circuits disposed within the human body that have a primary or secondary battery, or have an alternative energy source, such as energy induced by motion, thermal or chemical effects or through external induction. As used herein, the term "header block" is the biocompatible material that attaches between the AIMD housing and the lead. The term "header block connector assembly" refers to the header block including the connector ports for the leads and the wiring connecting the lead connector ports to the hermetic terminal subassemblies which allow electrical connections to hermetically pass inside the device housing. It is also understood by those skilled in the art that the present invention can be applicable to active implantable medical devices that do not have a header block or header block connector assemblies such as cochlear or retinal implants.

Figure 2A:
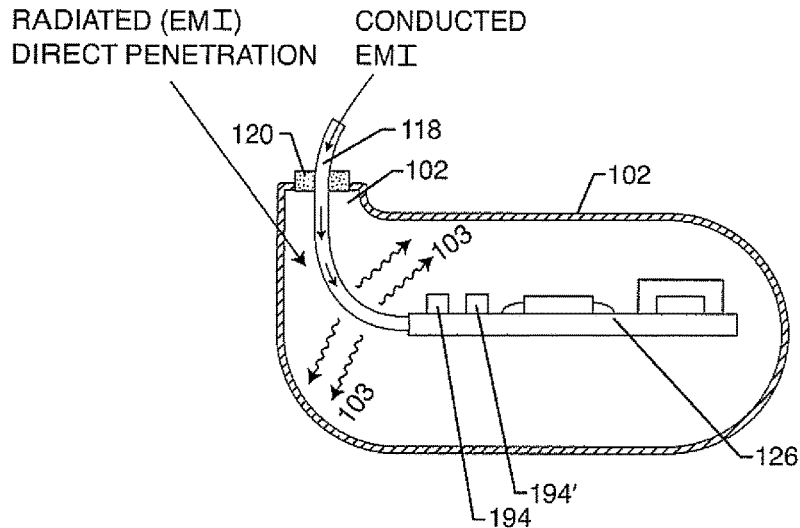
FIG. 2A is a sectional view of the prior art pacemaker of FIG. 2.

FIG. 2A shows an exemplary sectional view of the AIMD previously disclosed in FIG. 2. In this case, MLCC chip capacitor 194, 194' filter components are undesirably located on the AIMD circuit board 126, which is disposed at a distance from the hermetic seal insulator 120 inside the hermetically sealed housing 102 of the AIMD. In this case, radiated EMI directly penetrates through the insulator 120 into the interior of the AIMD housing 102. In addition, conducted EMI, which is coupled to implanted leads by induction or antenna action, can enter the AIMD housing by way of its leadwires. FIG. 2A is thus a representation of poor practice as the EMI is allowed to enter inside of the AIMD housing 102 before the EMI is filtered by the MLCC chip capacitor 194, 194' of other filter components. This can cause the EMI to reradiate on the inside of the AIMD housing, as shown by arrows 103. At high frequencies, this unfiltered EMI can dangerously couple to AIMD sensitive circuits, such as pacemaker sense circuits. Such unfiltered EMI can thereby cause malfunction of the AIMD. In the case of cardiac implantable electronic devices (CIED) such as an implantable defibrillator or pacemaker, this EMI interaction can dangerous, even life-threatening.

Figure 2B:
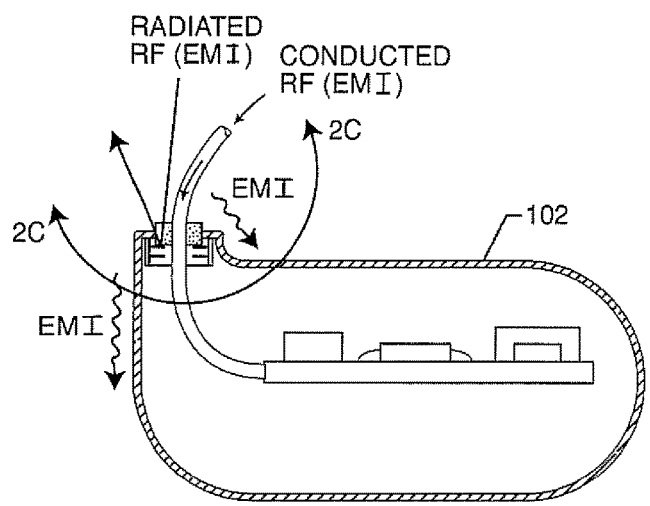
FIG. 2B illustrates how an EMI filter can reflect and divert EMI energy from entering the pacemaker of FIG. 2A.

FIG. 2B is similar to FIG. 2A, except now a feedthrough EMI filter capacitor 124 is disposed adjacent to the hermetic seal insulator 120. The internal electrode plates, particularly the ground electrode plates of the feedthrough EMI filter capacitor 124, reflect radiated EMI such that it cannot enter inside the AIMD housing 102. At the same time, the filter capacitor diverts conducted EMI, which is dissipated harmlessly to the AIMD housing 102.

Figure 2C:
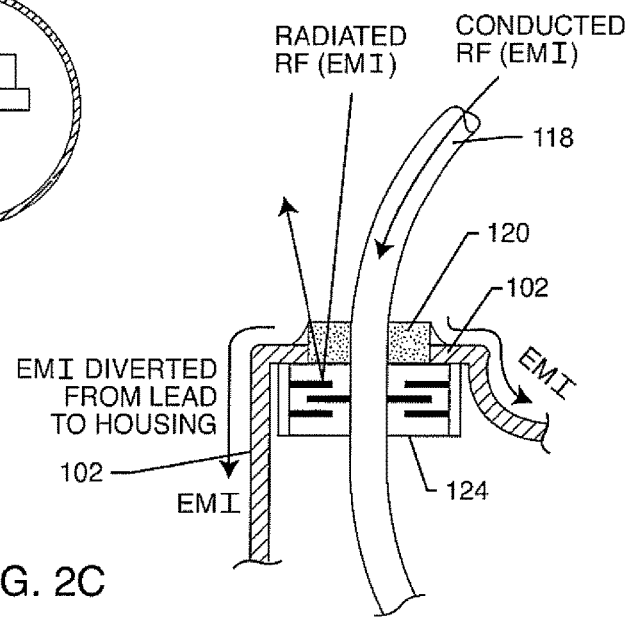
FIG. 2C is a sectional view taken from FIG. 2B, illustrating how a feedthrough capacitor works to reflect and divert EMI.

FIG. 2C is taken from section 2C-2C of FIG. 2B illustrating the internal electrode plates of the feedthrough EMI filter capacitor 124 and its connection to the AIMD housing 102, which is system ground. As defined herein, system ground is the housing 102 of an AIMD, which can also optionally include a metallic electrically conductive feedthrough ferrule 122 hermetically sealed to an insulator 120 of the feedthrough, the ferrule being mechanically and electrically attached to an opening in the AIMD housing by processes, such as, but not limited to, laser welding or brazing. Alternatively, the ferrule may be formed as a contiguous extension of the AIMD housing.

As used herein, the acronym AIMD stands for active implantable medical devices. A family of AIMDs is described in FIG. 1. As defined herein, active components, such as an active implantable medical device or an active electronic circuit board, require a source of power or energy, such as a primary or a secondary battery. There are other sources of energy involving wireless energy transfer, converting ultrasonic waves or even energy harvesting derived from biomechanical motions of human organs, such as cardiac motion, blood flow, breathing and the like, which collects and stores electric power or energy for later use. Passive AIMD electronic components or passive AIMD circuit boards do not require a source of power or energy and consist of passive components, including capacitive, inductive, and resistive elements. Also, as defined herein are CRT-P and CRT-D devices. These are cardiac resynchronization pacemakers and cardiac resynchronization defibrillators. They are different than prior pacemakers and defibrillators, in that they have a third wire system routed outside the left ventricle and are thereby able to completely resynchronize the heart.

Figure 3:
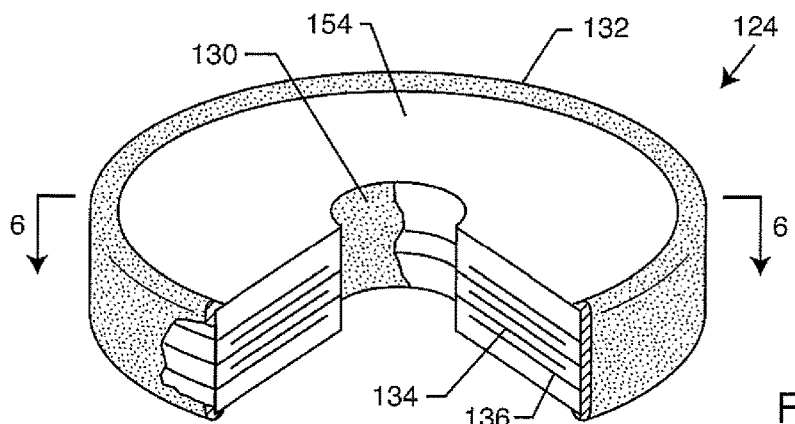
FIG. 3 is a perspective partial cutaway view of a unipolar capacitor.

FIG. 3 illustrates an isometric cut away view of a unipolar feedthrough capacitor. Shown are active electrode plates 134 and ground electrode plates 136 both disposed within a capacitor dielectric 154. There is a feedthrough hole (passageway), including metallization 130. There is also an outside diameter metallization 132.

Figure 4:
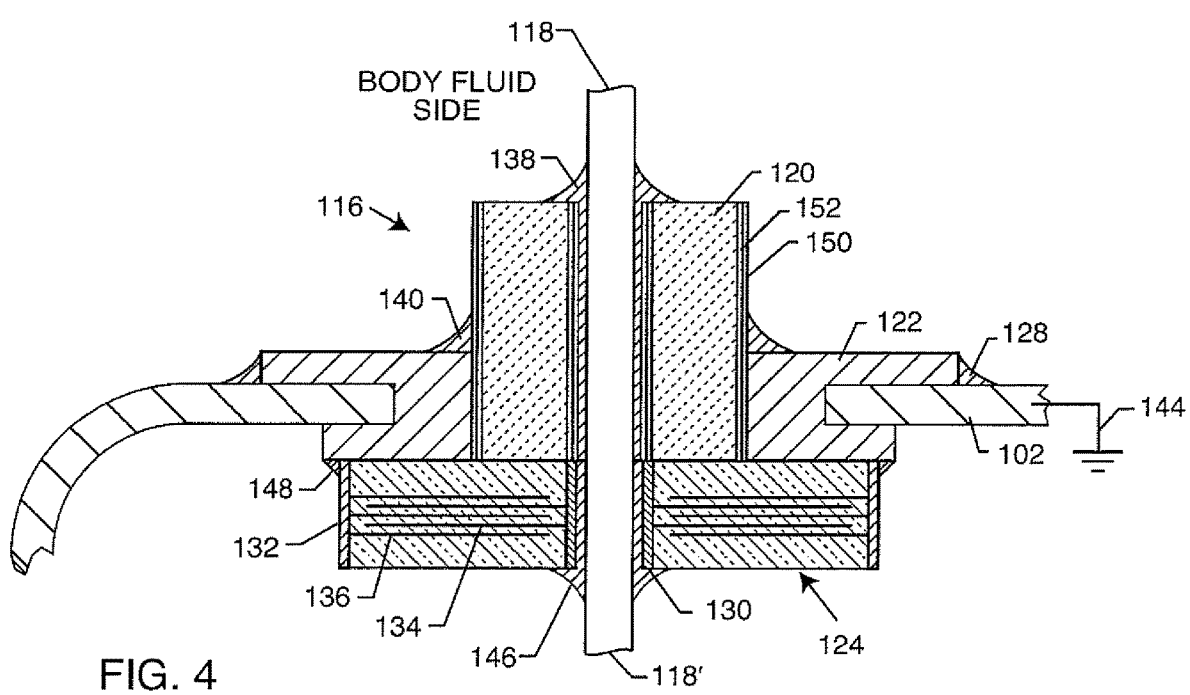
FIG. 4 is a side sectional view of a similar unipolar capacitor of FIG. 3 now mounted to a hermetic feedthrough for an active implantable medical device.

FIG. 4 illustrates a cross-sectional view of the unipolar capacitor of FIG. 3. The unipolar capacitor is mounted to a ferrule 122 of a hermetically sealed feedthrough 116 for an active implantable medical device (AIMD). As shown, the ferrule 122 is configured to be laser welded 128 into an opening of an AIMD housing previously illustrated in FIG. 2 as element 102. The AIMD housing generally comprises titanium, but can comprise other biocompatible electrically conductive materials, and forms an overall electromagnetic shield to help protect AIMD electronics from electromagnetic interference (EMI) emitters, such as cell phones and the like. Accordingly, FIG. 4 shows a ground symbol 144 indicating that EMI signals, which may couple to the body side of the lead 118, can be decoupled or diverted through the feedthrough capacitor 124 to the equipotential electromagnetic shield (the housing of the AIMD). When high frequency EMI signals are diverted from lead 118 to the AIMD housing 102, the EMI signals circulate around the electromagnetic shield (the housing) and are converted into meaningless heat (just a few milli or microwatts).

Referring once again to FIG. 4, one will see an electrical connection material 148 directly connected to the ferrule 122. Typically, the ferrule 122 would comprise titanium, which forms oxides. In fact, it is the oxides of titanium that make it biocompatible. However, these oxides are very resistive or semi-conductive. It was not known at the time the prior art filters of FIG. 4 were being built that filter performance could seriously degrade over time due to titanium oxides. Referring once again to FIG. 4, one can see the traditional circuit ground system, labeled system ground 144. As used herein, system ground, represented by the ground symbol illustrated by FIG. 4 as element 144, can be connected either directly to the AIMD housing 102 or to the ferrule 122. As defined herein, the schematic ground symbols used throughout the present patent drawings represent EMI filter system ground 144. At both low and high frequencies, housing 102 and ferrule 122 are at system ground potential as a result of the continuous laser weld 128 that mechanically and electrically joins them together.

Figure 5:
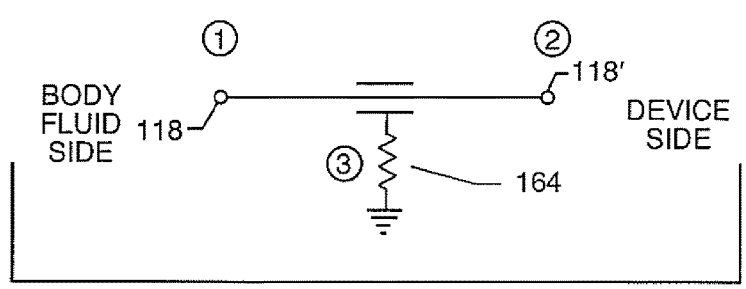
FIG. 5 is an electrical schematic representation of the unipolar filtered feedthrough assembly previously illustrated in FIG. 4.

FIG. 5 illustrates the schematic diagram for the feedthrough capacitor of FIGS. 3 and 4, showing that the feedthrough capacitor is a three-terminal device capable of significant high frequency attenuation along the length of the leadwire extending to the body fluid side lead end 118 and to the device side lead end 118'. Accordingly, the body fluid side lead end 118 is a first terminal, the device side lead end 118' is a second terminal, and the system ground 144, which is the AIMD housing 102, is the third terminal, to which undesirable EMI is diverted. It is known to one skilled in the art that three-terminal feedthrough capacitors have very little to no parasitic series inductance and are therefore very broadband low pass filters. This means that low frequency signals, such as therapeutic pacing pulses or biologic signals, pass through the body fluid side of the lead 118 to the device side of the lead 118' without degradation or attenuation. However, at high frequencies, the capacitive reactance drops to a very low number and desirably, high frequency signals are selectively shorted out from the lead conductor 118, 118' to the ferrule 122 and, in turn, to the conductive housing 102. Referring once again to FIG. 5, one can see the resistance 164 between the filter capacitor and the system ground (144) symbol. This resistance 164 is highly undesirable and results from thickening of oxides on the surface of the titanium between the electrical connection 148 of FIG. 4 and the titanium ferrule 122.

Figure 6:
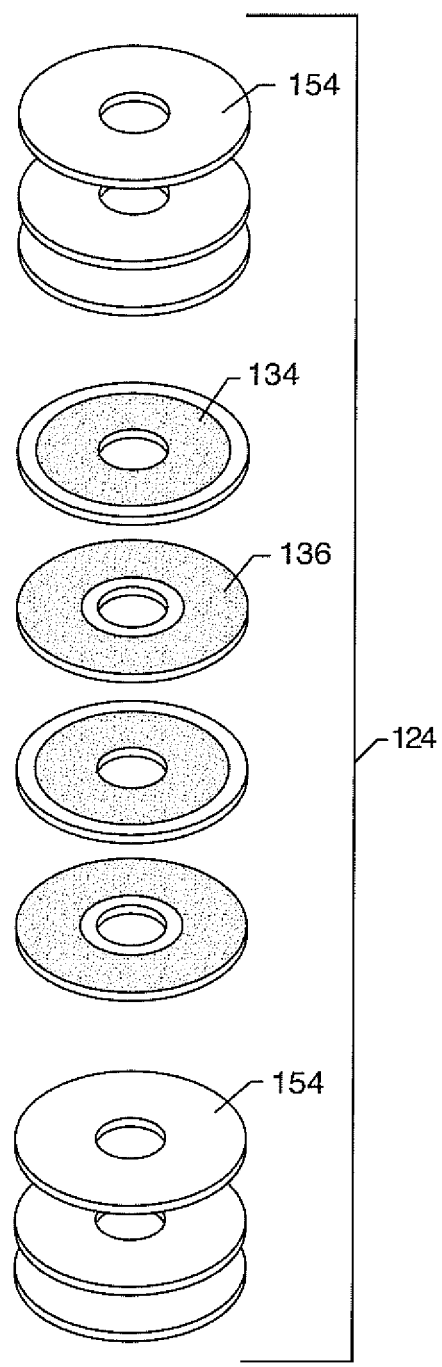
FIG. 6 is generally taken along lines 6-6 from FIG. 3 and is an exploded perspective view of the electrode layer stack up.

FIG. 6 is an exploded view of the unipolar feedthrough filter capacitor of FIG. 3 showing that the feedthrough filter capacitor comprises (from the top down): one or more ceramic cover plates 154; active electrode plates 134 interleaved with ground electrode plates 136; and another set of one or more cover sheets 154. In ceramic engineering, the ceramic dielectrics would typically be of BX or X7R having a dielectric constant of approximately 2000 or higher. It is appreciated that NP0, which is generally a low k dielectric with a dielectric constant below 200, can also be used, which is taught in U.S. Pat. No. 8,855,768, the contents of which are incorporated fully herein by this reference.

Figure 6A:
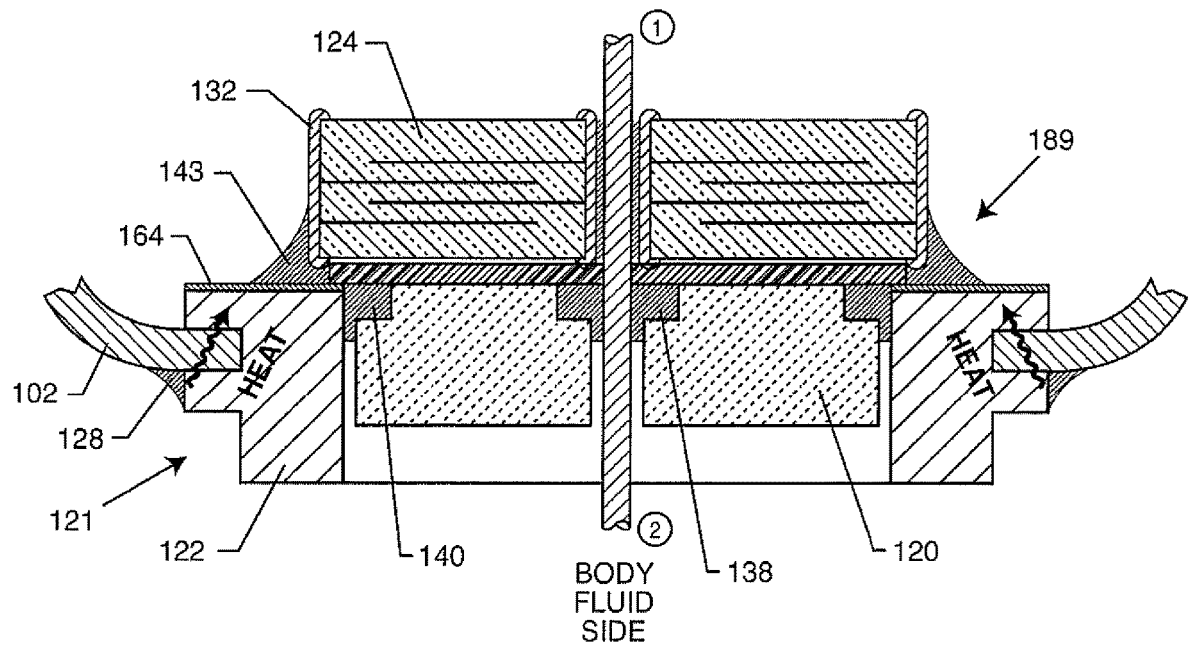
FIG. 6A is a sectional view similar to FIG. 6 showing the undesirable formation of an oxide layer.
Figure 6B:
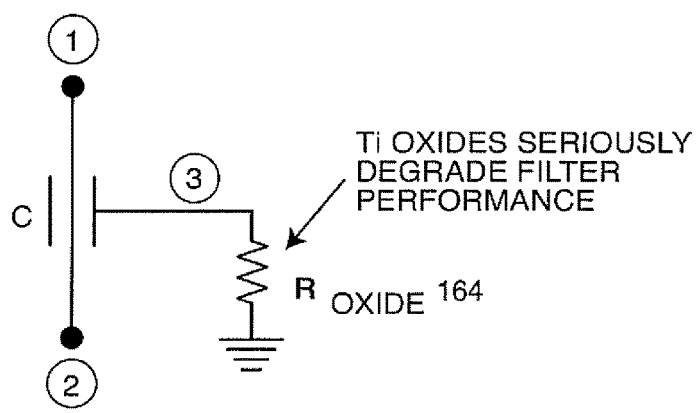
FIG. 6B is the electrical schematic of the oxidized filter of FIG. 6A.

FIG. 6A shows that the feedthrough capacitor ground termination 132 of FIG. 3 has been electrically connected using and electrical connection material 143 directly to ferrule 122. Even if one mechanically or chemically cleans the ferrule of all oxides before the electrical connection is made, a surface oxide 164 can reform between the electrical connection material 143 and the ferrule 122. The electrical connection material typically used in this case is a thermal-setting conductive adhesive, such as a conductive polyimide, a conductive polymer or a conductive epoxy. The ferrule 122 is typically laser welded 128 in an opening of the AIMD housing 102. As previously indicated, laser welding creates a substantial amount of localized heat, which can further accelerate oxide formation. Even if the inside environment of the AIMD housing has been evacuated and backfilled with an inert gas, oxygen can be released from, for example, the thermal-setting conductive adhesive (electrical connection material 143) as the adhesive is heated during the laser welding process. The formation of this surface oxide 164 is very detrimental to filter performance, shown as $R_{OXIDE}$ in FIG. 6B.

Figure 6C:
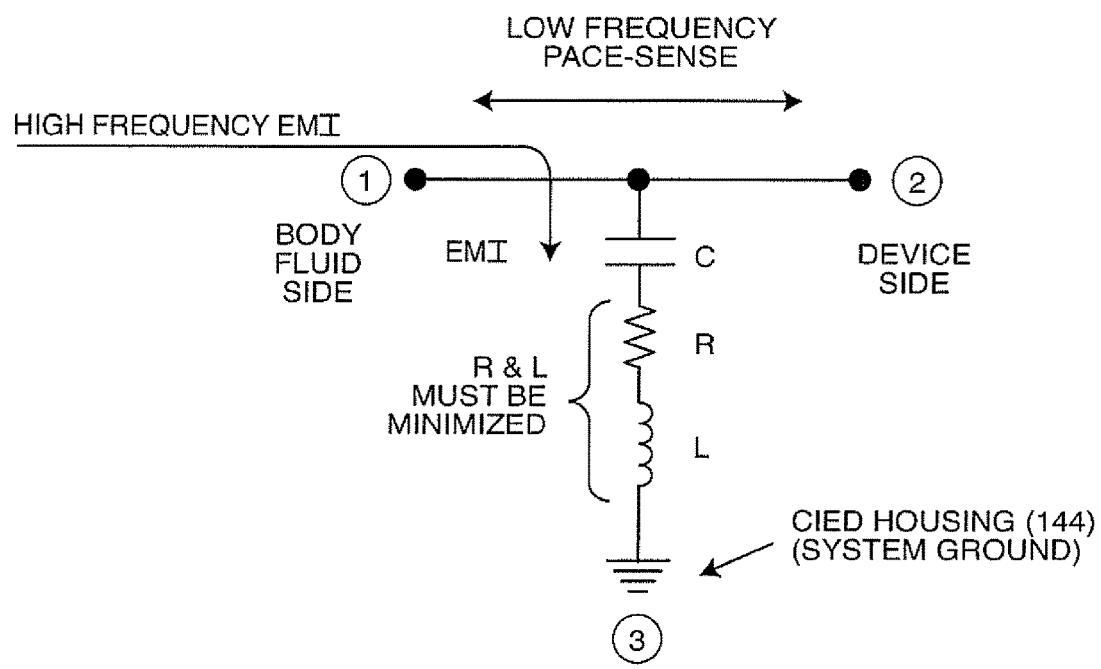

FIG. 6C is a schematic diagram indicating how high frequency EMI entering from a body fluid side (terminal 1) is diverted through a feedthrough capacitor or filter capacitor C. For the filter capacitor to work properly, its parasitic resistance $R_{OXIDE}$ must be minimized. If the resistance value becomes too large, then the filter performance is seriously compromised. Ideally, high frequency EMI is diverted to system ground (terminal 3) as indicated. However, if resistance due to oxides form, then filter performance is degraded, and a significant amount of high frequency EMI enters into the device at terminal 2. When R and L are minimized, then the capacitive reactance $X_C$ will approximately be equal to the impedance Z, as indicated in the equation of FIG. 6C.

Figure 6D:
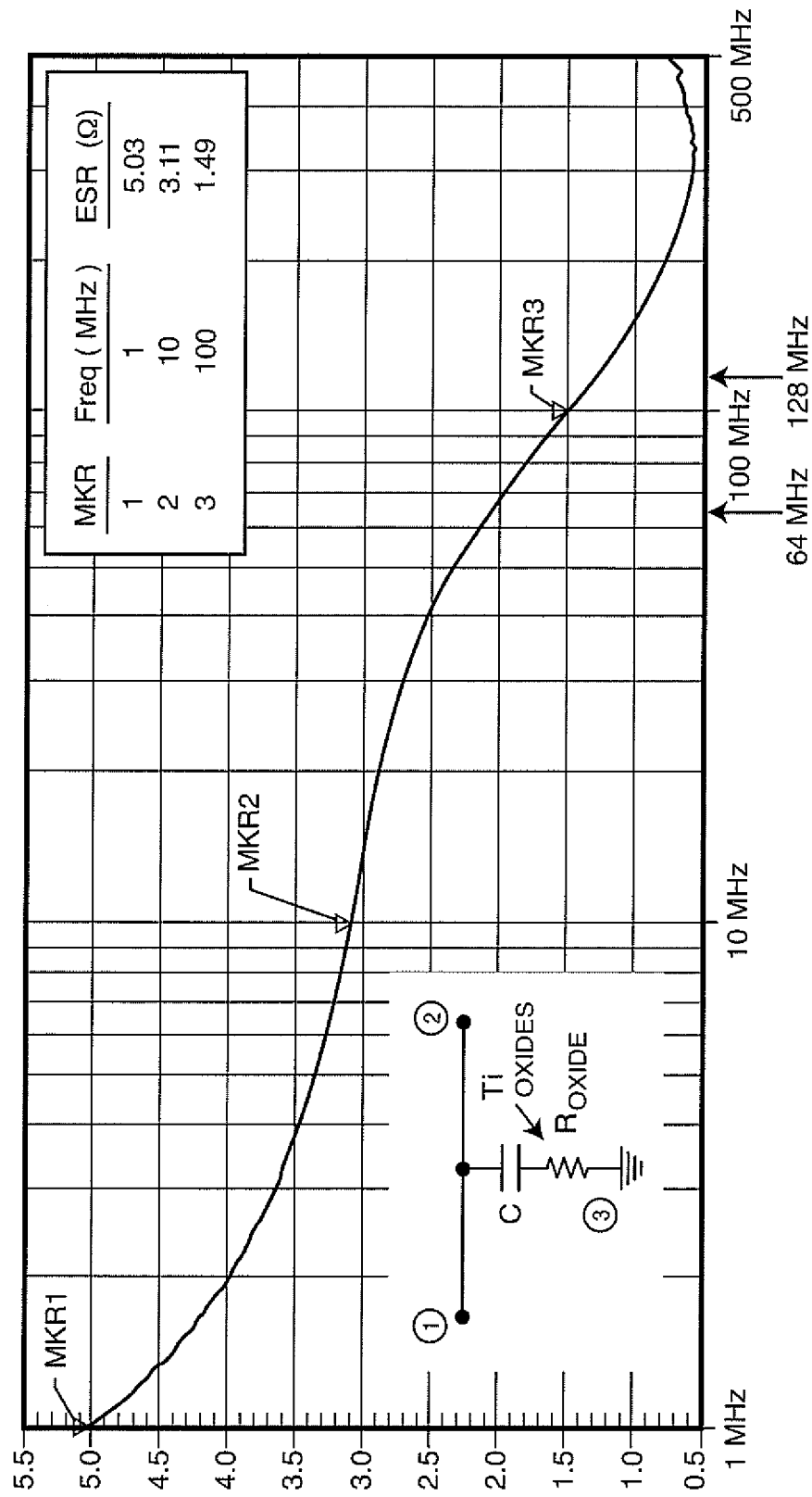
FIG. 6D illustrates an undesirable graph of EMI filter ESR versus frequency that is heavily oxidized.
Figure 6E:
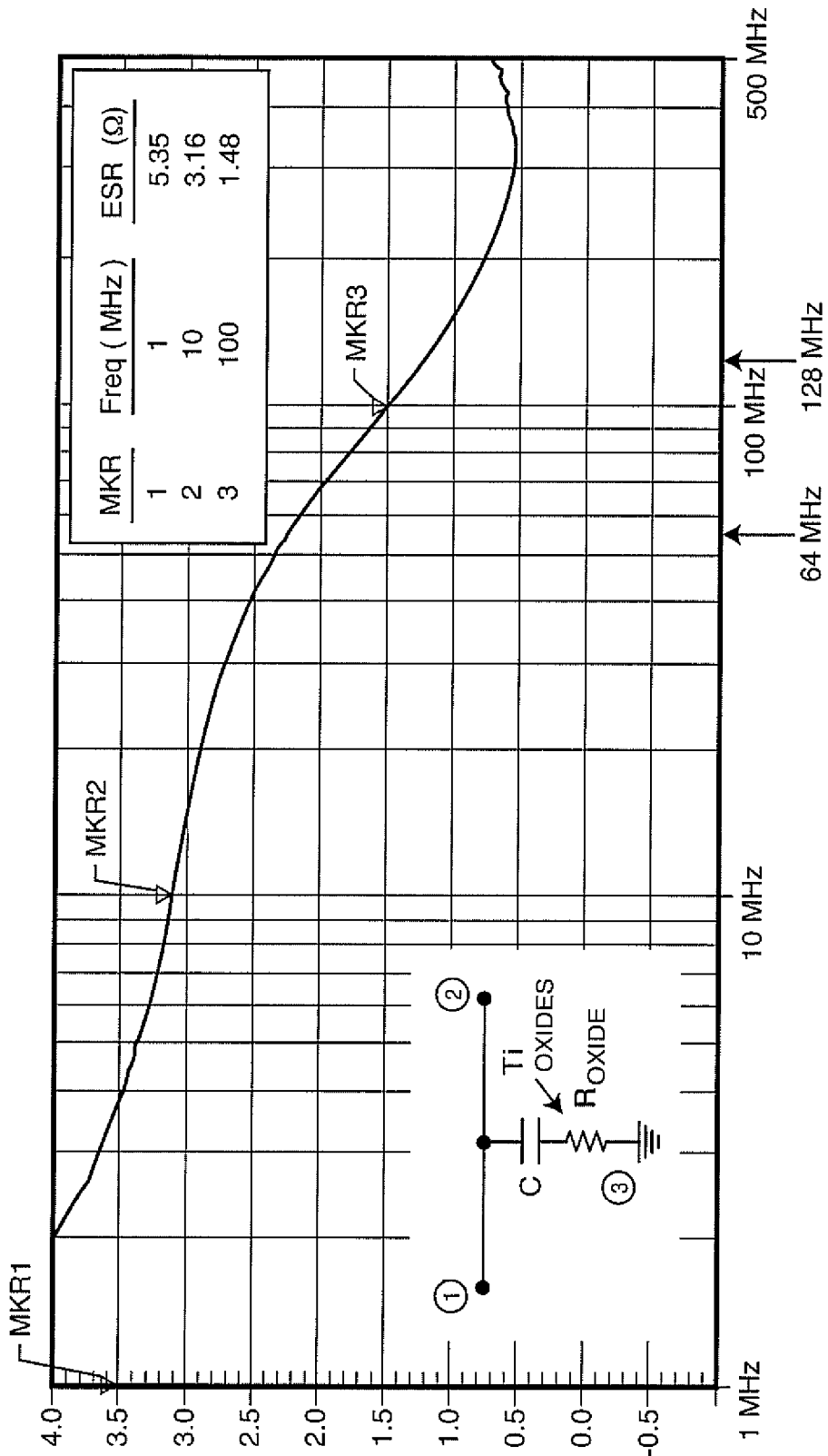
FIG. 6E shows an ESR versus frequency curve for another EMI filter that is attached to a heavily oxidized titanium connection.

FIGS. 60 and 6E are graphs of the equivalent series resistance (ESR) of feedthrough capacitors, as previously illustrated in FIG. 6A. What is alarming is that the expected U-shaped ESR curve of these particular feedthrough capacitors are not present. Even more alarming are the high values of ESR for these two capacitors at 100 MHz (1.49 ohms and 1.48 ohms). It is noted that ESR sweeps identified five discrepant oxidized parts from a lot of 1000 prototype filtered feedthrough parts, and that this lot of filtered feedthrough parts were built with a thermal-setting conductive adhesive directly connecting the capacitor ground termination 132 of the filter capacitor and the ferrule 122 of the feedthrough. The two parts illustrated in FIGS. 60 and 6E are two of the five that exhibited a high ESR.

Figure 6F:
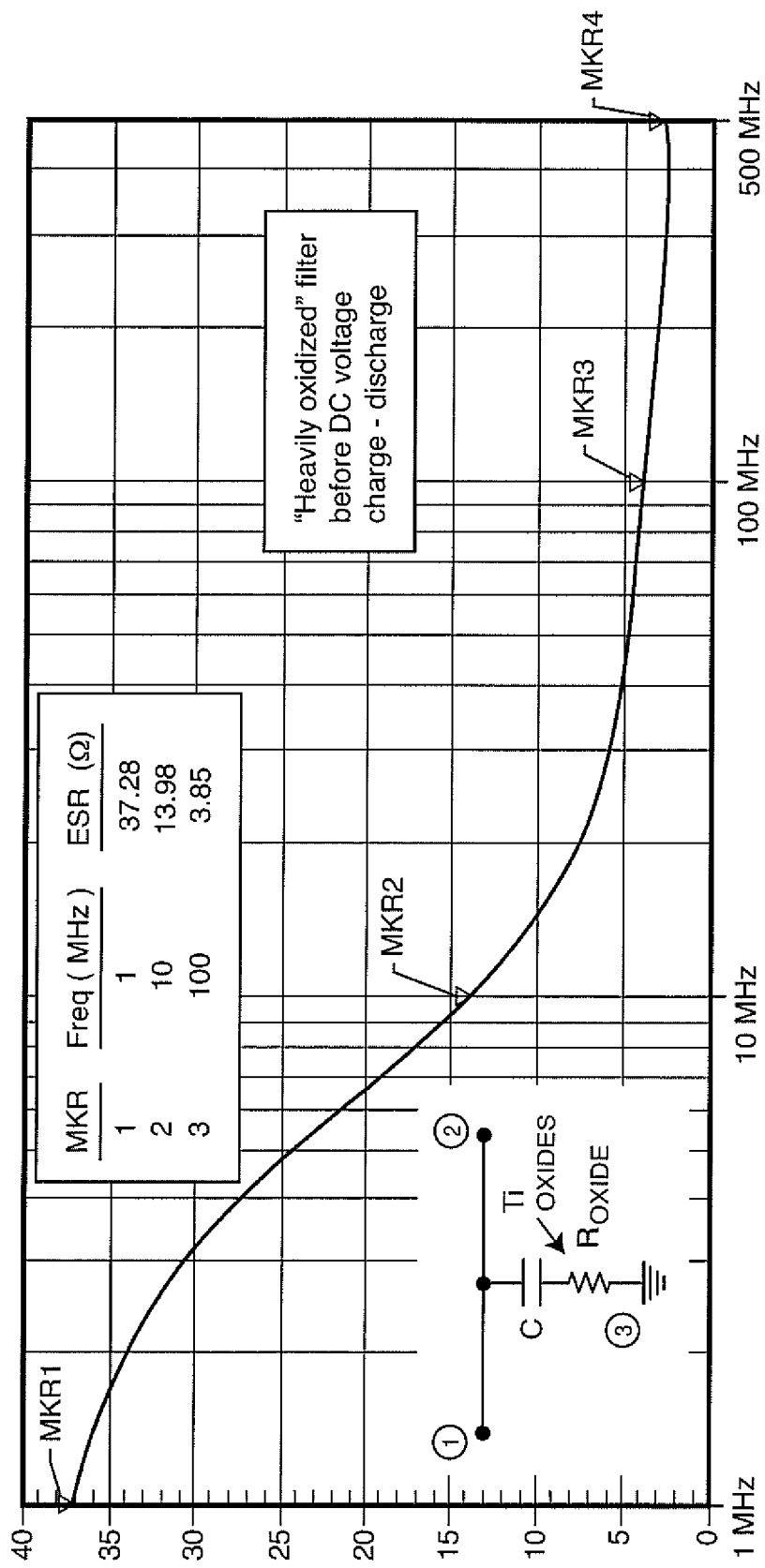
FIG. 6F shows the ESR curve versus frequency for a highly oxidized filter connection.

FIG. 6F illustrates an ESR versus frequency curve of the most oxidized part out of the five parts that had failed in the 1000 piece qualification test lot. In this case, the ESR at 100 MHz is 3.85 ohms. Referring back to FIG. 6C, the capacitive reactance at 100 MHz for a typical 2000 picofarad filter capacitor is 0.796 ohms. One can see that when a surface oxide causes an increased resistance in series with a filter capacitor from less than one ohm to 3.85 ohms the filter performance of that particular filter capacitor seriously and dangerously degrades.

Figure 7:
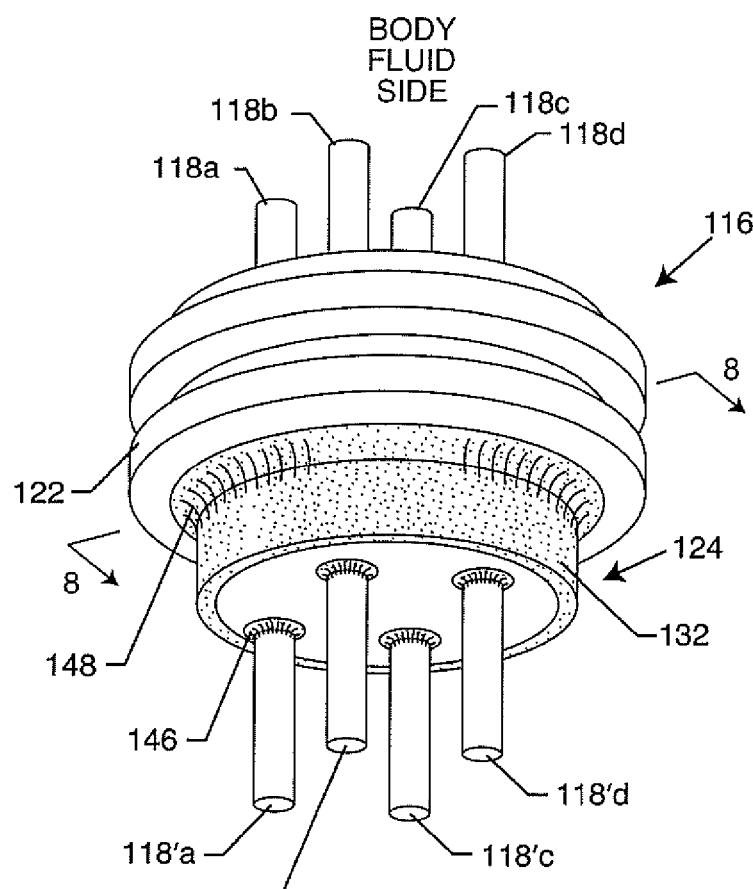
FIG. 7 is a perspective view of a quadpolar feedthrough capacitor and hermetic terminal assembly.

FIG. 7 illustrates a quadpolar feedthrough capacitor and hermetic terminal subassembly 116 comprising four leadwires 118a-118d and four feedthrough holes (quadpolar). The hermetic terminal is a metallic ferrule 122 generally of titanium, which is ready for laser welding 128 into the AIMD housing 102 (not shown).

Figure 8:
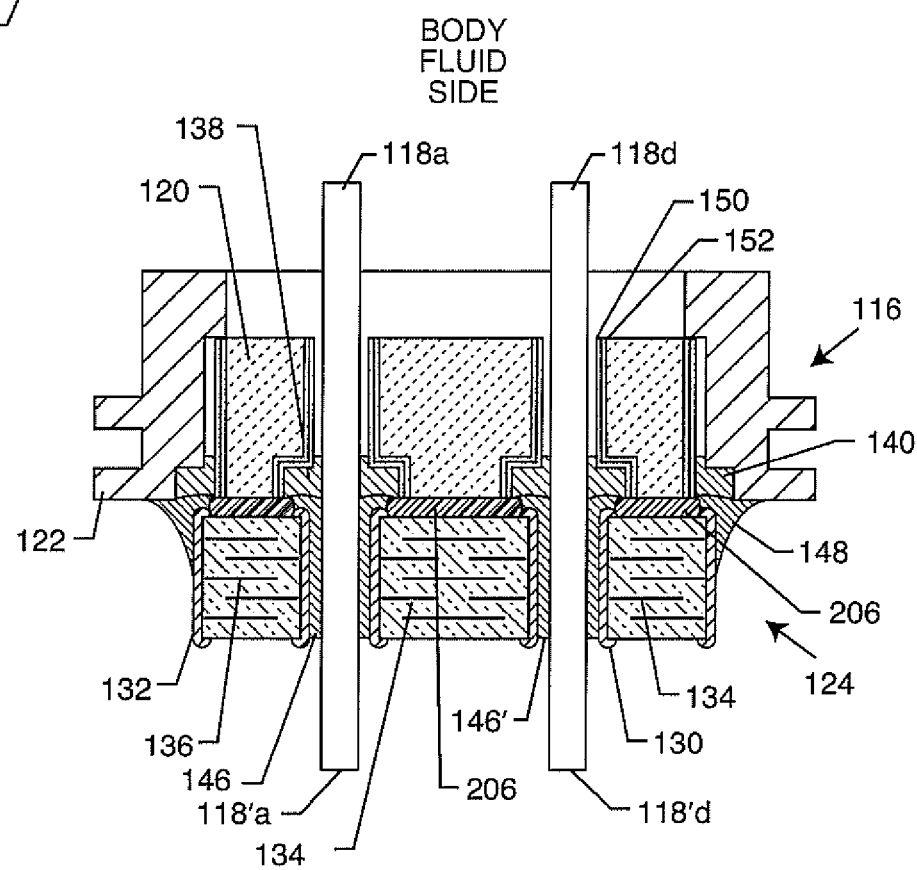
FIG. 8 is a sectional view of the feedthrough and hermetic terminal assembly of FIG. 7 taken along lines 8-8, illustrating ground connection of the EMI filter to an oxide-resistant ferrule hermetic seal gold braze.

Referring once again to FIG. 7, illustrated is a prior art embodiment of an oxide-resistant connection from the capacitor ground metallization using electrical connection material 148. In this case, the electrical connection is not made directly to ferrule 122. This is best understood by looking at FIG. 8, which is a cross-sectional view taken from section 8-8 of FIG. 7. FIG. 8 illustrates that the electrical connection material 148 connecting the capacitor ground termination 132 and the ferrule is at least partially contacting the gold braze 140 that hermetically seals the insulator 120 and the ferrule 122. An electrical connection to an oxide-resistant material, which includes noble metals, for example, a gold braze as shown, provides a very low resistance connection that is essentially free of oxides. Connection to the gold braze of the hermetic seal is further described in U.S. Pat. No. 6,765,779, the contents of which are herein incorporated fully by this reference.

FIG. 8 is a prior art sectional view taken generally from section 8-8 from FIG. 7. The hermetic terminal subassembly leadwires 118a-d pass through the hermetic terminal subassembly insulator 120 in non-conductive relationship and also pass through the feedthrough capacitor 124, wherein the active electrode plates 134 are electrically connected 146 to the hermetic terminal subassembly leadwire 118 and wherein the feedthrough capacitor ground electrode plates 136 are electrically connected 148 to the hermetic terminal subassembly ferrule 122 and the gold braze 140.

Referring once again to FIGS. 7 and 8, in each case it is seen that the hermetic terminal subassembly leadwires 118a-d pass all the way through the entire structure, namely, the hermetic terminal subassembly 116 and the feedthrough capacitor 124. In general, these hermetic terminal subassembly leadwires 118a-d are electrically and mechanically continuous (single material) and pass through from the body fluid side to the inside of the device 100 housing 102. Because the hermetic terminal subassembly leadwires 118a-d pass through from the body fluid side to the inside of the device housing by way of header block connector assembly 104 or the like, it is very important that these hermetic terminal subassembly leadwire 118 materials be biocompatible, biostable and non-toxic. Generally, in the prior art, these hermetic terminal subassembly leadwires are constructed of platinum or platinum-iridium, palladium or palladium-iridium, niobium or the like. Platinum-iridium is an ideal choice because it is biocompatible, non-toxic and is also mechanically very strong. The iridium is added to enhance material ductility and to enable the hermetic terminal subassembly leadwire to sustain bending stresses. Referring once again to FIGS. 7 and 8, it is noted that by connecting the capacitor ground termination 132 to gold braze 140, the outside diameter of the feedthrough capacitor is thereby constrained, which can make the feedthrough capacitor volumetrically inefficient.

Figure 9:
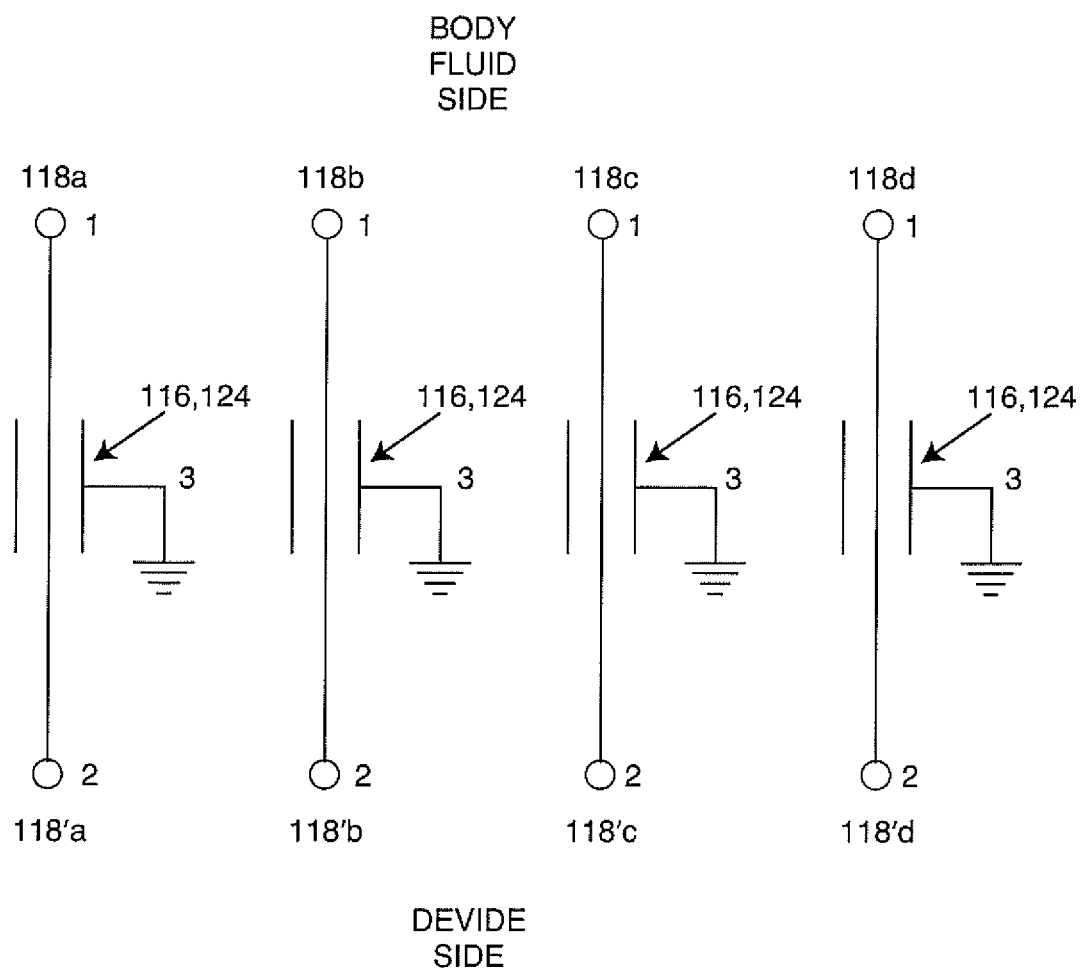
FIG. 9 is an electrical schematic representation of the quadpolar filtered feedthrough capacitor that has an oxide-free connection, as previously illustrated in FIGS. 7 and 8.

FIG. 9 illustrates the schematic of the quad polar hermetic terminal of FIG. 7. The schematic shows the feedthrough capacitors grounded to system ground without series inductance or resistance. The reason inductance is absent is because feedthrough capacitors are unique in that they are three-terminal devices that do not have series inductance. More importantly, the reason that the resistance is absent is because the ESR of the feedthrough capacitor is so low because the capacitor ground is electrically connected to (directly contacts) the hermetic seal insulator to ferrule gold braze, as illustrated in FIG. 8; thus, the resistance can be ignored. In other words, FIG. 9 illustrates that the feedthrough capacitor of FIGS. 7 and 8, exhibits nearly ideal filter performance.

Figure 10:
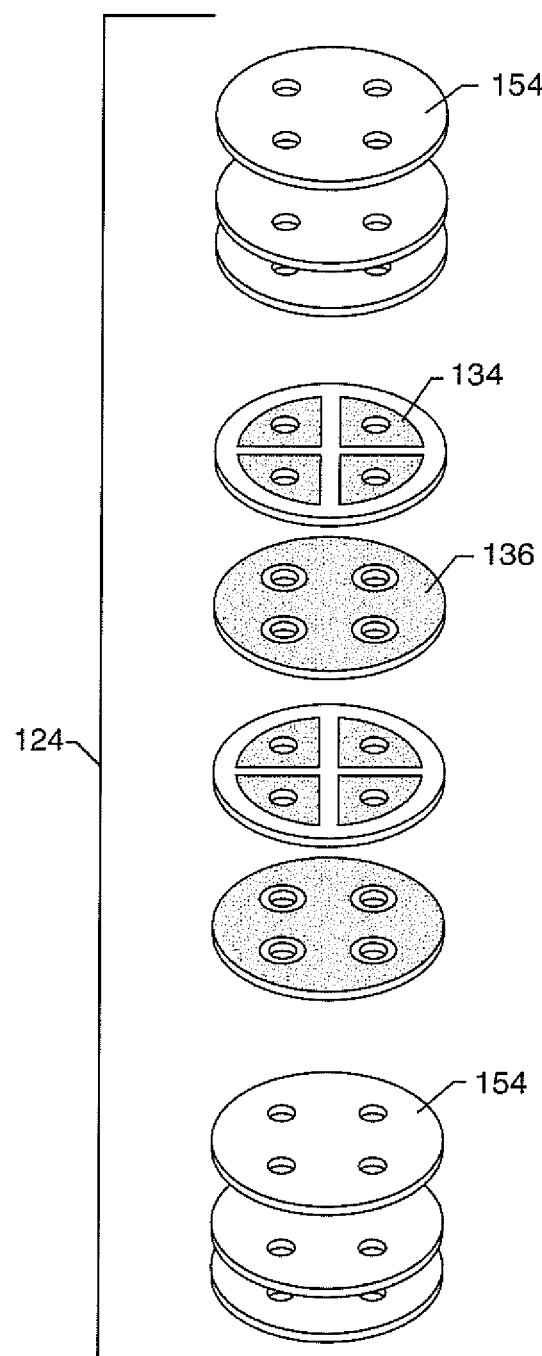
FIG. 10 is an exploded perspective view of the electrode layer stack up of the structure of FIGS. 7 and 8.

FIG. 10 is an exploded view of the quadpolar capacitor 132 of FIG. 7. In the exploded view, shown are four active electrode plates 134 and one ground plate 136. The overlap of the active electrode 134 with the ground electrode 136 determines the effective capacitance area. The greater this overlap area, the higher the capacitance of the feedthrough capacitor. One can also say that this quadpolar capacitor is a multilayer structure. In FIG. 10, there are two active and two ground plates shown. Increasing the number of active and ground plates has the effect of increasing the capacitor's effective capacitance area. It is appreciated that as many as 400 or more ground and active layers can be used.

Figure 11:
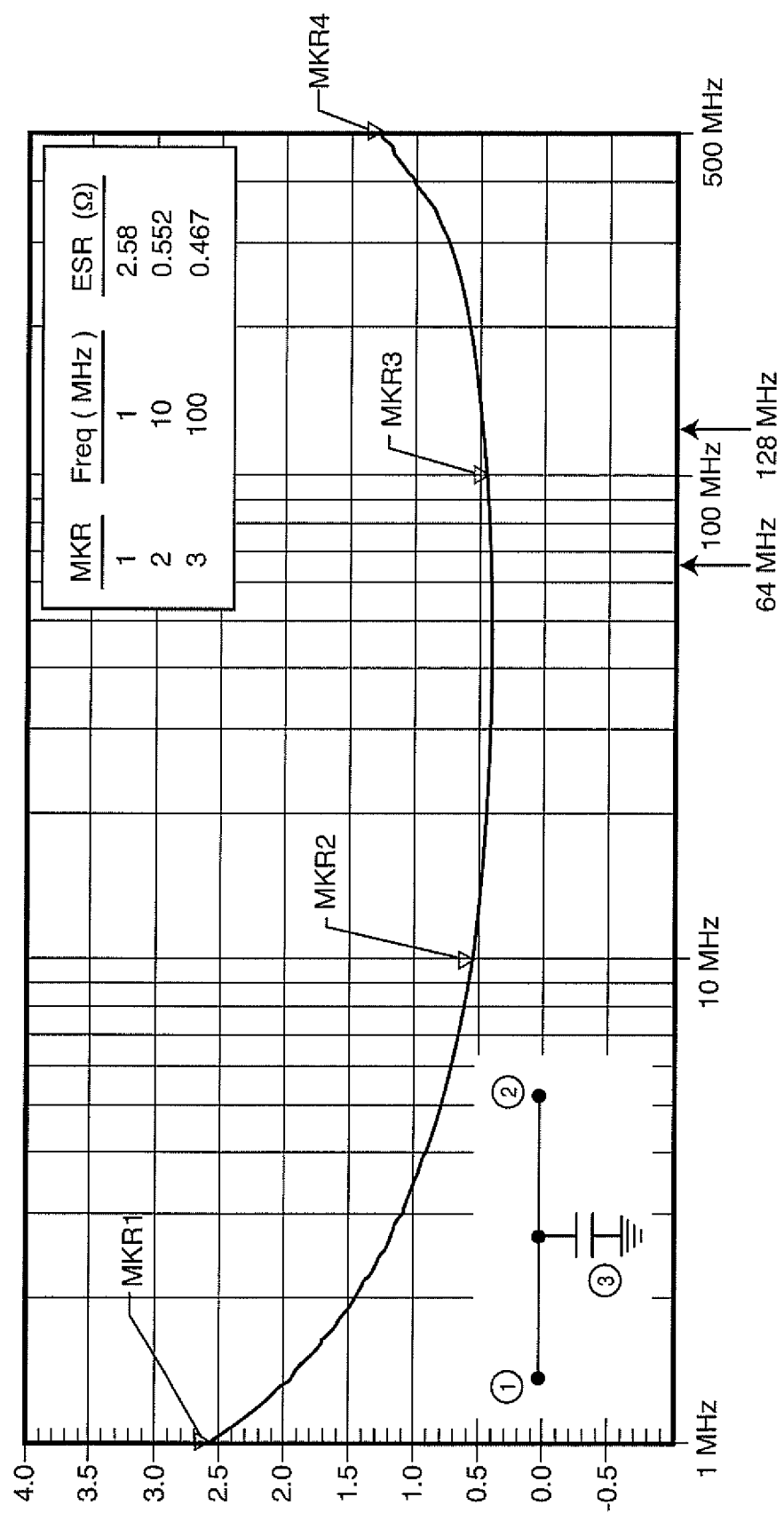
FIG. 11 is an ESR curve versus frequency for the quadpolar filter of FIG. 9, illustrating greatly reduced ESR.
Figure 12:
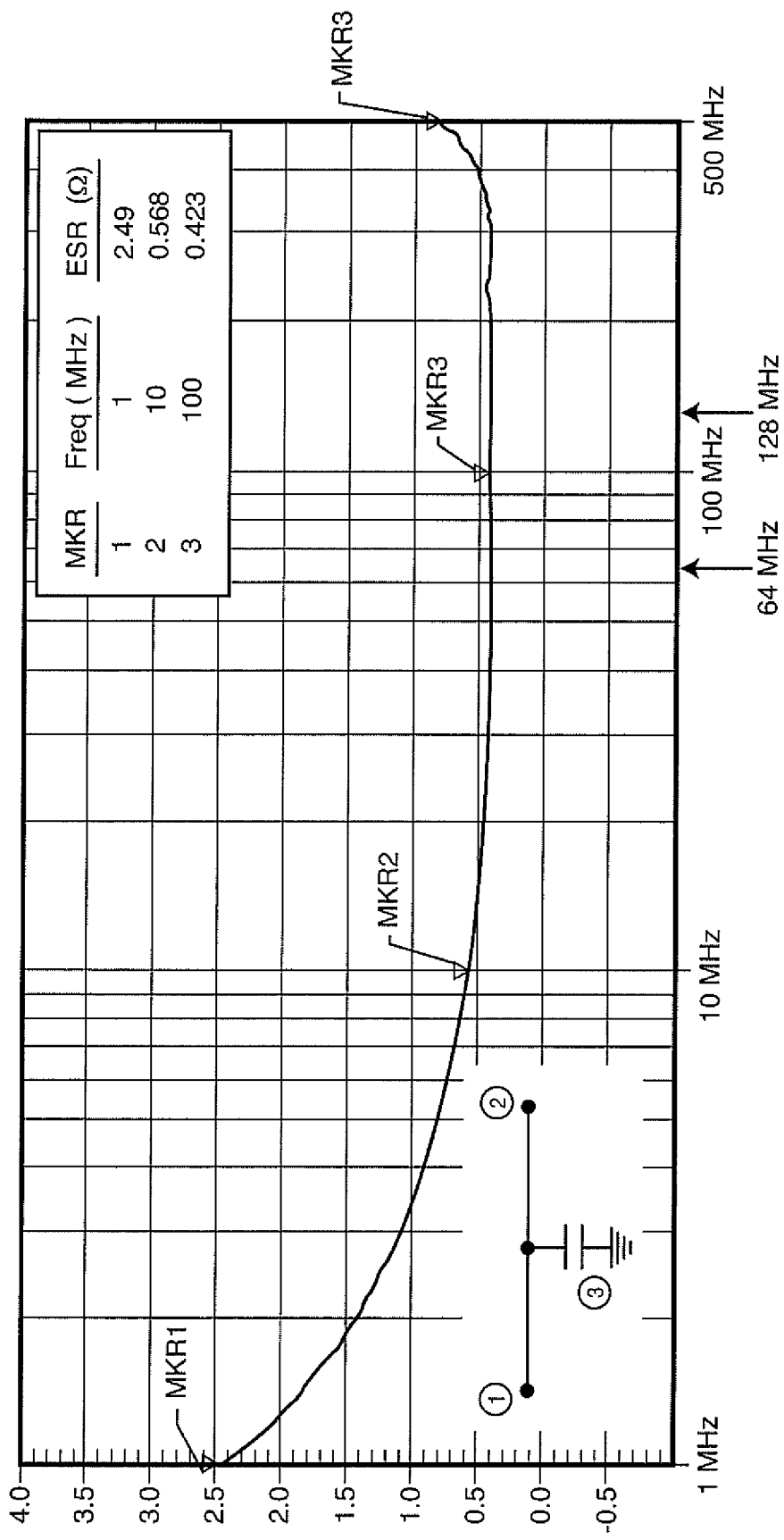
FIG. 12 is an ESR curve from a solar manufacturing lot. Hundreds of parts like these overlay FIGS. 11 and 12 like fingerprints.

FIGS. 11 and 12 are ESR versus frequency curves for ESR sweeps of the filter capacitor of FIGS. 7 and 8, wherein the electrical connection of the filter capacitor to the ferrule is made directly to the gold braze hermetically sealing the insulator and the ferrule of the hermetic terminal. In this case, the ESR at 100 MHz is 0.467 ohms and 0.423 ohms. More importantly, the curves of FIGS. 11 and 12 exhibit the expected classic capacitor U-shaped ESR curve. A U-shaped ESR curve is "the fingerprint" for a filter capacitor and each curve should overlay one another. The reason the ESR increases at low frequency is due to the normal behavior of the capacitor's dielectric loss tangent. At higher frequencies, above 10 MHz, the dielectric loss tangent starts to diminish and the ESR curve is dominated by ohmic loss. The U-shaped curve at high frequencies, such as 500 MHz, is an artifact of a two-terminal measurement for ESR. The increase in ESR at 500 MHz is due to skin effect. The most important performance parameter of an EMI filter is the measurement of insertion loss. Insertion loss is measured on a spectrum analyzer at swept frequencies. The insertion loss tests indicate that the filters of FIGS. 11 and 12 have ideal insertion loss in decibels (dB) of 28.82 dB (ESR 0.467 ohms) and 29.08 dB (ESR 0.422 ohms). One is reminded that insertion loss is a decibel scale, which is logarithmic. A drop in insertion loss of 6 dB will degrade filter performance by half. For the heavily oxidized filters of FIGS. 6D, 6E and 6F, insertion loss severely degrades. Even a drop of 3 dB is a still a significant drop in filter performance. With a 100 MHz ESR of 1.48 ohms, the insertion loss is 23.95 dB. For an ESR of 1.49 ohms at 100 MHz, the insertion loss is 23.91 dB and for the worst part out of this test population that had an ESR of 3.86 ohms at 100 MHz, insertion loss drops to 17.3 dB. Drops in insertion loss like this means that filter performance is very badly degraded, meaning that filter performance is compromised creating a situation that can be very dangerous or even life-threatening for an CIED patient. A comparison of filter capacitor electrical data is shown below in Table 1:

TABLE 1

| Filter Attachment | Filter Capacitor Electrical Data @ 100 MHz | | | |
| --- | --- | --- | --- | --- |
| | Oxidized Titanium Surface* | | Oxide-Resistant Surface** | |
| | ESR | IL | ESR | IL |
| Sample 1 | 1.48 Ω | 23.95 dB | 0.467 Ω | 28.82 dB |
| Sample 2 | 1.49 Ω | 23.91 dB | 0.422 Ω | 29.08 dB |
| Sample 3 | 3.86 Ω | 17.30 dB | | | where: ESR = Equivalent Series Resistant
IL = Insertion Loss
*see FIGS. 6D and 6E
**see FIGS. 6J and 6K FIGS. 13A, 13B and 13C illustrate an internally grounded prior art feedthrough capacitor. In general, internally grounded feedthrough capacitors are known in the prior art with reference to U.S. Pat. Nos. 5,905,627; 6,529,103; 6,765,780 and the like, all of which are fully incorporated herein by reference. Referring once again to FIG. 13A, one can see an internally grounded feedthrough capacitor, which is octapolar (eight active leads). The eight active leads are labeled 118a through 118h on the body fluid side and on the inside of the AIMD housing they are labeled 118'a through 118'h. The ferrule 122 has a peninsula structure 139, which is connected to an internal ground pin 118gnd. Referring now to the octapolar feedthrough capacitor active electrode plates 134, they are designed to overlay in a sandwich fashion the ground electrode plates 136. One skilled in the art will realize that one can stack up as many of these interleaved layers as is required in order to achieve the required capacitance value and other design factors. The internal ground lead 118gnd is electrically connected to the ground electrode plate layers 136. The active electrodes 134a through 134h are each electrically connected through their respective leadwires 118'a through 118'h. The overlap between the active electrodes 134 and the ground electrodes 136 create what is known as effective capacitance area. The active and ground electrode layers may be interleaved with additional ceramic layers to build up the dielectric thickness (not shown). In general, the monolithic ceramic feedthrough capacitor 124, as shown in FIG. 6 as element 124, is a result of laminating the various electrode layers together and then sintering them at a high temperature to form a rigid monolithic ceramic block. This is known as a single feedthrough capacitor that is multipolar (in this case these are octapolar or eight active filtered circuits). One can see that there is a perimeter metallization 132 on the outside of the round capacitor from FIGS. 3 and 7 whereas, in this case in FIG. 6, there is no perimeter metallization 132 at all.

There are several major advantages to internal grounding and removal of the perimeter or diameter metallization 132. This is best understood by referring back to FIGS. 3 through 8. In contrast to FIG. 4, with internal grounding there is no longer a need to apply a diameter metallization 132 as shown in FIGS. 13A, 13B and 13C. In addition, the electrical connection 148 has been entirely eliminated between the capacitor diameter metallization 132 and the gold braze 140 and ferrule 122. The elimination of this electrical connection 148 also makes the capacitor structure 124' much more resistant to mechanical damage caused by subsequent laser welding 128 of the hermetic seal assembly 116 into the AIMD housing 102. A significant amount of heat is produced by laser welding 128 and there is also a mismatch in thermal coefficient of expansion materials. By elimination of the electrical connection material 148, the capacitor 124' is free to float and is therefore, much more resistant to such stresses. Referring once again to FIG. 13B, one can see that the internal ground lead 118'gnd makes a low impedance connection from the capacitor's internal electrode plates 136 to the ferrule 122. This is what eliminates the need for the electrical connection material 148, as previously illustrated in FIG. 4. It is appreciated that only one ground pin is shown in FIG. 6, but some designs may require a multiplicity of ground pins spaced apart such that, there is a very low impedance connection effectively grounding the capacitor internal electrodes 136 at multiple points.

Referring once again to FIG. 13B, one can see the ceramic capacitor subassembly 124' is ready to be installed onto the hermetic terminal subassembly 189. These are shown joined together in FIG. 13C resulting in a hermetically sealed feedthrough capacitor filter assembly 116.

Referring back to FIG. 13B, it is important to clarify some confusion as terms of art. The feedthrough capacitor 124' can also be described as a three-terminal feedthrough capacitor with multiple via holes or feedthrough holes. In a confusing manner, the hermetic terminal subassembly 189 is often referred to in the art as a hermetic feedthrough. Therefore, we have the term feedthrough applying both to the feedthrough capacitor and to the hermetic terminal assembly. As used herein, these are two separate and distinct subassemblies, which are joined together in FIG. 13C to become a feedthrough filter hermetic terminal assembly 116 ready for installation into an opening of an AIMD housing. Referring once again to FIGS. 13A and 13B, one will appreciate that leadwires or lead conductors 118', 118 are continuous leadwires. In other words, on the body fluid side, the leadwire is of the same material as on the device side. This is typical in the prior art. Referring once again to FIG. 13B, one can see that the internal ground lead 118'gnd does not extend through to the body fluid side of the hermetic terminal feedthrough subassembly 189. It is appreciated that it can be easily and readily extended to the body fluid side, but in most embodiments, it is not necessary.

An issue with the use of platinum for hermetic terminal subassembly leadwires 118a-d is that platinum has become extremely expensive and may be subject to premature fracture under rigorous processing such as ultrasonic cleaning or application use/misuse, possibly unintentional damaging forces resulting from Twiddler's Syndrome. Accordingly, what is needed is a filtered structure like a feedthrough capacitor assembly 116 which eliminates these high-priced, platinum, platinum-iridium or equivalent noble metal hermetic terminal subassembly leadwires 118. For additional examples of hermetic terminal subassemblies with feedthrough capacitors that employ leadwires 118, one is referred to U.S. Pat. Nos. 5,333,095, 5,896,267, 5,751,539, 5,905,627, 5,959,829, 5,973,906, 6,008,980, 6,159,560, 6,275,379, 6,456,481, 6,529,103, 6,566,978, 6,567,259, 6,643,903, 6,765,779, 6,765,780, 6,888,715, 6,985,347, 6,987,660, 6,999,818, 7,012,192, 7,035,076, 7,038,900, 7,113,387, 7,136,273, 7,199,995. 7,310,216, 7,327,553, 7,489,495, 7,535,693, 7,551,963, 7,623,335, 7,797,048, 7,957,806, 8,095,224, 8,179,658, the contents of which are fully incorporated herein by reference.

Figure 13D:
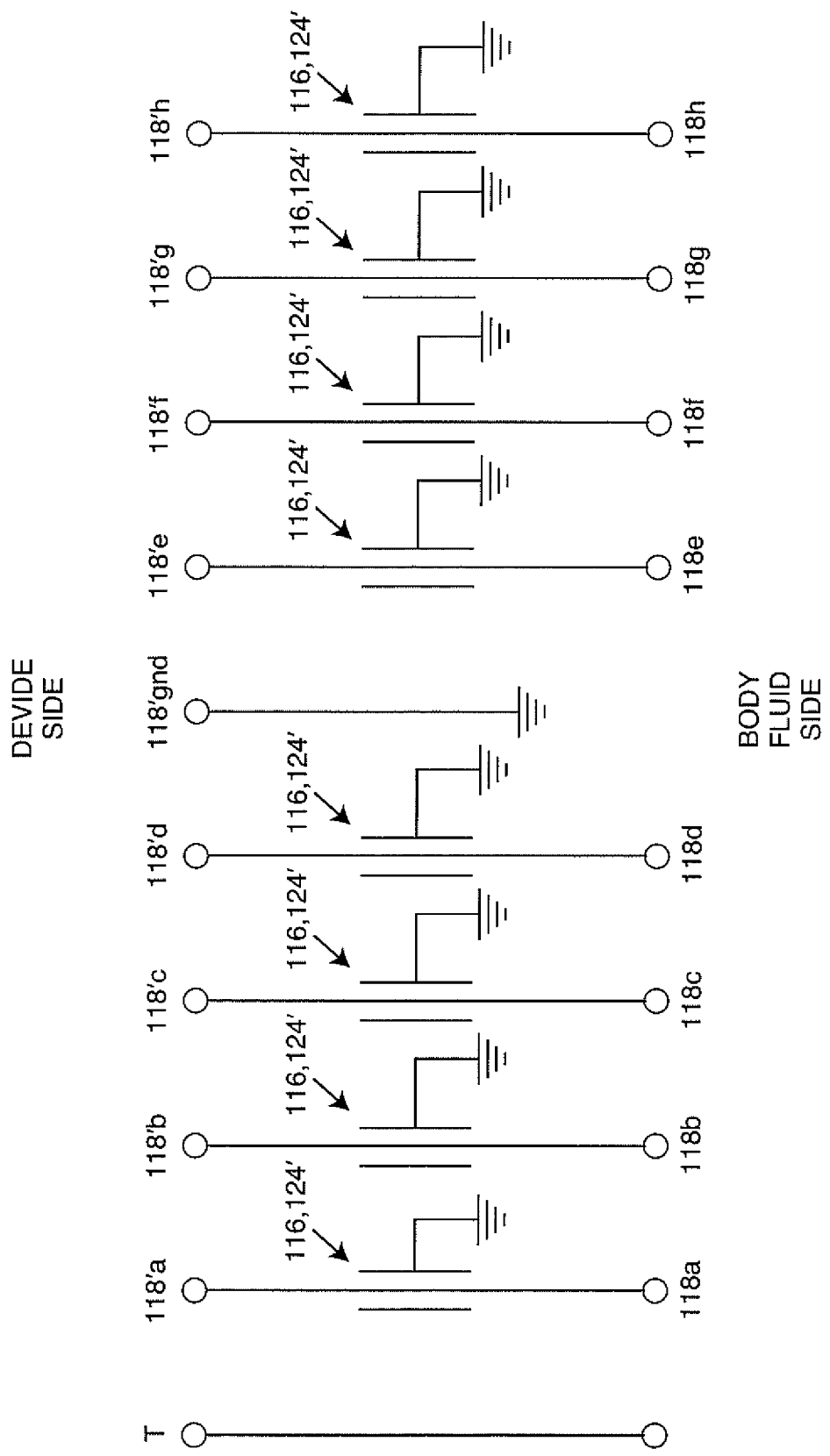
FIG. 13D is the electrical schematic for the feedthrough filtered hermetic terminal previously described in FIGS. 13A, 13B and 13C.

FIG. 13D is the electrical schematic for the feedthrough filtered hermetic terminal 116 previously described in FIGS. 13A, 13B and 13C. Referring once again to FIG. 13D, one can see the telemetry pin T, which passes through the filtered hermetic terminal assembly 116 without any appreciable capacitance to ground. In other words, it would be undesirable to have any high frequency filtering of the telemetry terminal since this would preclude the ability to recover stored information or program the AIMD device remotely. Leadwires 118a through 118h all have feedthrough capacitor hermetic terminal assemblies 116, 124 as shown. The internal ground pin 118gnd is shown only on the device side of the hermetic terminal subassembly 189. Referring once again to FIGS. 13A, 13B, 13C and 13D, it is noted that the feedthrough filter hermetic seal subassembly has been inverted with reference to FIGS. 2, 3 and 4. It should also be noted that the capacitor 124 is still on the device side; it's just drawn inverted.

The internally grounded feedthrough capacitor illustrated in FIGS. 13A, 13B and 13C has a ground connection through an internal ground pin 118'gnd. This ground pin is ideally of platinum or similar noble material that is highly resistant to oxidation. Referring to the schematic diagram FIG. 13D for the filter of FIG. 13C, it is noted that, once again, the filters have no resistance in a system ground 144 connection 102, 122, and are essentially ideal filters. Referring once again to the internally grounded filter of FIGS. 13A, 13B and 13C, there is a disadvantage to the single ground pin 118'gnd. Such a design having a single ground pin central to an elongate feedthrough capacitor as shown can cause undesirable inductance build-up across the feedthrough capacitor ground electrode plates. In order to overcome this effect, several internal ground pins 118'gnd can be added. Another way to look at this is that pins closest to the internal ground pin 118' would have a higher insertion loss, in comparison to the pins most distant from it, such as pin 118'h.

FIG. 14 illustrates a prior art monolithic ceramic capacitor 194. These are otherwise known as MLCC chip capacitors. Multilayer ceramic capacitors are very well known in the prior art and are produced daily in the hundreds of millions. It is appreciated that MLCC chip capacitors are also commonly referred to as multilayer ceramic capacitors or monolithic ceramic capacitors. MLCC chip capacitors are common components in most electronic devices, including computers, modern smart phones and the like. It should be noted here that not all rectangular two-terminal capacitors, as illustrated in FIG. 12, must be ceramic. As used herein, MLCC ceramic chip capacitors shall also include all kinds of stacked tantalum, stacked film and other dielectric type capacitors that form two-terminal rectangular shapes. It will also be appreciated that any of the two-terminal capacitors in the art, including ceramic, film and tantalum can also have other shapes other than rectangular, including cylindrical and the like.

FIG. 15, taken from section 15-15 from FIG. 14, illustrates a cross-section of an MLCC chip capacitor. As can be seen, the prior art MLCC chip capacitor is a two-terminal device having a metallization on the left 130 and a metallization on the right 132. It has overlapping electrodes as illustrated in FIGS. 15A and 15B. It has an effective capacitance area created by the overlap of the left-hand electrodes 134 with the right-hand electrodes 136.

Figure 16:
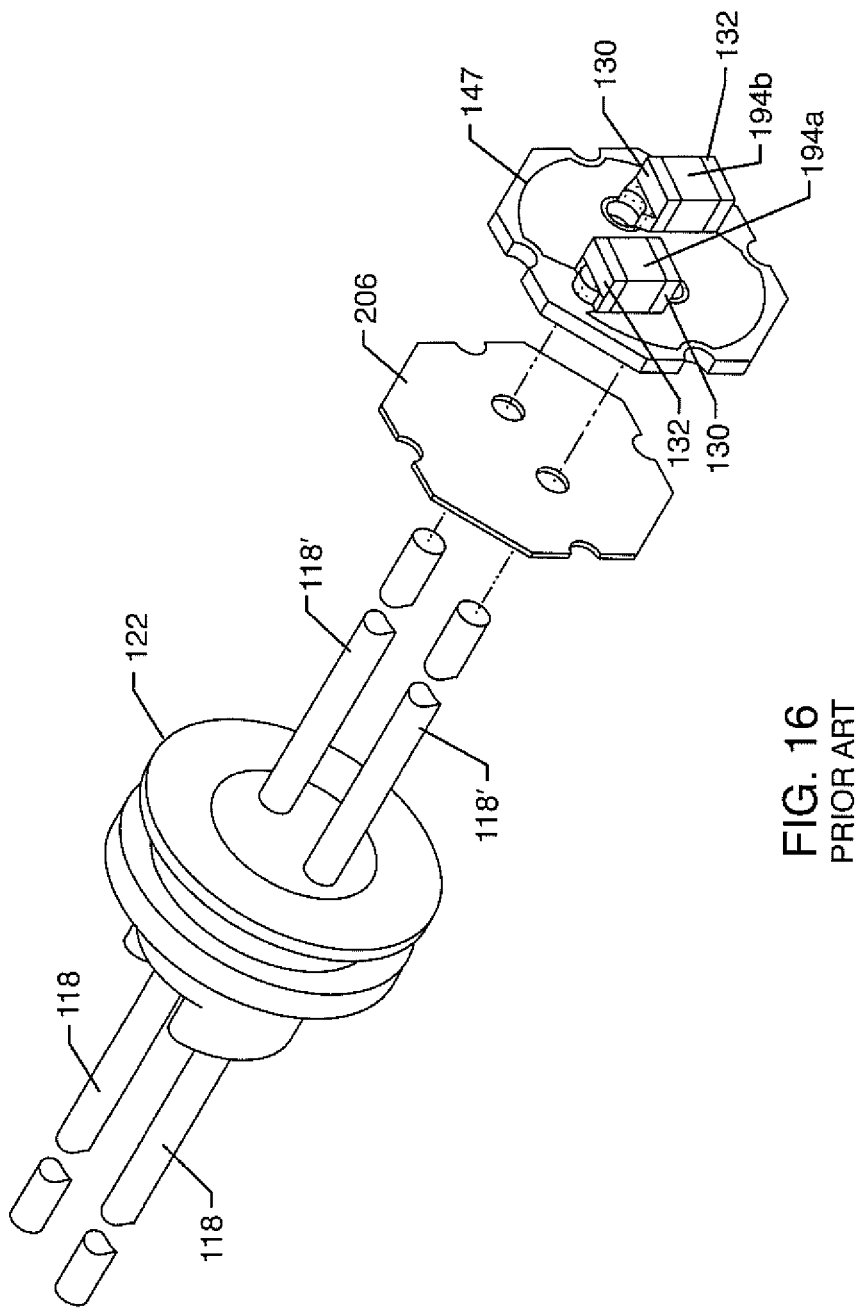
FIG. 16 illustrates a prior application of an MLCC chip capacitors attached to hermetic seal subassembly of an active implantable medical device.
Figure 17:
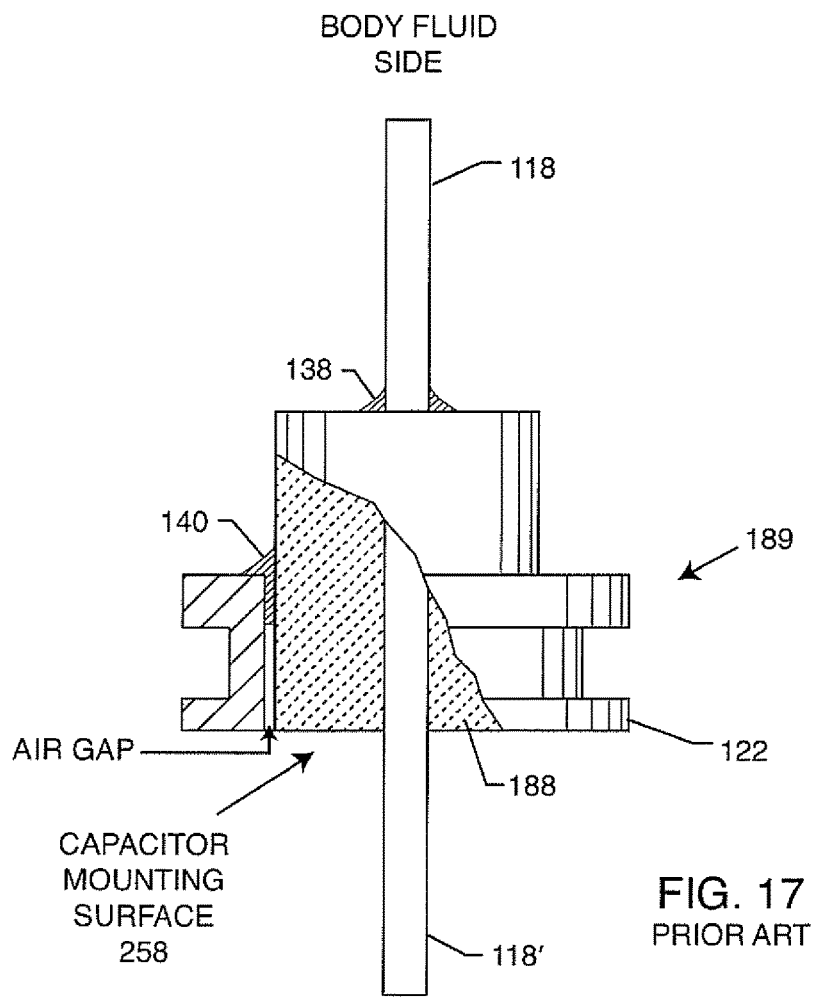
FIG. 17 illustrates a cross-sectional view of a unipolar unfiltered hermetic seal.
Figure 18:
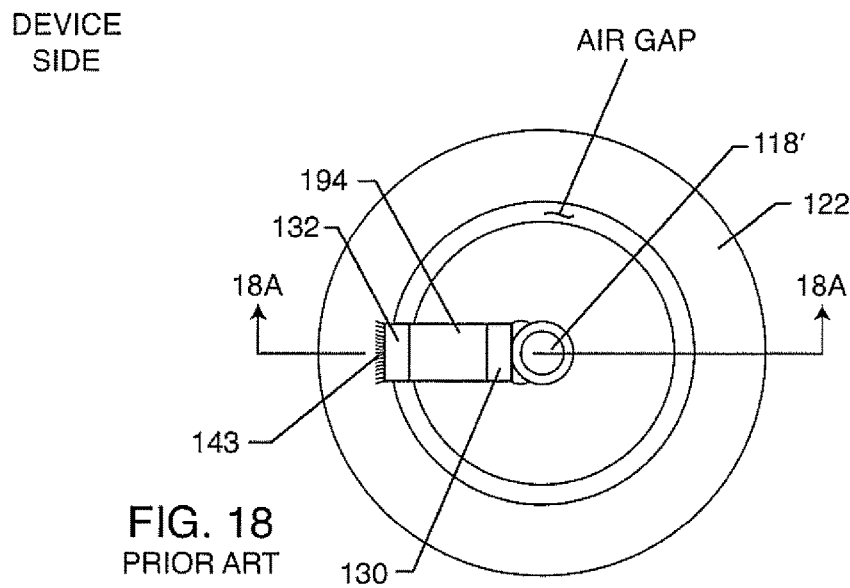
FIG. 18 illustrates application of an MLCC chip capacitors attached directly to an oxidized ferrule of an AIMD.

FIGS. 16, 17 and 18 illustrate prior applications of MLCC chip capacitors 194 attached to hermetic seal subassemblies of active implantable medical devices. These patents include: U.S. Pat. Nos. 5,650,759; 5,896,267; 5,959,829 and 5,973,906, the contents of which are fully incorporated herein by reference. Referring once again to FIG. 16, the electrical connection between MLCC chip capacitor ground termination 132 and circuit trace 147 is generally oxide-resistant; however, the attachment of the ground circuit trace 147 to the oxidized ferrule 122, which can become an electrical resistance problem. As previously described in the prior art, an undesirable increased resistance due to oxide thickening can seriously, even dangerously, degrade MLCC chip capacitor filter performance.

Referring once again to FIG. 17, one can see that there is a hermetic seal insulator 120,188 disposed within a ferrule 122. In FIG. 17, the insulator 120,188 is hermetically sealed by a gold braze 140 between the insulator 120,188 and ferrule 122. There is also a leadwire 118, having body fluid side lead end 118 and device side lead end 118'. Leadwire 118 is continuous from the body fluid side to the device side. There is also a hermetic seal gold braze 138, which hermetically seals the leadwire 118 to the insulator 120,188. Throughout this specification, it is understood that the insulator 120,188 is sometimes single-numbered as 120, sometimes single-numbered as 188 or in some cases, is labeled 120,188. It will also be appreciated that the gold braze insulator is typically of a high purity alumina ceramic. It is also appreciated that the insulator can include a glass or a glass-ceramic hermetic seal in which case, the gold brazes 138 and 140 are not necessary (therefore, there are no hermetic seal gold brazes for an oxide-free EMI filter system ground connection).

Referring once again to FIG. 18, the left-hand side of the MLCC chip capacitor 194 is electrically connected 143 directly to the potentially oxidized ferrule 122. As was just described for feedthrough capacitors, this is also very poor practice which can lead to undesirable resistance in series with the capacitor filter 194.

Figure 18A:
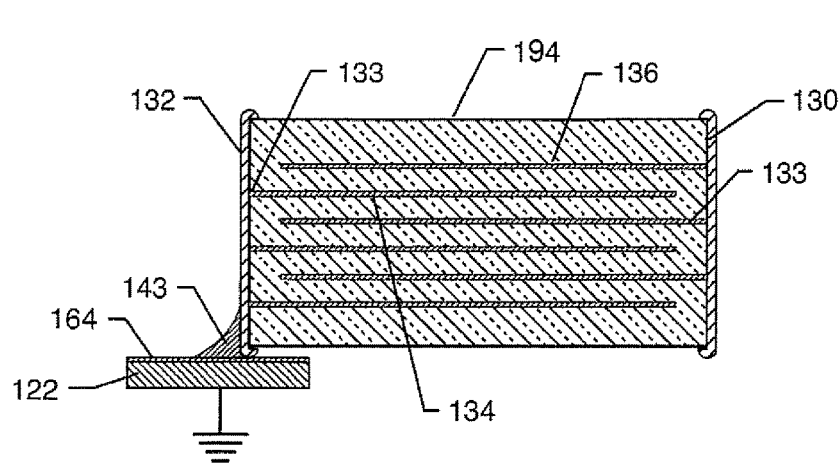
FIG. 18A illustrates a cross-section of the MLCC chip capacitor of FIG. 18, illustrating the elements that give rise to undesirable series resistance.

FIG. 18A is a sectional view taken from section 18A-18A from FIG. 18, which shows the MLCC chip capacitor 194 ground electrode plates 134 and active electrode plates 136. It is appreciated that this symmetrical capacitor can be reversed thereby reversing the ground and active electrode plates. The MLCC chip capacitor has capacitor termination materials 132, as indicated, which are electrically connected using electrical connection material 143 directly to the ferrule 122. One can see the undesirable surface oxide 164 that can form during laser welding of the ferrule 122 and the device housing 102 as previously disclosed. The schematic diagram of FIG. 18A shows undesirable resistance R, which is a result of this undesirable surface oxide 164. As previously described, the dielectric loss is also a series resistance, but at high frequency, the series resistance will essentially go away.

Figure 18B:
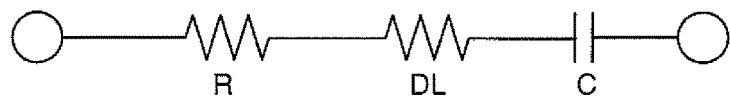
FIG. 18B gives the equations for capacitive reactance and the capacitor's impedance of FIG. 18.

FIG. 18B gives the equations for capacitive reactance and also for impedance. ESR can undesirably increase the filter capacitor's impedance, which is preferably as low as possible.

Figure 18C:
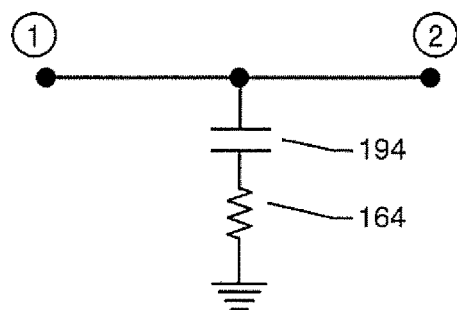
FIG. 18C is the electrical schematic of the capacitor of FIG. 18 showing the undesirable series resistance that forms from the undesirable series resistance that forms from titanium oxides.

FIG. 18C further illustrates that the ohmic loss resistance due to surface oxides 164 appear in series with the filter capacitor and system ground 144. This resistance is highly undesirable because it degrades filter performance.

Figure 19:
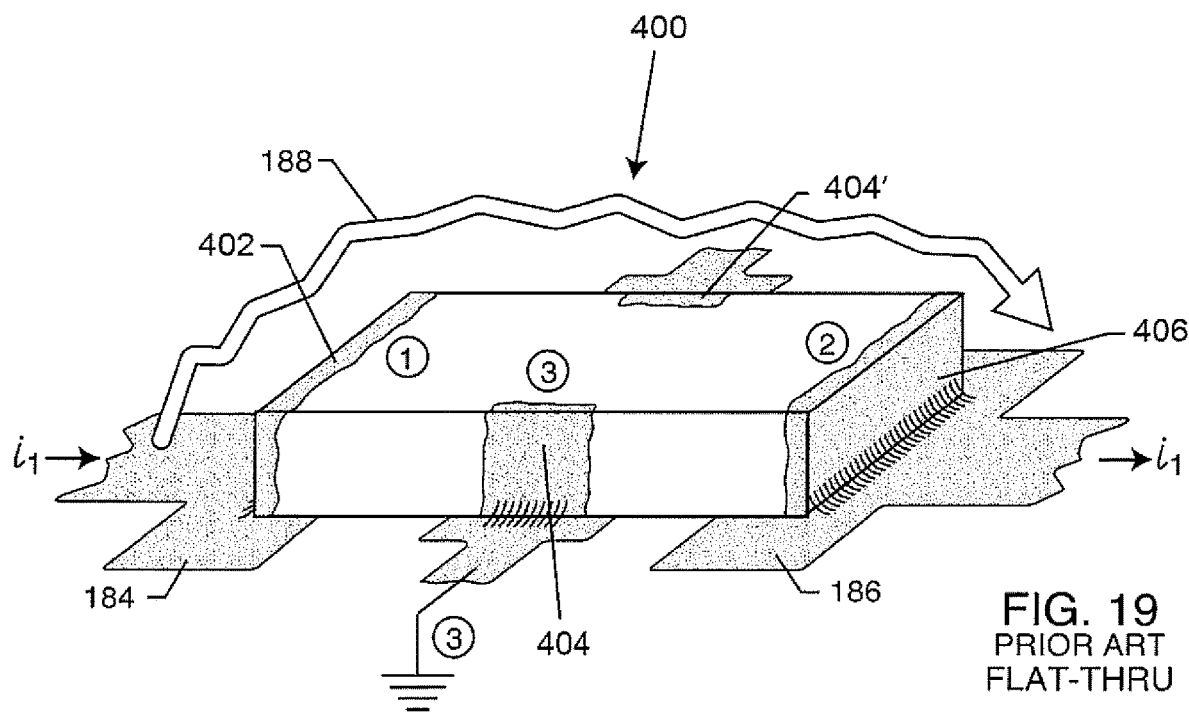
FIG. 19 illustrates a prior art flat-thru capacitor.
Figure 20:
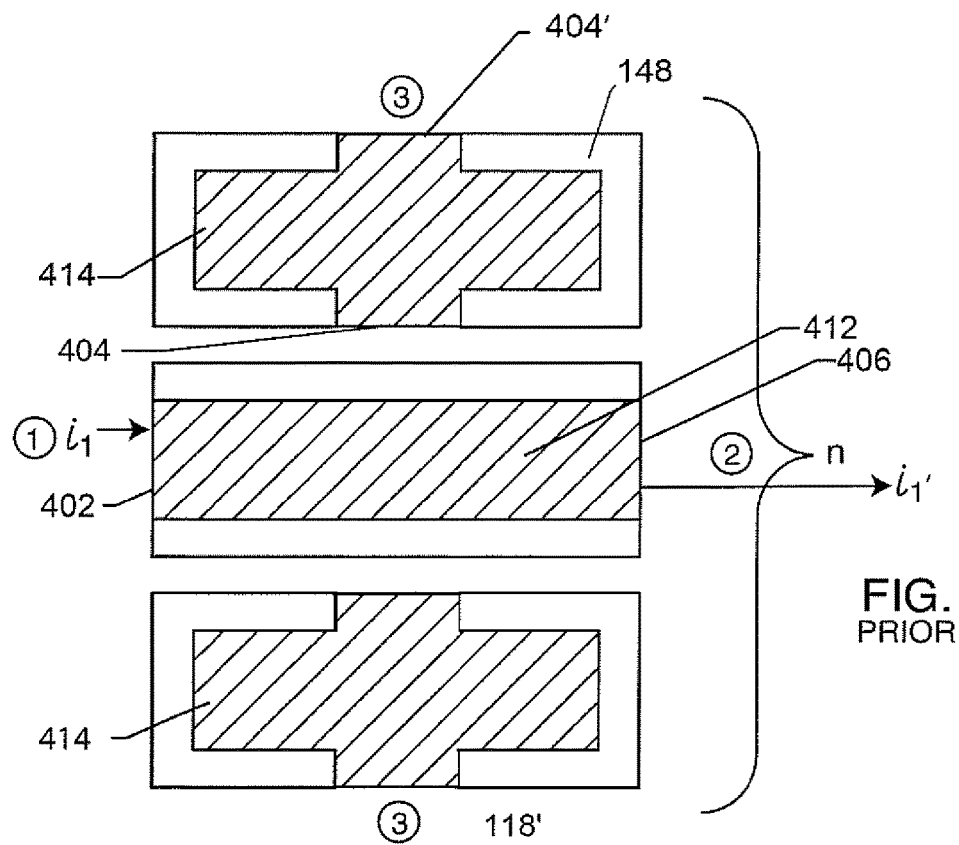
FIG. 20 is a multiple sectional view of the electrode plate stack-up of the structure of FIG. 19.

FIG. 19 illustrates a prior art flat-thru capacitor 400. This is better understood by referring to its internal electrode plates as illustrated in FIG. 20. The flat-thru capacitor of FIG. 19 is also known as a three-terminal capacitor because there is a circuit current $i_1$ that passes through its active electrode plate 412 from the first terminal 184 to the second terminal 186. If there is a high frequency electromagnetic interference signal being conducted along this active electrode plate 412, then this electromagnetic interference is diverted through filter capacitance action to system ground at terminal 3. Referring back to FIG. 19, there is a general disadvantage to such capacitors in that, at very high frequency, EMI 188 can cross-couple from the left side of the MLCC chip capacitor to the right side of the MLCC chip capacitor.

Referring once again to FIG. 19, one can see a connection to system ground 144 (ground symbol), which is essential for proper filter performance. As previously described, it is important that this system ground connection be essentially free of undesirable surface oxides.

FIG. 20 illustrates the ground and active electrode plates of the flat-thru capacitor 400 of FIG. 19. The ground electrode plates are 414 and the active electrode plate is 412. These electrode plates are stacked in interleaved relationship forming the flat-thru capacitor. As shown, the circuit current $i_1$ passes through the active electrode plate 412. There is an advantage to this in that any inductance along the length of the plate appears in series with any EMI thereby improving filter efficiency. A downside of having the current pass through the active electrode plate 412 is the limited current handling capability of the flat-thru capacitor active electrode plates. Flat-thru capacitors, as illustrated in FIGS. 19 and 20, are acceptable for most active implantable medical device applications; however, this configuration is highly unlikely for an implantable defibrillator, wherein a very high current, high voltage shock must be delivered. The cross-sectional area of an electrode plate 412 of a monolithic ceramic capacitor is generally limited in cross-sectional area.

Figure 21:
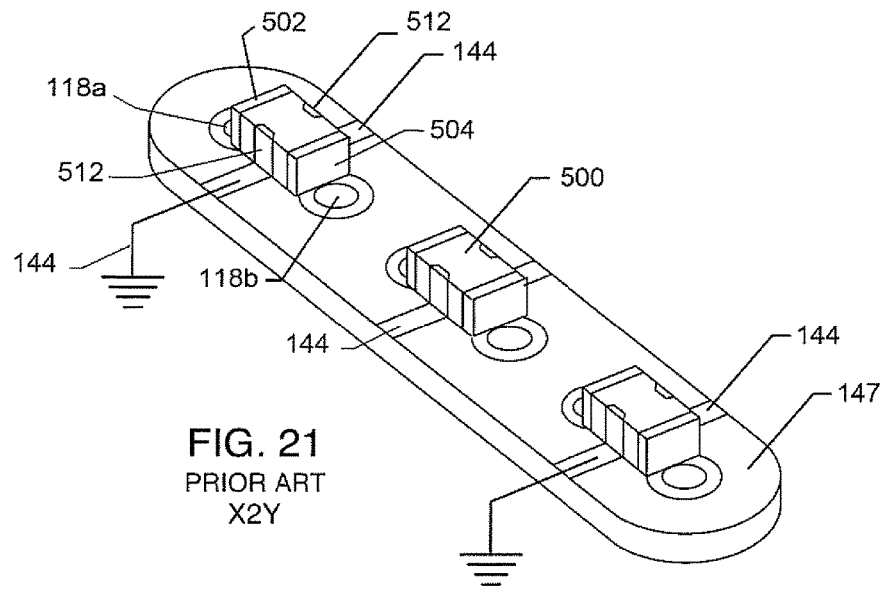
FIG. 21 illustrates a three-terminal capacitor that is also known in the industry as X2Y attenuator.

FIG. 21 also illustrates three X2Y attenuators 500 mounted on a circuit board 147 that is designed to be placed adjacent to the device side of an insulator and/or a ferrule of an AIMD hermetic seal subassembly. These X2Y attenuators are bipolar, meaning that each pair of X2Y attenuators filters two active leadwires, as shown. The X2Y attenuators have two active terminations 502 and 504 as shown. The X2Y attenuators also have ground terminations 512 that must be electrically connected to system ground.

Figure 22:
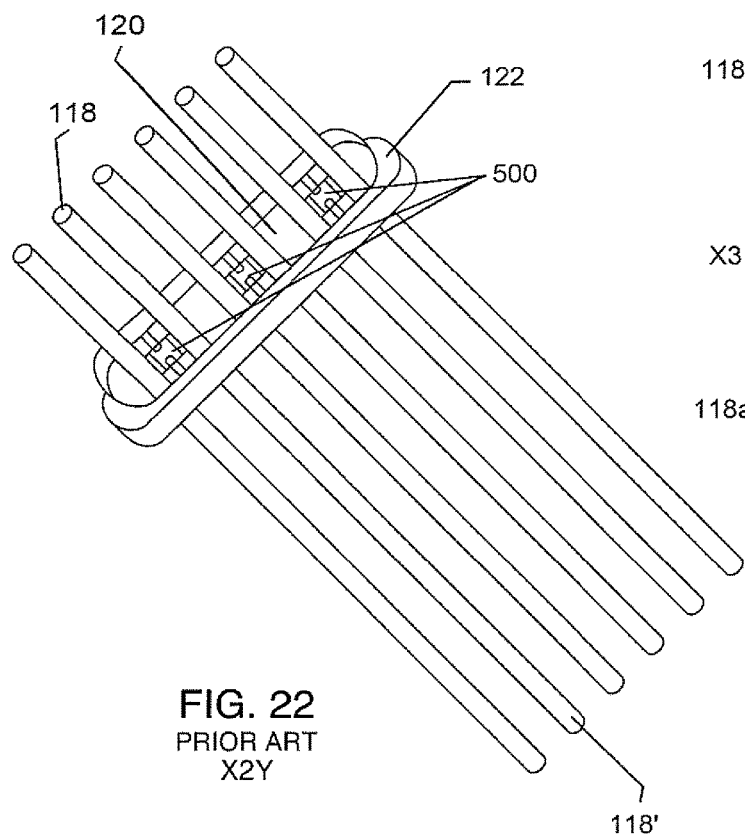
FIG. 22 illustrates a three-terminal capacitor that is also known in the industry as X2Y attenuator.

FIG. 22 illustrates the three X2Y attenuators of FIG. 21 mounted on the device side of insulator 120 and in a pocket of the ferrule 122.

Figure 22A:
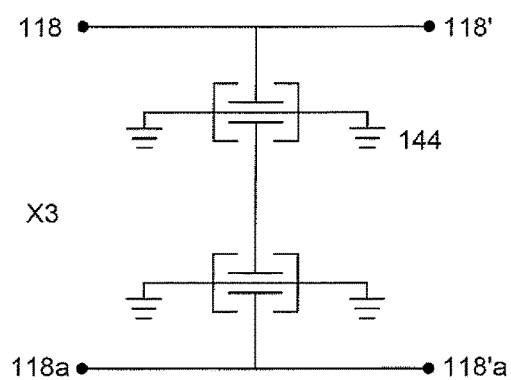
FIG. 22A illustrates an electrical schematic of the three-terminal capacitors of FIGS. 21 and 22.

FIG. 22A is a schematic diagram that illustrates each one of the X2Y attenuators. The X3 next to the schematic indicates that there are three of these bipolar X2Y attenuators. Referring once again to FIG. 22A, one can see that this X2Y attenuator 500 is disposed between adjacent active leadwires One can see that there is line-to-ground capacitance between adjacent active leadwires 118 and also from each active leadwire to system ground. The X2Y attenuator forms line-to-line capacitance through the series capacitances between adjacent active leadwires 118 From an electromagnetic interference (EMI) perspective, the line-to-ground capacitance is useful for diverting differential-mode EMI, and the line-to-line capacitance is useful for attenuating differential-mode EMI. An example of differential-mode EMI is an EMI signal that produces a voltage when measured adjacent leadwire to leadwire 118. This differential voltage is best measured without the X2Y filter 500 present. By careful design of the X2Y attenuator internal electrode plates, one can control the amount of capacitance to ground and also the amount of line-to-line capacitance. The electrical schematic of FIG. 22A assumes that the ground electrical connections are to a non-oxidized ferrule 122 surface, such as the gold braze 138 that is formed between the ferrule 122 and the hermetic seal insulator 120. This is why there is no resistance shown in the system ground connections of FIG. 22A.

Figure 23:
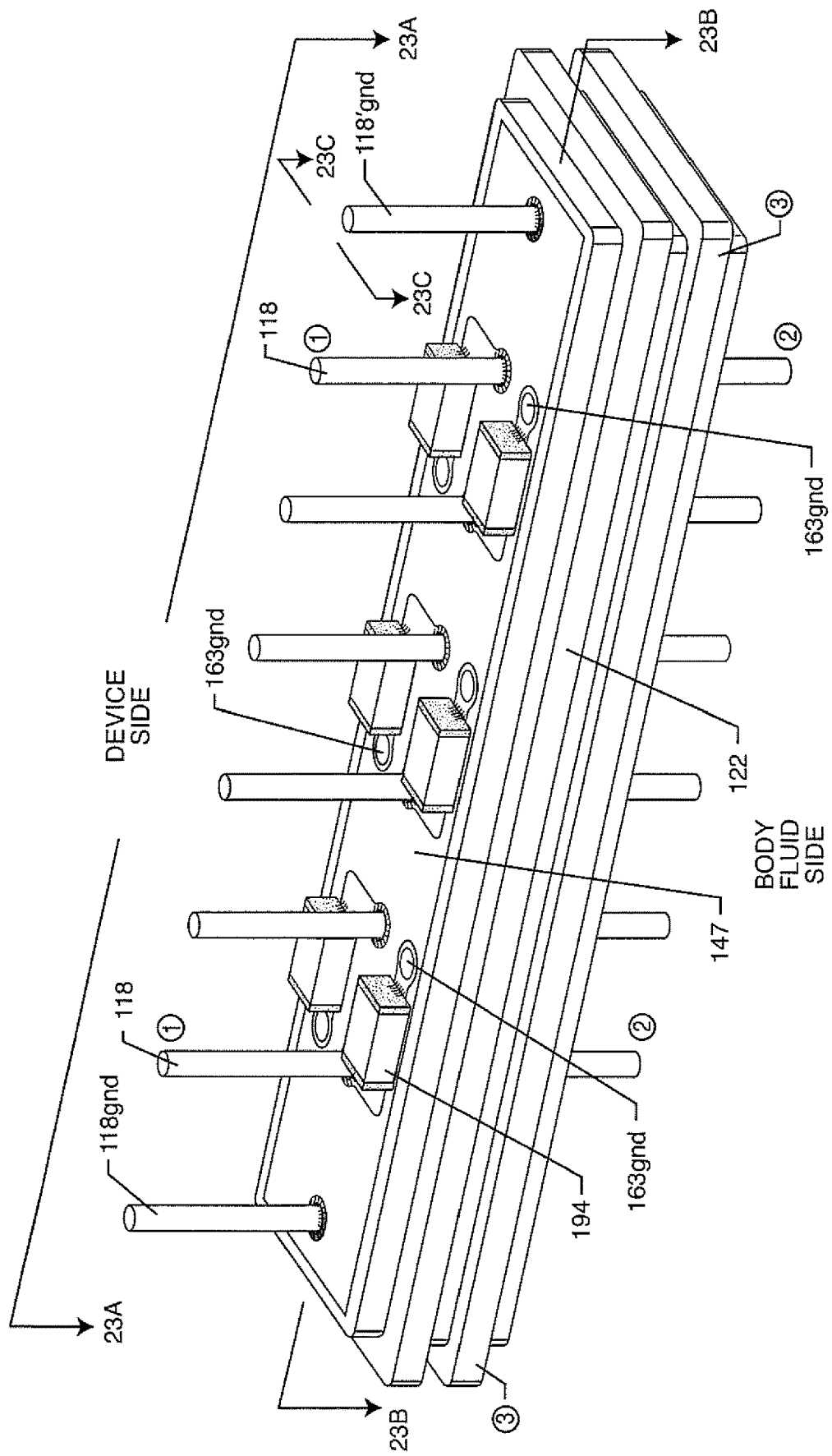
FIG. 23 is a perspective view of a prior art MLCC filter circuit board attached to the ferrule for an AIMD.

FIG. 23 illustrates a prior art filtered hermetic seal assembly. In this case, there is an MLCC filter circuit board 147. Disposed on the circuit board are six MLCC chip capacitors 194. Accordingly, the MLCC filter circuit board is disposed on a hermetic seal of an AIMD that has six active poles or leadwires. The leadwires on the left end and the right end are labeled 118gnd. As will be explained, these pins are electrically and mechanically connected to the ferrule 122, each pin providing a ground connection to internal circuit board ground plates (not shown). As will be disclosed, these circuit board ground plates are extremely important so that EMI is reflected similarly to prior art feedthrough filter capacitors.

FIG. 23A is taken from section 23A-23A from FIG. 23. This is the top view of the circuit board of FIG. 23 showing the top view of the MLCC chip capacitors 194a through 194f.

FIG. 23B is taken from section 23B-23B from FIG. 23 illustrating at least one internal circuit board ground plate 161 embedded within the circuit board. The at least one internal circuit board ground plate 161 is electrically connected to system ground 144 through the two ground pins 118'gnd that are electrically connected to the ferrule. The at least one internal circuit board ground plate 161 comprises ground via holes 163a through 163e that provide a ground electrical connection to each of the six MLCC chip capacitors 194. Referring once again to FIG. 23A, one can see that there are circuit board via holes 163 electrically connected to the ground metallization 130 of each of the MLCC chip capacitors 194. An optional circuit trace is shown between the ground via holes 163 and the MLCC chip capacitor ground termination 130. It is appreciated that the ground connection to the MLCC chip capacitor ground termination 130 can be a direct electrical connection to the circuit board via hole or through a circuit board circuit trace as shown. For optimal filter performance, the circuit trace length is as short as possible to minimize series inductance. Referring once again to FIG. 23B, one can see that the hermetic seal active leadwires 118' pass through the circuit board ground plate 161 in non-conductive relation. The embedded or exterior circuit board ground plate 161 can consist of a multiplicity of ground plates and including a ground plate preferentially disposed between the circuit board and the hermetic seal insulator 120. This relatively wide set of one or more circuit board ground plates 161 provides a very low inductance path to divert EMI from the active leads 118 to system ground 144. In addition, the one or more circuit board ground plates 161 effectively reflect or absorb radiated electromagnetic fields thereby preventing direct entry of EMI into the interior (device side) of the AIMD housing. This reflection and absorption of incident fields is very important at high frequencies, for example, those in the frequency range of cellular telephones and other wireless communicators from approximately 300 MHz to 3000 MHz.

Figure 23C:
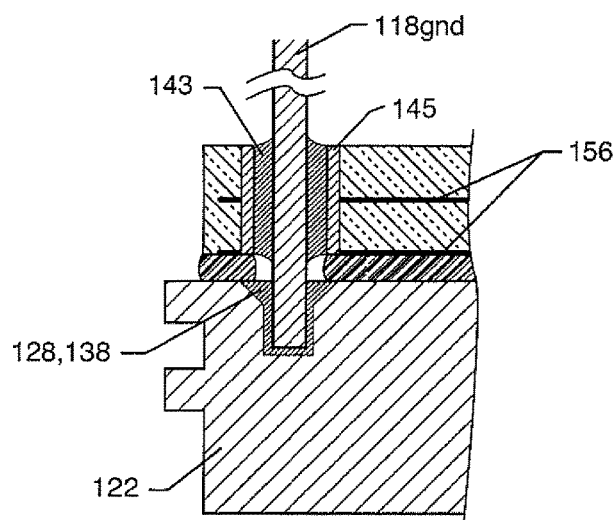
FIG. 23C is taken from section 23C-23C from FIG. 23 illustrating an oxide-resistant circuit board ground pin.

FIG. 23C is a cross-sectional view taken from 23C-23C of FIG. 23 illustrating an embodiment of the ferrule ground pin 118gnd. The ground pin 118gnd is shown electrically and mechanically connected to the ferrule 122 by either a laser weld 128 or a gold braze 138. Ideally, ground pin 118gnd is of an oxide-resistant material, such as, but not limited to, platinum. This makes for an essentially oxide-free electrical connection 143 to the circuit board internal ground plates 156. In this case, there are two circuit board ground plates: an internal circuit board ground plate, which is embedded in the circuit board, and an external circuit board ground plate, which is disposed on the bottom of the circuit board. It is understood that, while two circuit board ground plates are illustrated in FIG. 23C, the circuit board may have one circuit board ground plate, which can be disposed either internal or external of the circuit board. it is also understood that there may be a multiplicity of embedded internal ground plates either in combination with at least one external circuit board ground plate or without any external circuit board ground plates. Any circuit ground plate may alternatively be a circuit trace. Referring once again to FIG. 23C, one will see that there is a circuit board via hole, which has a via hole metallization 145 that is spatially aligned over the ground pin 118gnd. Throughout the present invention, via holes are provided with some sort of a conductive or metallization layer on the inside diameters. It is understood by one skilled in the art that the inside diameter of circuit board via holes can be metal eyelets, plated, metallized, or the like. In each case, conductive or metallization layer of the via hole is electrically connected to one or more internal or external circuit board ground plates or circuit traces. In the case of FIG. 23C, the circuit board metallization 145 makes electrical contact to the one internal and the one external circuit board ground plates 156 as illustrated.

Figure 23D:
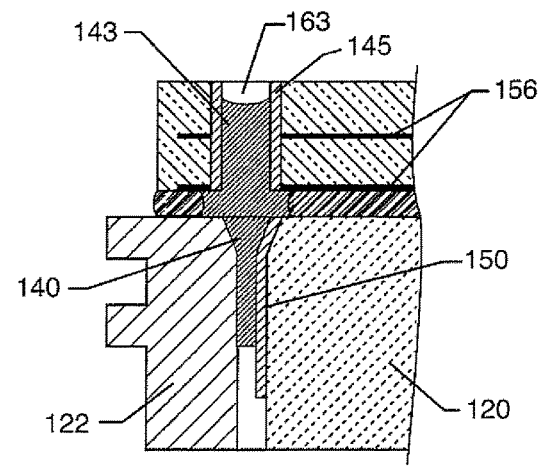
FIG. 23D illustrates that the ground pin of FIG. 23C can be replaced by a spatially aligned ground via over the hermetic seal to ferrule gold braze.

FIG. 23D illustrates an alternative embodiment of grounding circuit board ground plates 156. In this case, a circuit board ground via hole 163 is spatially aligned over the gold braze 140 that forms a hermetic seal between the insulator 120 and the ferrule 122 of the hermetic seal. By spatially aligning the ground via hole over the gold braze 140, one can then make an essentially oxide-free electrical connection directly to the hermetic seal gold braze using electrical connection material 143, as shown. Electrical connection material 143 can be a solder, a thermal-setting conductive adhesive or the like. Referring once again to FIG. 23D, illustrated is a metallization layer 150 disposed on the perimeter wall of the insulator 120. The metallization layer 150 is, generally, an adhesion/wetting layer that, during the brazing process, facilitates the flow of the gold braze 140. An electrical connection to the gold braze hermetically sealing the insulator and the ferrule provides a reliable low resistance, low impedance and stable ground connection. Electrical connection to the hermetic seal gold braze 140 additionally provides a very low and reliable stable resistance for the circuit board system ground path.

Figure 23E:
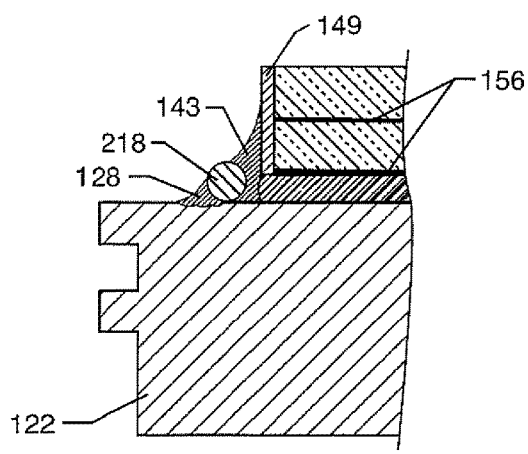
FIG. 23E illustrates that the circuit board of FIG. 23 may have an edge metallization that is attached to a metal addition, which is laser welded or gold brazed to the AIMD ferrule.

FIG. 23E shows that an oxide-free electrical connection to the circuit board ground plates 156 can also be achieved by an oxide-resistant metal addition 218, which is either gold brazed, or laser welded 128 to the ferrule 122. Typically, this metal addition is of an oxide-resistant material, such as platinum.

Figure 23F:
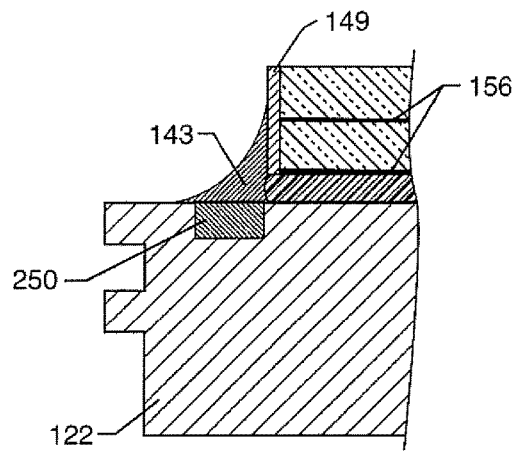
FIG. 23F illustrates that the FIG. 23 circuit board can have a ground edge metallization that is connected to a gold pocket-pad, which is formed into a recess in the AIMD ferrule.

FIG. 23F illustrates another method of forming an oxide-resistant electrical connection 143 from the circuit board ground plates 156 to the ferrule 122. In this case, there is a gold pocket-pad 250, which acts like a swimming pool moat into which gold braze or equivalent materials are formed. This forms an oxide-resistant electrical connection between the ferrule 122 and the circuit board ground edge metallization 149 and in turn, to the circuit board ground plates 156.

Figure 23G:
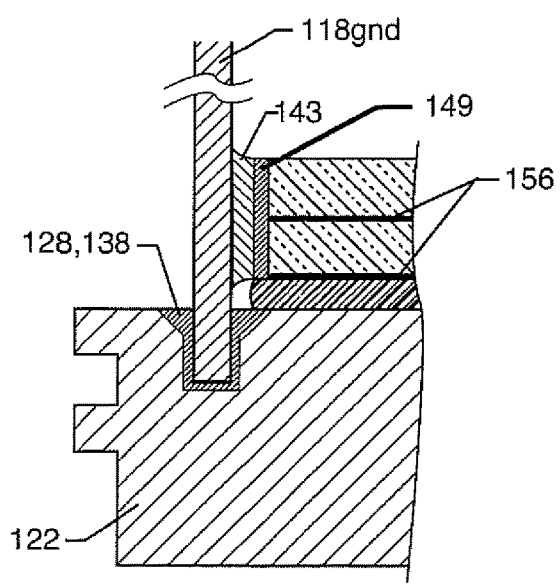
FIG. 23G illustrates that circuit board may have an edge ground metallization that is conductively coupled to an oxide-resistant ground pin described in FIG. 23C.

FIG. 23G is similar to FIG. 23C in that there is an oxide-resistant ground pin 118gnd, which is electrically and mechanically connected to the ferrule 122 by a laser weld 128 or a gold braze 138. In this case, instead of grounding through a via hole, as illustrated in FIG. 23C, there is an electrical connection 143 from a circuit board ground edge metallization 149 directly to the oxide-resistant ground pin 118gnd. Accordingly, this provides a very low resistance (low ESR) grounding path to system ground 144. As previously defined, system ground 144 is the AIMD housing 102 and is also equivalent to the system ground 144 provided by the ferrule 122. Importantly, circuit board ground plates 156 provide a low impedance path for the filters (an MLCC chip capacitor 154, an X2Y attenuator 300, a flat-thru capacitor 400, and combinations thereof) to divert dangerous EMI currents while at the same time, shielding the insulator 120 from direct penetration of high frequency RE-radiated noise (EMI). Referring again to FIGS. 23C-23H, the circuit board ground plates 156 can also be called circuit board ground shield plates. In other words, the ground plates 156 not only provide a low impedance filter circuit diversion pathway to system ground, but also shield against radiated EMI. Referring once again to FIG. 23C, one can see that the radiated EMI is reflected off filter ground electrodes. Circuit board shield plates or ground plates act in identical manner. Not shown is that these plates also absorb incident RF energy and that the capacitive action of the filter diverts the RF energy to the AIMD housing 102, where it is harmlessly dissipated as a few milliwatts of heat energy. This diversion prevents the EMI from dangerously reaching the inside of the AIMD shielded housing 102, as illustrated in FIG. 23A.

Figure 23H:
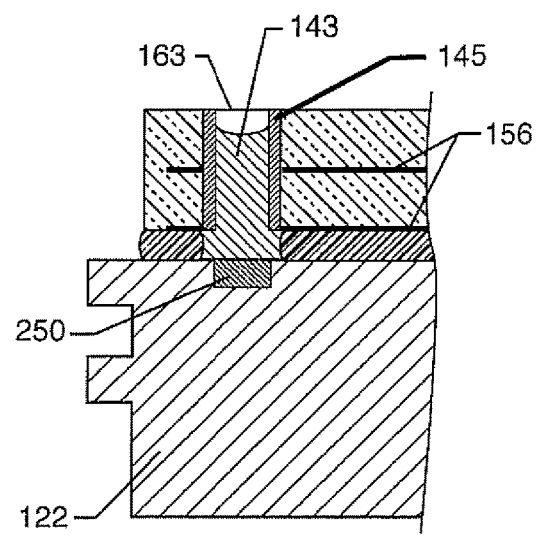
FIG. 23H is similar to FIG. 23G, except that the ground via hole is spatially aligned over a gold pocket-pad formed in a ferrule recess.
Figure 23:
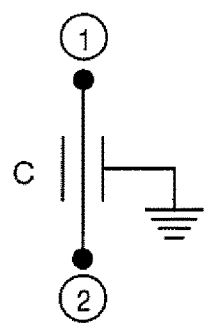

FIG. 23H is very similar to FIG. 23F in that an oxide-resistant gold bond pad 250 has been provided in a ferrule pocket. In this case, a circuit board ground via hole 163 has been spatially aligned over the gold pocket-pad 250, such that an electrical connection 143 is made to the oxide-resistant noble gold filling the pocket. In this way, circuit board ground plates 156 have a very low resistance connection to system ground 144, which is ferrule ground 122. Gold pocket-pads are disclosed in U.S. Pat. No. 10,350,421, the contents of which are incorporated fully herein by this reference. Gold pocket-pads may comprise other oxide-resistant materials such as platinum. Noble metals, such as gold and platinum, are used as jewelry for this reason, as gold and platinum do not tarnish or oxidize over time. The pocket-pad 508 may comprise a number of other oxide-resistant materials, such as gold, gold alloys, rhodium, rhodium alloys, platinum, platinum alloys, platinum-iridium alloys, palladium, palladium alloys, nitinol, cobalt-chromium alloys and combinations thereof. A potential disadvantage of the gold pocket-pad as illustrated in FIG. 23H is the cost of forming the swimming pool-like pocket in the ferrule 122 and the cost of a substantially large quantity of gold or other suitable material, which is disposed and subsequently re-flowed (typically in a high temperature vacuum gold braze furnace) in the pocket-pad.

FIG. 23I illustrates the schematic diagram for FIG. 23 showing that both the inductance and the resistance are minimized such that an ideal capacitor having trivial series resistance R is formed, which results because $R_{OXIDE}$ has been eliminated. In summary, the embodiments of FIGS. 23A through 23H disclose that an oxide-resistant or oxide-free electrical connection can be formed, therefore, there is no need for a resistor symbol R in the schematic of FIG. 23I.

Figure 24:
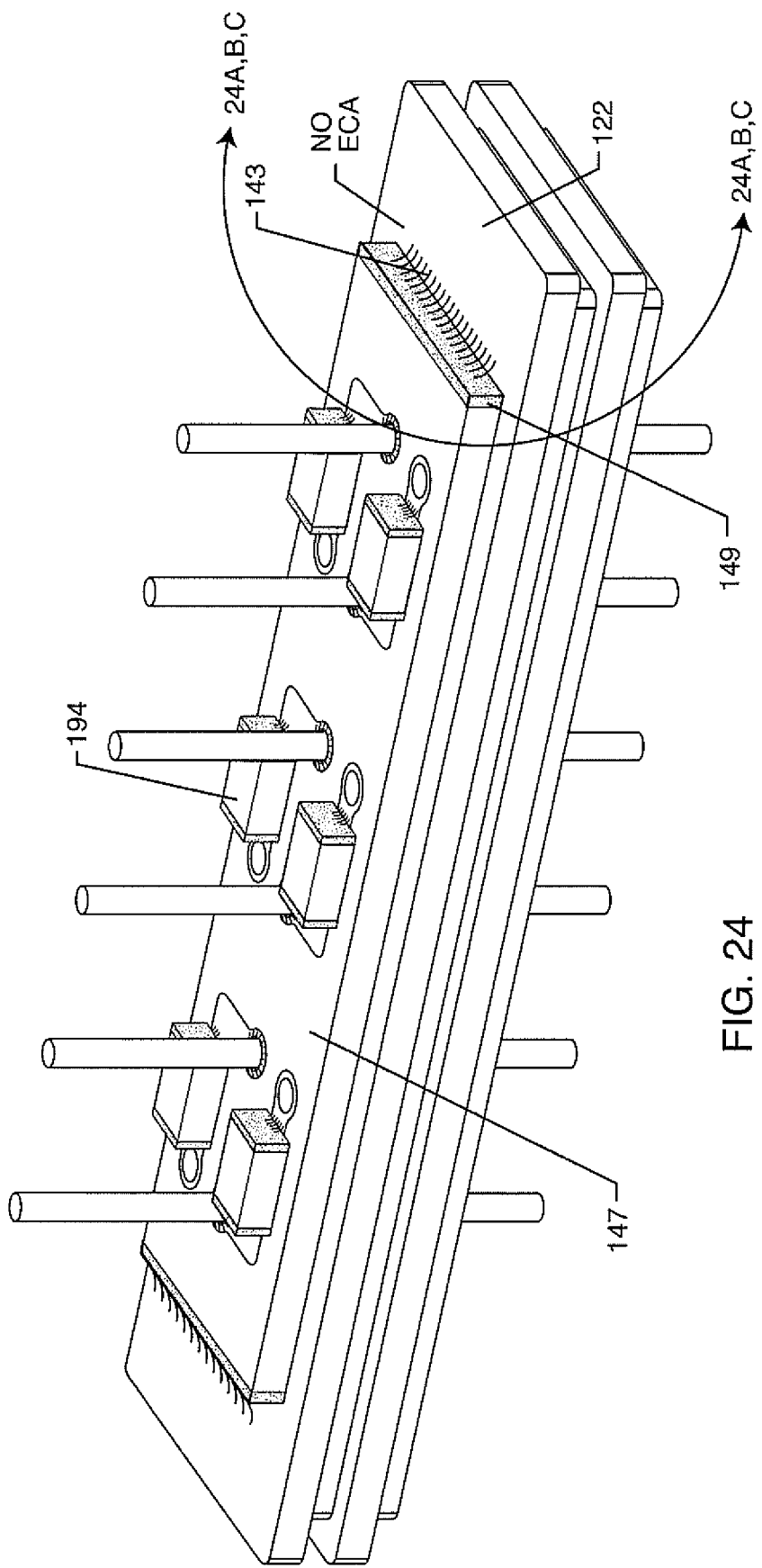
FIG. 24 illustrates the circuit board of FIG. 23 having a ground edge metallization, which is undesirably connected to an oxidized AIMD ferrule (poor practice)

FIG. 24 is similar to FIG. 23, except that FIG. 24 illustrates a prior art circuit board 147 having circuit board ground edge metallizations 149 electrically connected to circuit board ground plates (not shown), which are directly electrically connected 143 to the ferrule 122. Such direct electrical connection to the ferrule 122, as illustrated, is extremely poor practice. As previously described, the surface of a titanium ferrule is prone to the formation of resistive or semi-conductive oxidation layers, which can significantly, even dangerously, reduce EMI filter performance. All of the same concepts as previously taught herein for feedthrough capacitors, apply to filter circuit boards, including the filter circuit board of FIG. 24. As previously described, oxide removal by mechanical or acid etching of the titanium ferrule 122 is only temporary, as oxides will almost immediately reform. These oxides form very quickly at elevated temperatures, such as the high temperatures created by laser welding 128 the ferrule 122 into an opening in an AIMD housing 102 (not shown).

Figure 24A:
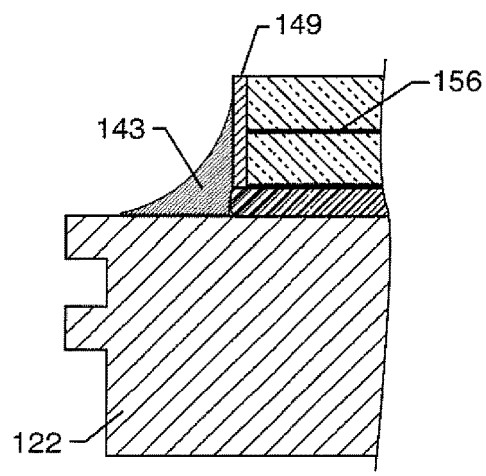
FIG. 24A is taken from section 24A-24A from FIG. 24 and illustrates the direct electrical connection to the oxidized ferrule.

FIG. 24A is taken from section 24A-24A from FIG. 24 illustrating that the ground electrical connection material 143 is disposed on the circuit board ground edge metallization 149 and directly on the surface of the ferrule 122, which, as previously disclosed, is not good practice. For simplicity, FIG. 24A does not show an oxide layer; however, the inventors of the present application have reproducibly demonstrated that even curing a thermal-setting conductive adhesive 143 in a vacuum (a hard vacuum, which is a very difficult process) in an attempt to prevent the titanium ferrule 122 from reforming any oxides proved futile. A reproducible, stable and oxide-free connection was just not achievable. It is further noted that the electrical connection 143, as illustrated in FIG. 24A, cannot even be made using a solder, since a titanium ferrule 122 is not solderable because solders do not wet to titanium.

Figure 24B:
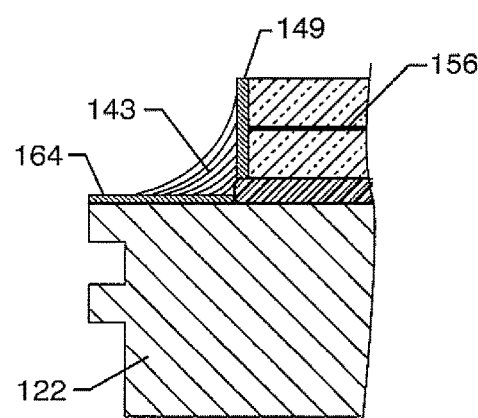
FIG. 24B illustrates undesirable oxidize build up over time and temperature.

FIG. 24B is taken from section 24B-24B from FIG. 24 and illustrates the undesirable formation of an oxide layer 164 on the surface of a ferrule 122. It is appreciated, that the surface oxide layer 164 would generally occur over all surfaces of the ferrule but is only shown on the top for simplicity. As previously discussed, the surface oxide layer 164 greatly increases the resistance or equivalent series resistance (ESR) to the circuit board ground plates 156 and then in turn, to the MLCC chip capacitors 194 (not shown). Referring once again to FIG. 24A, the surface oxide layer 164, shown in FIG. 24B, formed or re-formed or both underneath the electrical connection 143, in other words, between the electrical connection material 143 and the previously cleaned ferrule 122. As previously described, the electrical connection material 143, is a thermal-setting conductive adhesive, including conductive polyimides, conductive polymers and conductive epoxies. The surface oxide layer 164 can be present at the time electrical connection material 143 is applied or the surface oxide layer can form over time (later) between the ferrule and electrical connection material 143, particularly during laser welding 128 of the ferrule 122 to the AIMD casing 102. When conducting a laser weld 128, substantial localized heat may be generated, which can accelerate surface oxide layer 164 formation.

It is incorrectly believed by some that surface oxide layer 164 will not form on titanium components internal to the AIMD casing 32 once the AIMD casing is hermetically sealed, because the area inside of an AIMD housing is generally evacuated with a vacuum and then backfilled with inert gas, such as helium, nitrogen or argon, with the intention of eliminating moisture. The belief that vacuum evacuation and back-filling with inert gas will inhibit oxidation of sensitive materials like titanium is erroneous. Materials of construction used in the manufacture of AIMDs, such as polymers, plastics, adhesives, elastomers and the like, and even the printed circuit boards (PCBs) themselves, generally have some level of gases trapped within their structure; for example, moisture, oxygen, other oxygen-containing gases, or even undetected residues comprising the same, which eventually outgas during the operating life of the device. Furthermore, processes that do involve increased temperature, like welding, curing or other temperature shifts, actually accelerate such outgassing. Hence, even if an AIMD is manufactured in an inert gas environment, or backfilled with an inert gas, such 'heating' of certain materials of construction can release oxygen, oxygen-containing gases or water vapor into an otherwise hermetically sealed environment, causing the formation of surface oxide layers 164 on otherwise conductive titanium surfaces 102, 122. It is extremely important that no undesirable surface oxides form in the system ground connection to any EMI filter. It is also important during a qualification and during production, that filter performance metrics be measured. These filter performance metrics must include: Equivalent Series Resistance (ESR) above 10 MHz and, in particular, at 64 MHz (MRI RF pulsed frequency of a 1.5T scanner), and insertion loss (IL) sweeps in dB on a network analyzer from 10 MHz to 3000 MHz, including 64 MHz (1.5T MRI scanner) and 128 MHz (3T MRI scanner). For more detail referring the effects of oxide layer formation on EMI filtering, refer to the paper entitled, "Dissipation Factor Testing is Inadequate for Medical Implant EMI Filters and Other High Frequency MLCC Capacitor Applications", ISSN: 0887-7491, presented at CARTS 2003: 23rd Capacitor and Resistor Technology Symposium, Mar. 31-Apr. 3, 2003, incorporated herein by this reference. In summary, the presence of a surface oxide layer 164 can seriously degrade EMI filter performance (in dB), particularly at high frequencies or at MRI RF-pulsed frequencies, where the diverter filters must bypass a substantial amount of high frequency current. Accordingly, the inventors have found that the non-oxide-resistant electrical ground connection, such as illustrated in FIGS. 27A, 27B, and 27C are a highly undesirable approach.

Figure 24C:
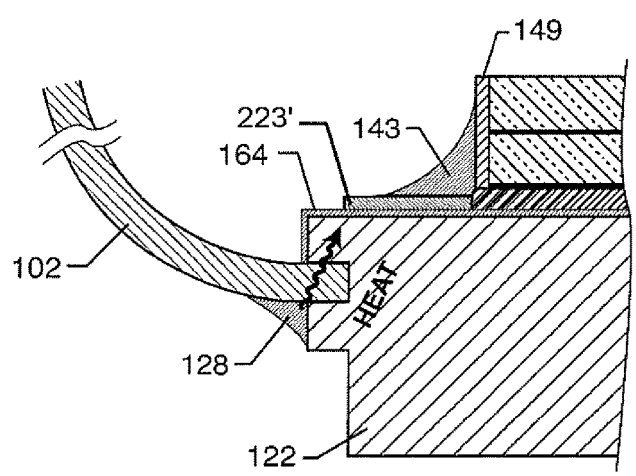
FIG. 24C illustrates a highly oxidized ground connection that occurs after laser welding of the ferrule and the opening in the AIMD titanium housing.

FIG. 24C is taken from section 24C-24C from FIG. 24 and illustrates the heat that is formed during laser welding 128 of the ferrule 122 into an opening of the AIMD housing 102. This heat undesirably does two things: 1) it heats up the electrical connection material 143, which is typically a thermal-setting conductive adhesive. This heating of the polymer releases free oxygen which then becomes available to form a thicker surface oxide 164. As shown, a surface oxide layer forms all over the inside of the housing. As previously discussed, titanium oxide formations are accelerated by elevated temperature. Referring once again to FIGS. 248 and 24C, the surface oxide layer 164 may comprise several layers, with any one or more layers further comprising one or more titanium oxide compositions. As mentioned, these surface oxide layers 164 are undesirably insulative and can also cause potentially undesirable semiconductor behavior. One approach that the inventors have tried in the past is to clean the oxide layers 164 from the ferrule 122 device side surface using abrasive mechanical and chemical removal processes, including grit-blasting, mechanical grinding, sanding, and hydrofluoric acid cleaning. It should be noted that titanium oxides, once formed, are very stable and very hard to remove. Titanium oxides are so stable that they are commonly used as paint pigments. Referring once again to FIG. 24A, the inventors first cleaned the oxide layers 164 from the device side ferrule 122 surface and then formed a stripe or a coating of an electrically conductive adhesive (ECA stripe 223'). The ECA stripe 223' comprised a thermal-setting conductive polyimide. During this experiment, there was no oxide-resistant sputter layer 165, in accordance with the present invention. In other words, the ECA stripe 223' was directly applied to the titanium surface 122. The inventors then connected the ground metallization of feedthrough filter capacitors 124 directly to the ECA stripe 223' with electrical connection material 148, 143. This seemed to work very well in high frequency electrical measurements, including insertion loss (IL), impedance, ESR and inductance, all initially measuring very low and within acceptable specification limits. However, as previously described in FIGS. 60, 6E and 6F, out of a prototype qualification lot of a thousand pieces evaluated, five (post laser welding) parts exhibited higher resistances and impedances, thus failed qualification testing. Graphs of ESR vs. frequency sweeps of three of these five failures are shown in FIGS. 6D, 6E and 6F which alarmingly and dangerously show elevated high frequency resistance due to oxide formation, particularly at 100 MHz. This high of a failure rate (0.5%) for life sustaining devices like implantable cardiac pacemakers and ICDs is unacceptable.

Figure 24D:
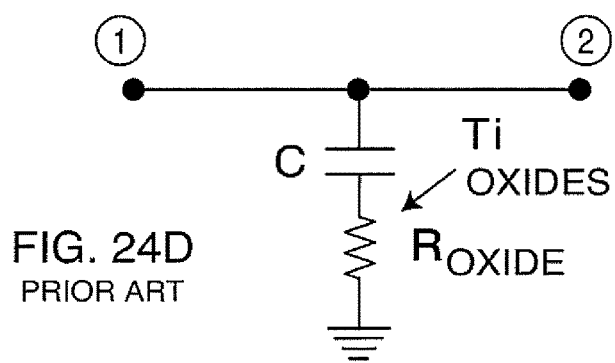
FIG. 24D is the electrical schematic of the oxide connected filter of FIG. 24 showing the undesirable $R_{OXIDE}$ in series with the filter capacitor.

FIG. 24D illustrates the schematic diagram of the filter circuit board of FIG. 24A, FIG. 24B and FIG. 24C. Undesirably, $R_{OXIDE}$ forms, which can either be immediate, latent or induced by thermal processes. As previously described, the formation of this $R_{OXIDE}$ seriously degrades EMI filter performance.

Figure 26:
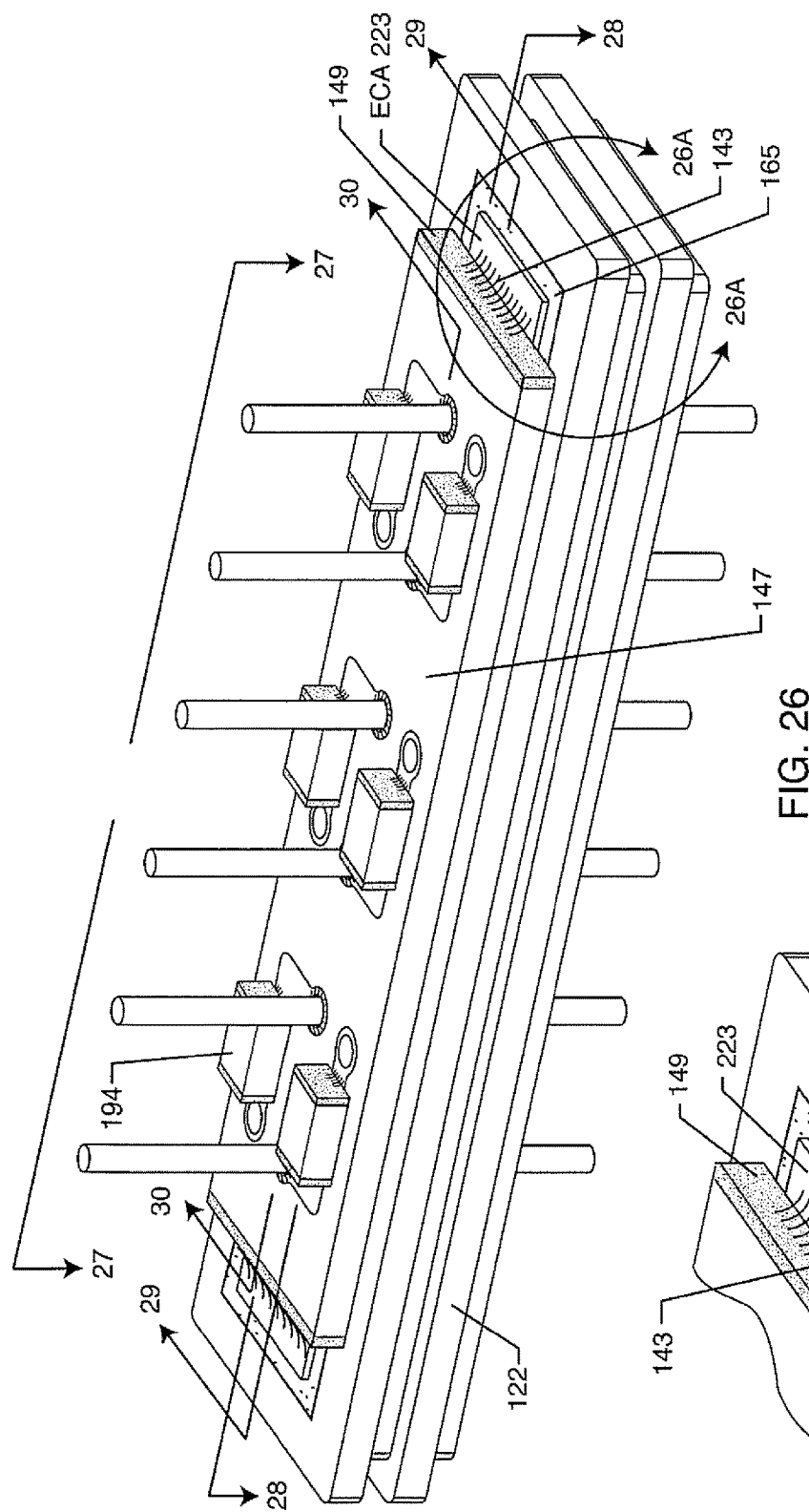
FIG. 26 illustrates an MLCC filtered circuit board with ground attachments to a ferrule ECA stripe and an oxide-resistant sputter layer.
Figure 26A:
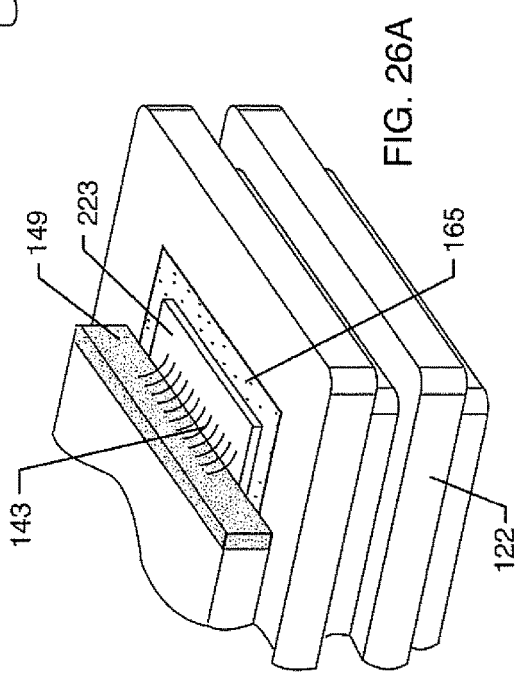
FIG. 26A is taken from section 26A-26A from FIG. 26 showing the oxide-resistant connection.

Referring to FIGS. 25 and 26+, the inventors have conceived a novel concept by which the ECA stripe 223 can be effective. To render the ECA stripe 223 effective, a low resistance and low impedance connection at high frequencies to the ferrule 122 must be made. To achieve such a low resistance and low impedance connection, especially for high frequencies, two very important steps are required: Step 1) at least the ferrule 122 device side surface must be cleaned of all oxides; and Step 2) an oxide-resistant layer 165, as shown in FIGS. 25A and 26A, must be disposed on the ferrule 122 device side surface at least in the area of the ECA stripe 223. As described previously, cleaning of the ferrule 122 device side surface can be done mechanically or chemically by either abrasive grit blasting, such as by alumina blasting, mechanical grinding, sanding processes, hydrofluoric acid cleaning, or combinations thereof, which would remove oxide layers from the ferrule 122, or at least the ferrule device side surface. Once the ferrule 122, and in particular, its device side top surface have been essentially cleaned of oxides, time and temperature become important. If the cleaned ferrule is left lying around at room temperatures, or worse yet, exposed to elevated temperatures, intentionally or unintentionally, these oxides 164 will undesirably re-form. Accordingly, the inventors have tested and determined that an oxide-resistant layer 165, such as a noble metal layer, must be deposited soon after at least the ferrule 122 device side surface is cleaned of surface oxides. One preferred method of depositing an oxide-resistant layer 165 on the ferrule 122 device side surface includes sputtering, including sputtering of such materials as gold, platinum, rhodium, or palladium. As will be seen below, there are many ways of depositing the oxide-resistant layer 165. It should also be pointed out that the term ECA or electrically conductive adhesive stripe 223 is also not meant to be eliminated. There are many other materials, as will be described herein, that can be used in addition to electrically conductive adhesives or ECA stripes. As previously described, the ferrule 122 device side surface must be cleaned of all surface oxides immediately prior to deposition of the oxide-resistant layer 165. Preferably, sputtering, and other processes to deposit layer 165, is performed in a vacuum chamber. This also includes first depositing an optional barrier layer between oxide-resistant layer 165 and the ferrule device side surface 122. Other ways of disposing an oxide-resistant layer is by physical vapor deposition, chemical vapor deposition, electrostatic spray assisted vapor deposition (ESAVD), electron beam physical vapor deposition (EBPVD), ion plating, ion beam assisted deposition (IBAD), magnetron sputtering, pulsed laser deposition, sputter deposition, vacuum deposition, pulsed electron deposition (PED), plating, electroless plating, electroplating, spraying, painting, plasma spraying, thermal spraying, spin coating, dip coating, metal foil lamination, and thin film deposited layers, either fully or selectively disposed. The electrically conductive coating may comprise one or more layers. These processes may be used to deposit materials such as gold, gold alloys, rhodium, rhodium alloys, platinum, platinum alloys, platinum-iridium alloys, palladium, palladium alloys, nitinol, cobalt-chromium alloys and combinations thereof. Additionally, selective electro-plating can be used. For example, a layer of nickel (example, see FIG. 31 element 166) would first be deposited on top of the essentially oxide-free titanium surface at least in the area of where the ECA stripe 223 is intended to be deposited on the ferrule surface device side 26'. Then, an oxide-resistant layer 165, such as a layer of gold, platinum, rhodium, or any of the materials disclosed above, is plated on top of an optional nickel layer. The purpose of the nickel layer is to prevent titanium from migrating through an oxide-resistant layer. For example, a thin film pure gold layer is highly resistant to forming oxides and is highly conductive. However, a thin film gold layer may be relatively "porous", which can allow titanium to migrate through the thin film gold layer to its free (top) surface. Researchers have shown that, when a thin film gold layer is disposed on an essentially oxide-free titanium surface, the titanium can diffuse along the grain boundaries at the gold/titanium interface to the free surface of the thin film gold layer, where the titanium is oxidized. Accordingly, laying down a layer of nickel or other suitable material that prevents migration of titanium through it, is required. In another embodiment, the nickel layer can be omitted with a suitably thick layer of gold, platinum or the like, such that they sustain surface oxide resistance.

FIG. 25 is a conventional externally grounded feedthrough capacitor 124 similar to the feedthrough capacitor 124 previously described in FIG. 3, FIG. 4 and FIG. 7. In this case, this is an inline 8-polar (octapolar) feedthrough capacitor. Ground electrical connections 143 are made to an ECA stripe 223 which overlays an oxide-resistant sputter layer 165 of the present invention. The ECA stripe 223, which overlays the oxide-resistant sputter layer 165 can be discrete pads or be continuous along both long sides of the feedthrough capacitor or all around its full perimeter. The inventors have found through analysis and testing, that the ECA stripes 223 can be discontinuous, as illustrated, and still provide excellent high frequency EMI filter performance.

Oxide-resistant sputter layers 165 enable very low resistance and time-stable electrical connections, which, in turn, provide very low equivalent series resistance (ESR) electrical connections. Oxide-resistant time-stable electrical connections are very important for medical devices, particularly AIMDs, as the inventors have discovered that, without oxide-resistant time-stable electrical connections, highly reactive materials, such as titanium, can oxidize over time, which can cause latent dangerous and unpredictable AIMD EMI filter performance issues. More importantly, EMI filter failure resultant from oxide 164 build-up over time can be life-threatening. It has been shown in numerous articles that EMI can disrupt the proper operation of an AIMD. For example, if an EMI filter fails to filter in a cardiac pacemaker, the EMI can then enter the housing of the pacemaker within which the therapy delivery circuitry resides. EMI inside the pacemaker can lead to improper therapy or even complete inhibition of therapy to the patient. Inhibition of therapy from a cardiac pacemaker to a pacemaker dependent patient can be immediately life-threatening to that patient. While a titanium oxide layer on the highly reactive titanium metal surface imparts good corrosion behavior and high biocompatibility, which is why titanium is used so extensively in medical implantable devices. However, the titanium oxide layer 164 that forms so readily on the titanium metal can and does negatively impact AIMD EMI filter performance, the negative impact being particularly observable at higher frequency applications, such as switching applications, coupling applications, bypass applications in addition to EMI filtering.

The term "oxide-resistant" is defined herein as the ability of a substance to maintain its original material properties after being exposed to oxygen; a resistance to oxidation under extreme conditions such as high temperature, essentially resists reaction with oxygen or oxygen-containing environments. The oxide-resistant sputter layer of the present invention comprises an oxide-resistant material 165 such as gold, platinum, palladium, silver, iridium, rhenium, rhodium, tantalum, tungsten, niobium, zirconium, vanadium, and combinations or alloys thereof. Some exemplary platinum-based oxide-resistant alloys for use in the oxide-resistant sputter layers 165 of the present application include: platinum-rhodium, platinum-iridium, platinum-palladium, or platinum-gold. Naturally occurring oxide-resistant alloys examples include: platiniridium (platinum-iridium), iridosmium and osmiridium (iridium-osmium). Other oxide-resistant sputter layer alloys include: gold-based, platinum-based, palladium-based, silver-based, among others, wherein the metal-based element is the largest weight percent (>50%) of the total alloying elements of the alloy. Non-limiting noble metal-based oxide-resistant alloys for use in the oxide-resistant sputter layers of the present application include: gold-palladium, gold-boron, and palladium-silver. It is anticipated that proprietary oxide-resistant alloys such as but not limited to the Pallabraze product family (palladium-containing) and Orobraze product family (gold-containing) offered by Johnson Matthey may additionally be used to form oxide-resistant layers of the present application.

FIG. 25A is taken from section 25A-25A from FIG. 25 and illustrates in cross-section, the ECA stripe 223 that overlays the relatively thin oxide-resistant sputter layer 165. In order for the sputter layer 165 to make an oxide-free electrical connection to the titanium ferrule 122, the titanium ferrule 122 must be either mechanically cleaned by grinding, abrasive grit blasting or even by chemical processes to make sure it is completely free of all oxides. Prior application of the oxide-resistant sputter layer 165, an optimal embodiment of the present invention, is to lay down a barrier layers 166 (FIG. 31), which can comprise a very thin layer of nickel, palladium or even platinum. This prevents titanium oxides from coming to the surface, for example, if the oxide-resistant sputter layer 165 is gold. Other barrier layer options instead of or in combination with nickel, palladium, and platinum include: rhodium, ruthenium, molybdenum, and chromium; alloys, such as nickel-vanadium, nichrome, nickel-iron, palladium-cobalt, cobalt-tantalum; nickel alloys, palladium alloys, platinum alloys; and electrically conductive nitrides, such as titanium nitride, zirconium nitride, hafnium nitride, vanadium nitride, tantalum nitride, molybdenum nitride, and tungsten nitride. The term "sputter layer 165" is herein defined as a thin film or coating that covers a surface or surfaces of a component, an assembly, a substrate, a structure or an object. A sputter layer 165 may comprise a single material or may alternately comprise multiple materials. It is understood that a sputter layer may comprise one or more layers. Sputter layers 165 may be applied by one of the following methods: physical vapor deposition, chemical vapor deposition, electrostatic spray assisted vapor deposition (ESAVD), electron beam physical vapor deposition (EBPVD), ion plating, ion beam assisted deposition (MAN, magnetron sputtering, pulsed laser deposition, sputter deposition, vacuum deposition, pulsed electron deposition (PED), plating, electroless plating, electroplating, spraying, painting, plasma spraying, thermal spraying, spin coating, dip coating, metal foil lamination, and thin film deposited layers. Thin sputter layers 165 for oxide-resistant attachments benefit from thin film sputter layer "stackup" systems that inhibit metal and/or oxide migration through the oxide-resistant layer, as such oxide migration through the oxide-resistant layers can eventually result in brittle connections for metal migrations and/or increased electrical connection resistance for oxide migrations. Both are undesirable, as either one independently or in combination comprise the reliability and integrity of the electrical and mechanical connections. Barrier layers provide the following benefits to AIMD component mechanical and electrical connections: (1) prevents inter-diffusion of metals up or down through the sputter layer stackup system which can compromise mechanical connection integrity; and, (2) prevents migration of oxides up or down through the sputter layer stackup system, which can compromise electrical integrity. As an example, when an essentially pure gold metal is used as the oxide-resistant sputter layer, a preferred sputter layer stackup system comprises one or more barrier layers atop of which the gold sputter layer 165 is applied. Then the ECA stripe 223 can be applied thereon providing a reliable mechanical and low resistance low ESI electrical connection. A barrier layer 166 (FIG. 31) having a thickness of 100 Angstroms to 4000 Angstroms (0.01 micron to 0.4 microns; 10 nm to 400 nm), depending on the metal selected, is sufficient to provide robust mechanical and reliable electrical connection. In some cases, the barrier layer may comprise two or more layers, each layer having a preferred thickness to achieve an overall barrier layer stackup thickness of about 100 Angstroms to about 4000 Angstroms (0.01 micron to 0.4 microns; 10 nm to 400 nm).

A barrier layer 166 (FIG. 31) is an optional consideration for oxide-resistant sputter layers 165 applied to a titanium surface. Deciding to include a barrier layer is dependent on the stability of titanium in contact with the oxide-resistant sputter layer. Using a gold oxide-resistant sputter layer on a titanium surface as an example, it is known that at elevated temperatures, titanium (Ti) can interdiffuse with the gold (Au) to either form a Ti—Au intermetallic, or, the titanium can actually diffuse to the free surface of the gold to form titanium oxides, which in turn can cause undesired ohmic resistance. In general, interdiffusion of thin films occur by way of lattice defects in the atomic structure of a material, for example, vacancies, dislocations and grain boundaries. For the Ti—Au system, titanium atoms diffuse into the gold typically in the grain boundaries, thereby either forming intermetallics, such as $TiAu_4$, $TiAu_2$, TiAu, and $Ti_3Au$, or diffusing up to the gold free surface to react with oxygen thereby forming both anatase and rutile titanium dioxide $TiO_2$. Of significance is that Ti diffusion to the Au free surface can occur at processing temperatures as low as 200° C. to 400° C. Because surface oxidation of titanium occurs at the gold free surface, the titanium oxidation reaction itself creates a chemical potential sink, which continually drives diffusion of the titanium through the gold, thereby supporting and enhancing a continuous titanium oxidation process. Since oxygen enhances diffusion of the Ti—Au system, the very rapid diffusion of the titanium through the gold layer and the formation and thickening of the titanium oxide at the free surface explains the undesirable increase in ohmic resistance over time.

Referring once again to the Ti—Au system, providing a barrier layer 166 between the titanium 102 and 122 and the gold can prevent titanium migration to the free surface of the gold layer 165. The barrier layer 166 must, however, be stable at typical AIMD processing conditions and the barrier layer 166 must effectively suppress titanium diffusion. As an example, a palladium (Pd) barrier layer 166 between the titanium surface and the gold can sufficiently suppress titanium diffusion. Researchers have shown that, even after annealing Ti—Pd—Au test samples in air, no diffusion of titanium is evident in this three-layer system. The suppression of titanium diffusion is likely due to a rapid grain boundary diffusion of gold in the palladium grain boundaries, which are thereby effectively blocked by gold, hence, this particular Pd—Au interaction therein completely suppresses any substantial migration and diffusion of the titanium. Thus, the optional barrier layer 166 provides an effective alternative for sustaining sputter layer 165 oxide-resistance, as such barrier layers 166 can effectively suppress titanium diffusion to and subsequent oxidation at a free (top) metal surface 165.

As illustrated in FIG. 25A, once the thin sputter layer has been deposited 165, then an ECA stripe 223 is applied. The ECA stripe, as defined herein, may comprise one of: a thermal-setting electrically conductive adhesive, an electrically conductive polymer, an electrically conductive epoxy, an electrically conductive silicone, an electrically conductive polyimides, or an electrically conductive polyimide, such as those manufactured by Ablestick Corporation. An oxide-free electrical connection 143 is then formed between the ECA stripe 223 and the ground metallization 132 of the feedthrough capacitor. Electrical connection material 143 may comprise a solder or a second thermal-setting conductive adhesive. In an embodiment, the thermal-setting conductive material for the ECA stripe 223 can be the same material as the electrical connection material 143. The ECA stripe 223 of the present invention provides a robust connection therefore, allowing the relatively expensive sputter material 165 to be relatively thin. For example, it would not be possible to solder directly to very thin sputter layer 165 as the sputter layer would simply dissolve into the molten solder. For a thermal-setting conductive polyimide, it is also difficult to make a mechanically robust connection to such a thin layer 165 without first depositing an ECA 223 stripe over it. By depositing the ECA stripe over the sputter layer 165 and then curing it, without the feedthrough capacitor, one minimizes strains and stresses due to mismatches in coefficients of thermal expansion. Accordingly, adding the electrical connection 143 in a subsequent operation becomes very reliable and easy to accomplish. The feedthrough capacitor 124 is generally disposed against the insulator 122 with an optional insulative washer 206, as shown in FIG. 25A.

Referring once again to FIG. 25A, it is understood that both the sputter layer 165 and the ECA stripe 223 are proud of the surface of the ferrule 122. This is in marked contrast to the gold pocket-pads 250 as taught in U.S. Pat. No. 10,350,421. One is referred to the gold pocket-pad 250 of FIG. 23F herein. To form the gold pocket-pad, as described in U.S. Pat. No. 10,350,421, the contents of which are incorporated herein fully by reference, one must first form a recess or pocket in the ferrule itself. This swimming pool-like structure is formed or machined into the ferrule. The gold pocket-pad of the U.S. Pat. No. 10,350,421 invention requires that a gold braze (or equivalent) preform be disposed into the pocket-pad, and reflowed. Reflow of a gold braze preform is normally performed in a high temperature gold braze furnace. Forming of the pocket-pad is a relatively expensive process and also the amount of gold 250 that is required to form a robust pocket-pad, is also substantial and expensive. In the present invention, there is no need for a recessed pocket or swimming pool-type structure in the ferrule 122 at all. Instead, a sputter layer 165 is disposed proud or on the top of the ferrule, over which the ECA stripe 223 is formed.

FIG. 26 is a filter circuit board 147 with one or more embedded circuit board ground plates that is similar to FIG. 24. However, referring to FIG. 26, one can see that in accordance with the present invention, disposed on top of the ferrule, is oxide-resistant sputter layer 165 with the ECA stripe 223 of the present invention disposed on top. There is an electrical connection using electrical connection material 143 formed between the ECA stripe and the ground edge metallization 149 of circuit board 147.

FIG. 26A is taken from section 26A-26A from FIG. 26 and shows a blow-up view of the electrical connection 143 between the circuit board ground termination 149 and the ECA stripe 223 which rests on top of the oxide-resistant sputter layer 165.

Figure 27:
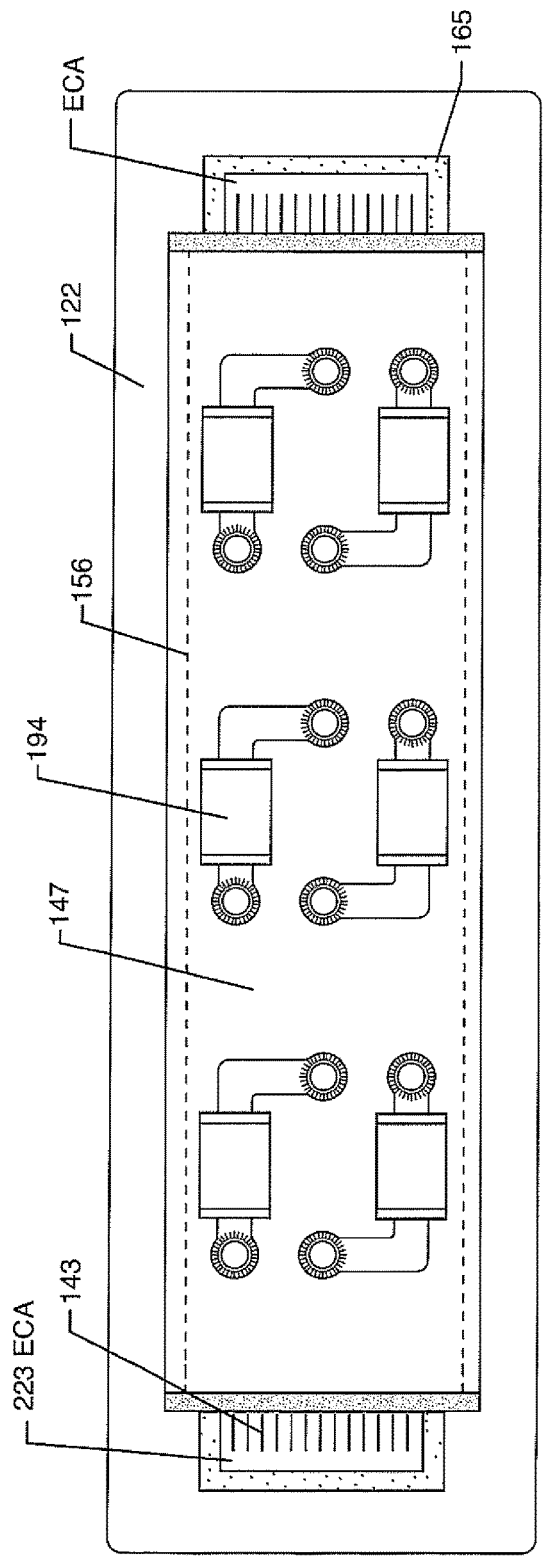
FIG. 27 is taken from section 27-27 from FIG. 26 showing the top view of the circuit board.

FIG. 27 is taken from section 27-27 from FIG. 26 and shows the top view of the circuit board of FIG. 26. One can see the top view of the ECA stripe 223, the electrical connection material 143 and the oxide-resistant sputter layer 165. The hidden lines 156 illustrated in FIG. 27, show the edge of at least one embedded circuit board ground shield plate.

Figure 28:
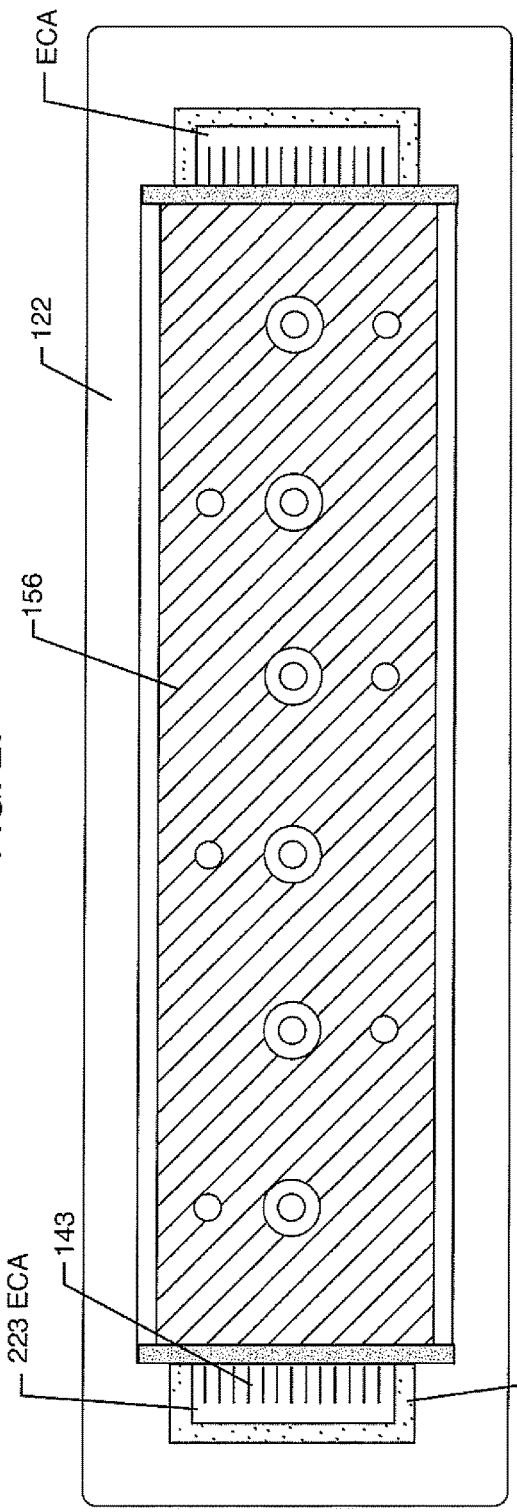
FIG. 28 is taken from section 28-28 from FIG. 26 showing at least one circuit board ground plate.

FIG. 28 is taken from section 28-28 from FIG. 26 and in this cutaway, shows the circuit board ground plate 156. It is appreciated that there is at least one of these ground plates, but there may be a multiplicity of these ground plates 156, including embedded ground plates or one external ground plate disposed between circuit board 147 and ferrule 122. Importantly, the ground plate 156 is disposed over the hermetic seal insulator 120 thereby blocking direct penetration of EMI into the interior of the AIMD housing 102. As described, one or more ground plates 156 effectively shield and provide a low impedance path to decouple dangerous EMI signals to the system ground 144. The circuit board ground plates of the present invention are also known as ground shield plates.

Figure 29:
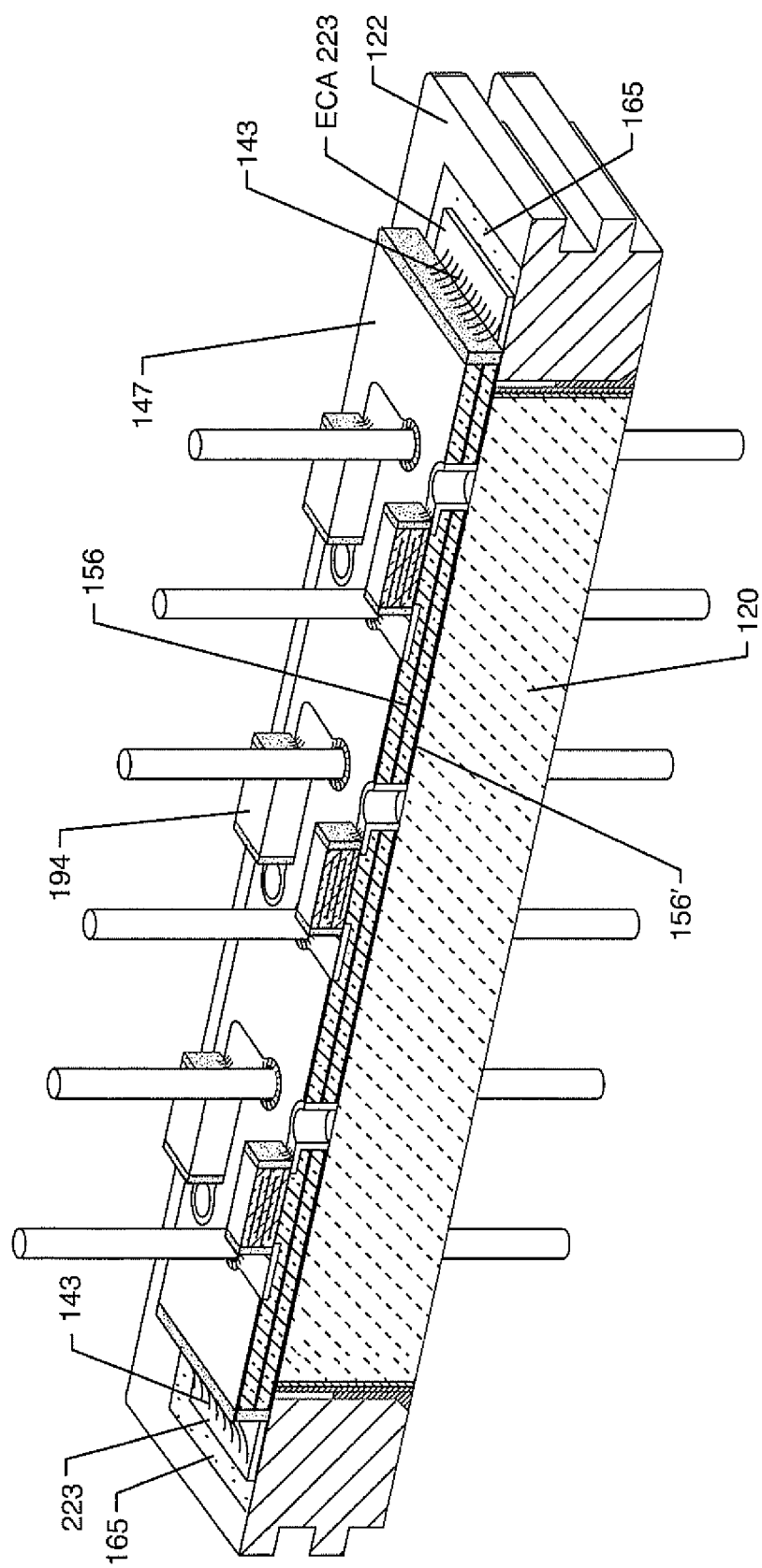
FIG. 29 is a sectional view taken from section 29-29 from FIG. 26 through the center line of circuit board ground vias.

FIG. 29 is taken from section 29-29 from FIG. 26 and illustrates a cut through the first row of MLCC chip capacitors. Referring once again to FIG. 29, one can see that there is an embedded ground shield plate 156 and an external ground shield plate 156' which is disposed between the bottom of the circuit board 147 and the top of the insulator 120. The external ground shield plate 156 is ideal since this space is as close to the insulator 120 as possible. This prevents waveguide action wherein radiated EMI can couple or radiate through the edge of the circuit board 147.

Figure 30:
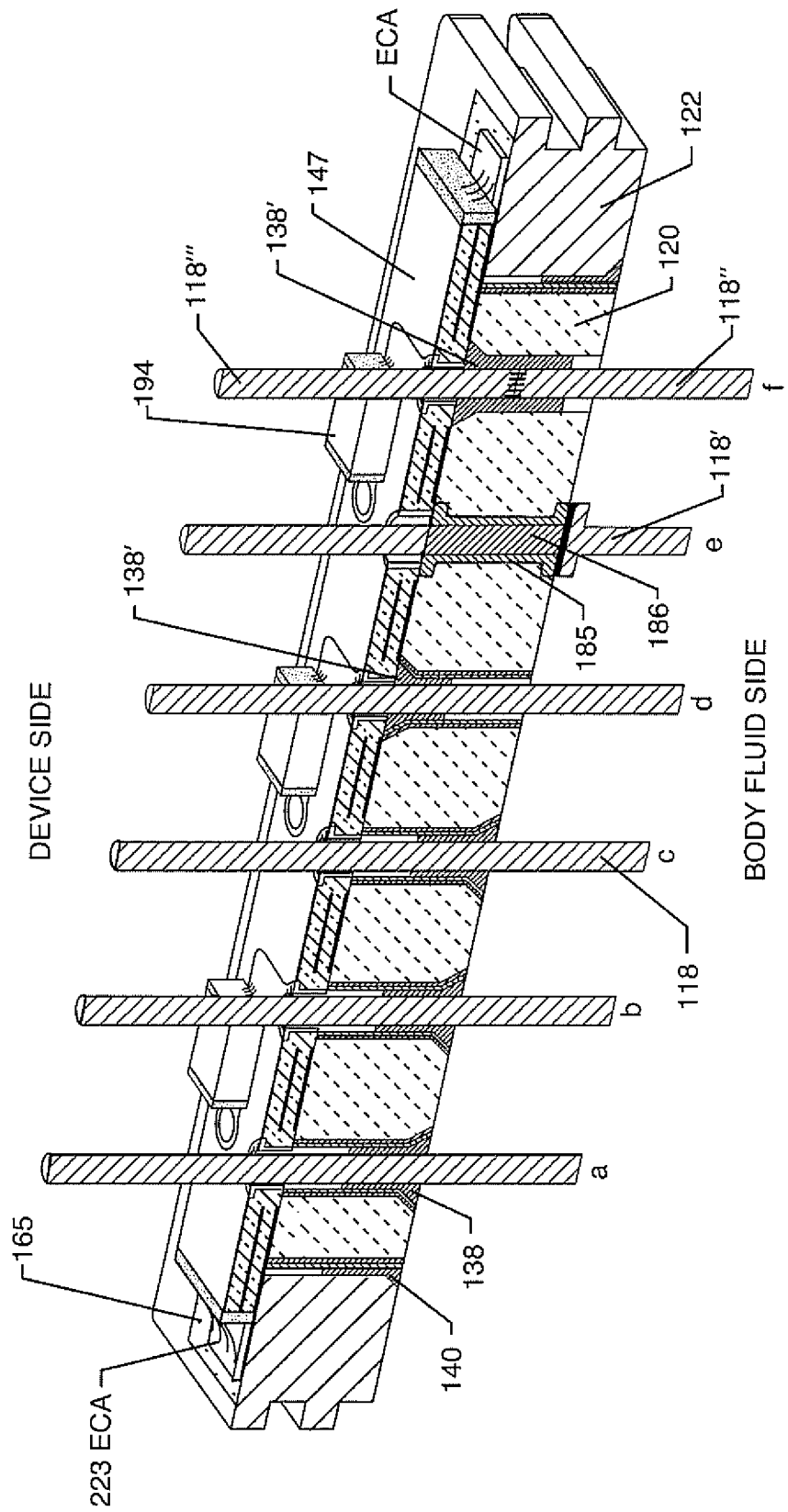
FIG. 30 is taken from section 30-30 from FIG. 26 showing a sectional view through the active pins.

FIG. 30 is taken from section 30-30 from FIG. 26 and illustrates a cutaway right through the center of the active terminal pins of the AIMD circuit board 147. Leadwires or pins a, b and c have conventional gold brazes that hermetically seal the pins to the hermetically sealed insulator 120. As can be seen, the circuit board 147 and its associated MLCC chip capacitors 194 are oriented towards the device side of the AIMD. Gold brazes associated with pins a, b and c, are disposed on the body fluid side. Pin d is very similar to the gold brazes 138 for a, b and c, which are disposed on the body fluid side. On pin d, the gold braze 138' is disposed toward the device side. There is an advantage in disposing the gold braze 138' on the device side. That is, if pin d is a heavily oxidized pin, such as a niobium or tantalum pin, then a direct electrical connection can be made from the circuit board via associated with gold braze 138' such that an oxide-free electrical connection is made between gold braze 138', leadwire d and the MLCC chip capacitor ground termination. This is very important as it allows the use of very low-cost terminal pins. Terminal pin e embodies the terminal pin post 118' disposed on a co-sintered via. In this case, the co-sintered vias are taught by U.S. Pat. No. 10,249,415, the contents of which are herein incorporated fully be reference. One is referred to FIG. 131 of the '415 patent for various embodiments of co-sintered vias. Referring once again to FIG. 30, there is a substantially pure platinum center core 186, which is surrounded by ceramic reinforced metal composite (CRMC). Referring once again to FIG. 30, terminal pin f is a 2-part pin as taught by U.S. Pat. No. 10,272,251, the contents of which are incorporated herein fully by reference. Pin f allows a relatively inexpensive tantalum, niobium or titanium pin 118" to be disposed on the body fluid side, which is then co-brazed 138', such that a shorter palladium or platinum iridium pin 118''' is disposed toward the device side. These are thoroughly taught in the '251 patent. Another advantage of the construct in pin f is that the gold braze 138' is disposed towards the device side. This has the same advantage as that previously described for pin d that would allow an oxide-resistant connection direct to the gold braze 138'. Referring once again to FIG. 30 pin e, one will also appreciate that materials 185 and 186 can be combined in substantially pure platinum 186 as taught in U.S. Pat. No. 8,653,384 and its entire family. These are substantially pure platinum co-sintered vias with alumina insulators 120.

Figure 31:
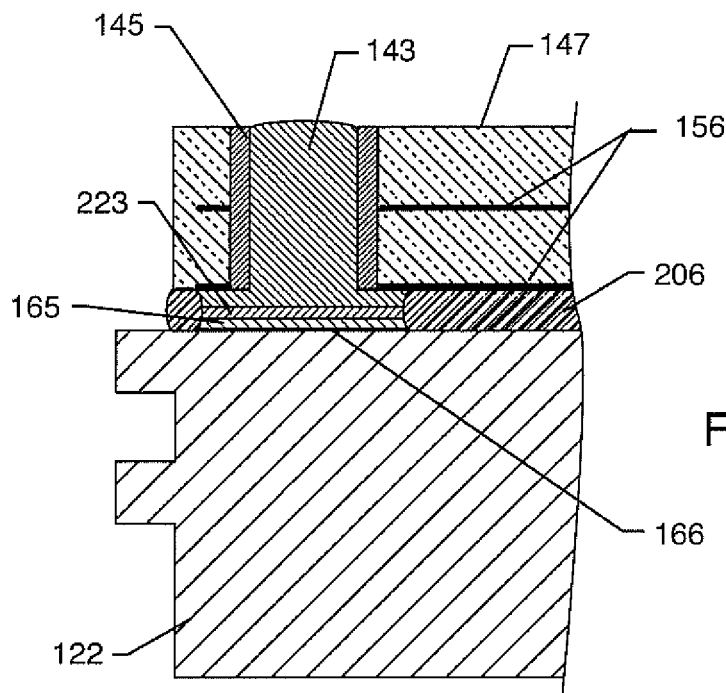
FIG. 31 illustrates an alternative method of oxide resistive attachment of the circuit board of FIG. 26 to an ECA stripe.

FIG. 31 is similar to FIG. 23H, except that the gold pocket-pad 250 has been replaced by the ECA layer 223 and the oxide-resistant sputter layer 165 of the present invention. In this case, circuit board 147 has a spatially aligned via hole that connects to its internal ground electrode plates 156. This via hole 143 replaces an edge connection to the circuit board. It is appreciated that any number of ground via holes can be used in this manner with corresponding ECA stripes 223 and the oxide-resistant sputter layers 165. Referring once again to FIG. 31, one can see that there is an optional barrier layer 166 that is represented by a thin black line between the oxide-resistant sputter layer 165 and the ferrule 122. As previously described, this optional barrier layer can comprise of nickel or the like to block any oxides of titanium from coming to the surface.

Referring back to FIG. 31, it is appreciated that the electrical connection material 143 can be a solid nail head structure. This is a machined or stamped pin or an eyelet. In the case that this was a solid material, there is an electrical connection between this solid construct 143 and the via hole metallization 145 (not shown). Referring once again to FIG. 31, it is appreciated that spatially aligning a grounded via hole over the ECA stripe 223 and the oxide-resistant sputter layer 165 of the present invention, is equally applicable to internally grounded feedthrough capacitors 124'.

Figure 32:
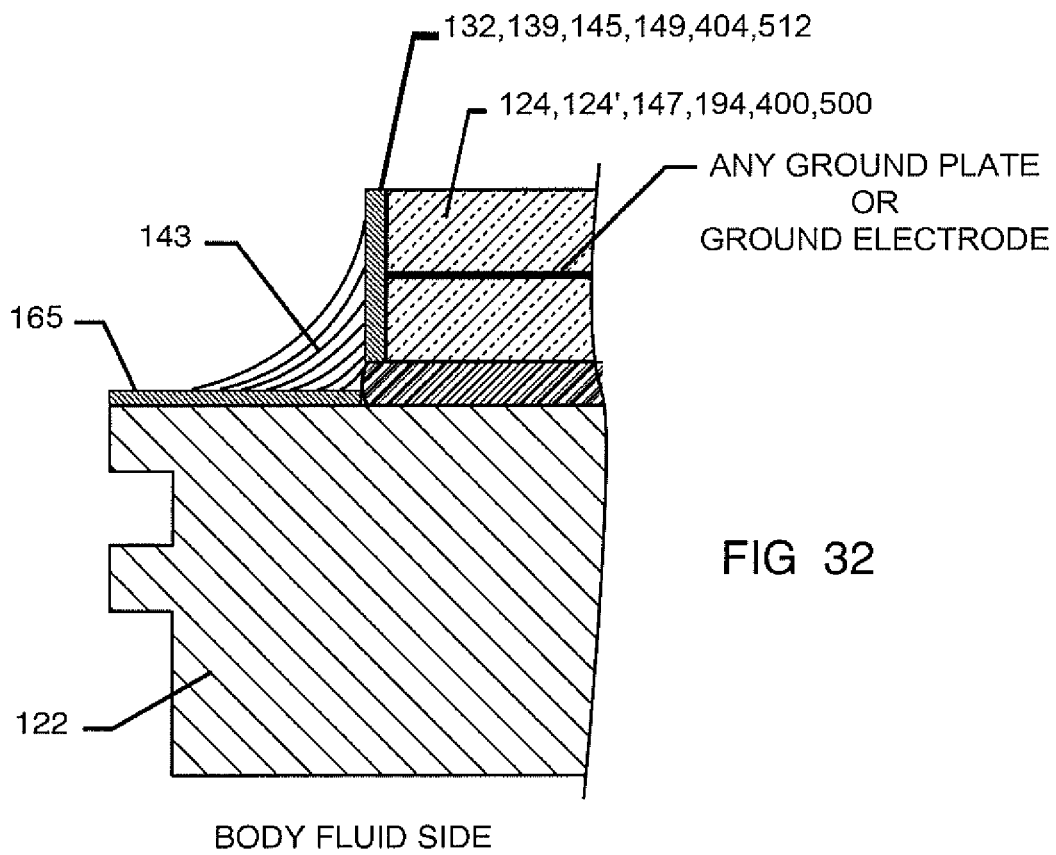
FIG. 32 is similar to FIG. 31 showing an alternative attachment using a circuit board via hole.

FIG. 32 indicates an embodiment of the present invention wherein the oxide-resistant sputter layer 165 is sufficiently robust that it can provide an oxide-free electrical connection without the need for an overlaying ECA stripe 223. In this case, the ferrule 122 is thoroughly cleaned, and then for example, a barrier layer of nickel, and then an oxide-resistant sputter layer of gold 165 can be applied. This gold layer would have to be substantially thick so that a subsequent attachment of an electrical connection material 143 would not damage the connection. For example, if electrical connection material 143 was a high lead content solder, then a gold sputter layer 165 would readily dissolve into the molten solder. Platinum, palladium and alloys thereof can be used as barrier layers for gold, so that is molten solder does dissolve in the gold, an oxide-resistant attachment to the titanium is preserved. Alternatively, platinum, palladium and alloys thereof provide an excellent alternative to gold layers altogether, as these materials prevent both metal diffusion and migration, thus, titanium would not be able to reach the free metal surface, and then oxidize. Additionally, platinum, palladium and alloys thereof are also solderable. Thus, while preserving oxide-free electrical connection integrity, platinum, palladium and alloys thereof additionally prevent solder leaching of a eutectic or a soldered component, therein also preserving the mechanical integrity of the attachment. Moreover, neither palladium nor platinum themselves form oxides or migrate easily.

Oxide-resistant sputter layers 165 may also be used to enable solderability of titanium. In this case, an oxide-resistant solderable material in accordance with the present invention is disposed on a cleaned titanium surface. Examples of oxide-resistant solderable materials that can be disposed on titanium include gold, palladium, platinum, rhodium, and combinations and alloys thereof.

Referring once again to FIG. 32, one will see that the ground termination can be for a feedthrough capacitor, an internally grounded feedthrough capacitor 124', an MLCC chip capacitor 194, a flat-thru capacitor 400 or an X2Y attenuator 500. It is very important that all of these EMI filters have a system ground connection 143 that is free of oxides. The ground plate in FIG. 32 is any ground plate or ground electrode or any of the filters above described. Accordingly, the termination material that connects between the oxide-resistant sputter layer 165 and the filter capacitor can be a connection either to a feedthrough capacitor outside diameter perimeter metallization 132, a grounding pedestal or location for an internally grounded feedthrough capacitor 132, the ground terminations for a flat-thru capacitor, the ground terminations for an X2Y attenuator, an ground edge metallization 149 for any type of filter circuit board 147, or a metallization or termination on the inside diameter of any circuit board or capacitive via hole 145.

Referring to the ECA stripe 514 of FIG. it is contemplated that, for some applications wherein ECA electrical connection may not be needed to provide an electrical connection between at least two AIMD components, the ECA stripe 514 can be eliminated if the oxide-resistant layer(s) 516 is/are robust enough to prevent titanium migration and oxidation, thereby allowing attachment of the electrical connection material 504 directly to the oxide-resistant layer 516. As previously disclosed, platinum, palladium and alloys thereof are two such oxide-resistant layer material options. In other words, either an oxide-resistant layer can be used to make the ECA stripe 514 an effective low resistance and low impedance connection or the oxide-resistant layer(s) alone can be used instead of the ECA stripe 514. It is appreciated that the ECA stripe 514 and/or the metallization layer 516 may also be used to provide suitable grounding, not just for circuit boards 106, 106', but also for all types of filter capacitors, including feedthrough filters 24, 24', hybrid feedthrough capacitors 24", MLCC chip capacitors 154, X2Y attenuators 300, and flat-thru capacitors 400.

Referring once again to FIG. 32, it is appreciated that direct attachment of the ground electrical material 143 to a robust oxide-resistant sputter layer 165 is equally applicable to the ground via hole of feedthrough capacitors 124 or internally grounded feedthrough capacitors 124', circuit board 147 edge, ground or via hole metallizations, MLCC chip capacitor 194 ground metallization, or the ground metallization of flat-thru capacitors 400 or X2Y attenuators 500. Accordingly, the ground plate in FIG. 32 can be any ground plate or ground electrode of any of the capacitors or filter circuit boards of the present invention.

Figure 33:
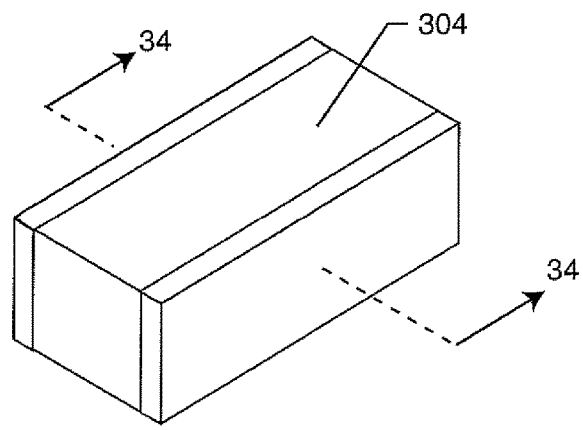
FIG. 33 is a pictorial view of a prior art reverse geometry MLCC chip capacitor.

FIG. 33 illustrates a prior art reverse geometry MLCC chip capacitor 304.

Figure 34:
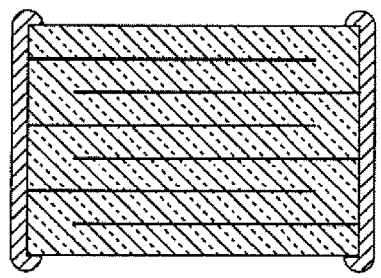
FIG. 34 is a sectional view taken from section 34-34 from FIG. 33.

FIG. 34 is taken from section 34-34 from FIG. 33 showing the internal electrode plates of the reverse geometry MLCC chip capacitor 304. The advantage of the reverse geometry MLCC chip capacitor is greatly reduced inductance and superior high frequency filtering performance.

Figure 35:
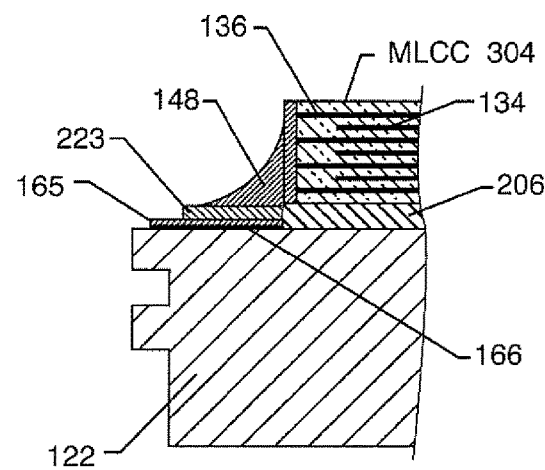
FIG. 35 is a sectional view illustrating the reverse geometry MLCC chip capacitor attached to an ECA stripe of the present invention.

FIG. 35 shows the reverse geometry MLCC chip capacitor 304 mounted to ferrule 122 using the novel ECA stripe 223 and the oxide-resistant sputter layer 165 of the present invention.

Figure 36:
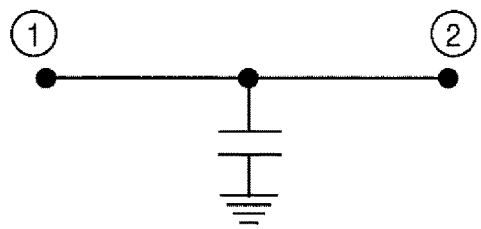
FIG. 36 illustrates the electrical schematic diagram of the filter capacitor reverse geometry MLCC chip capacitor of FIG. 33.

FIG. 36 is the schematic diagram of the reverse geometry MLCC chip capacitor 304. Notably, no resistance or inductance is present in this schematic as this configuration offers superior high frequency filter performance at a very low impedance, Z.

Figure 37:
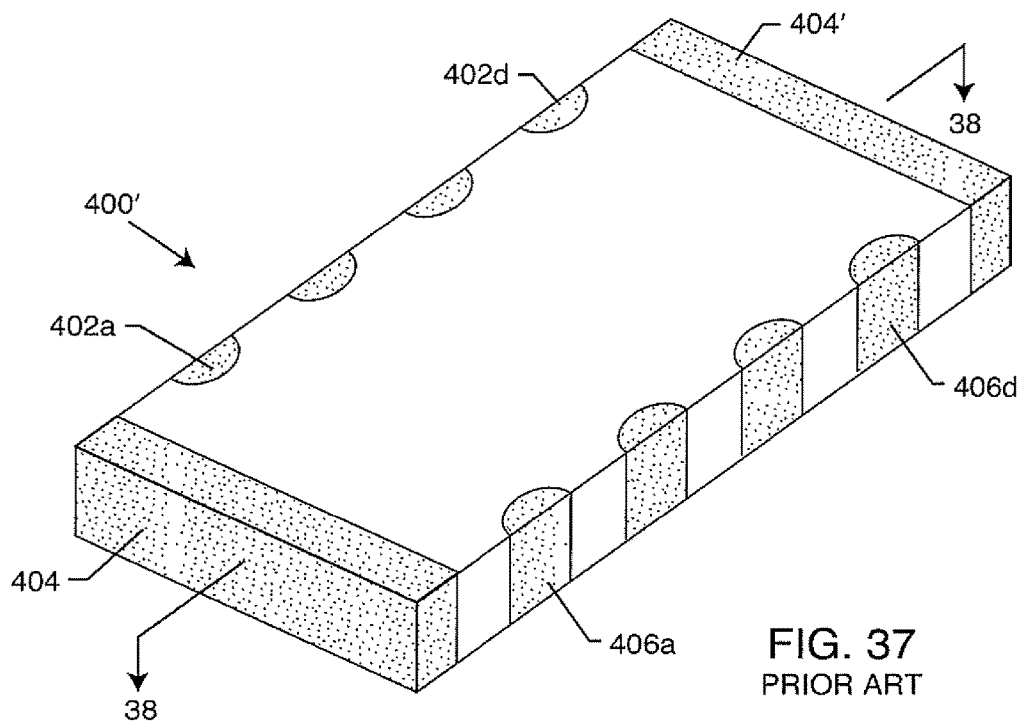
FIG. 37 illustrates a prior art quadpolar flat-thru filter capacitor.

FIG. 37 is a prior art quadpolar flat-thru capacitor 400'. It has four active terminations 402, 406 and two ground terminations 404, 404'.

Figure 38:
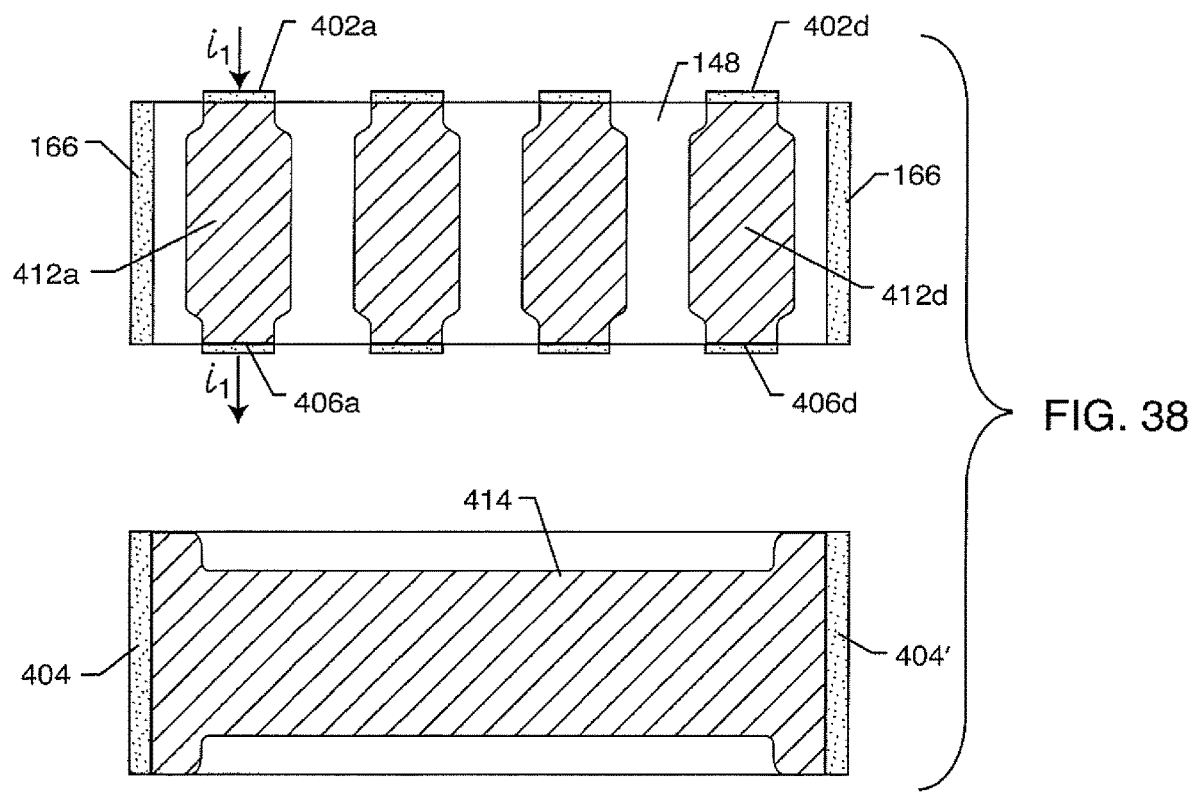
FIG. 38 are internal section taken from section 38-38 from FIG. 37 showing the flat-thru active and ground electrode plates.

FIG. 38 is taken from section 38-38 from FIG. 37 and illustrates the active electrodes 412a through 412d. Also shown in the lower part of FIG. 38, are the set of ground electrodes 414. These are connected to terminations on the left side 404 and on the right side 404'.

Figure 39:
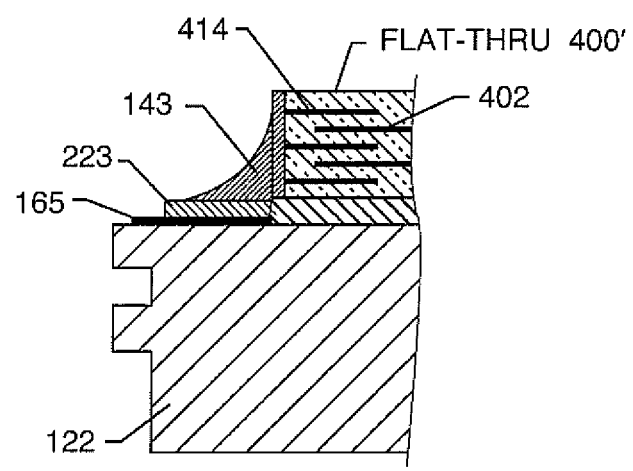
FIG. 39 is a sectional view of the flat-thru capacitor of FIG. 37 with a ground attachment to the ECA stripe of the present invention.

FIG. 39 shows the quadpolar flat-thru capacitor 400' of FIG. 37 attached to ferrule 122. Attachment material 143 connects to the ECA stripe 123 and in turn, to the oxide-resistant sputter layer 165. The electrical attachment material is connected to the flat-thru capacitor edge metallization 404 as indicated. Flat-thru capacitor ground electrode plates 414 are also indicated.

Figure 39A:
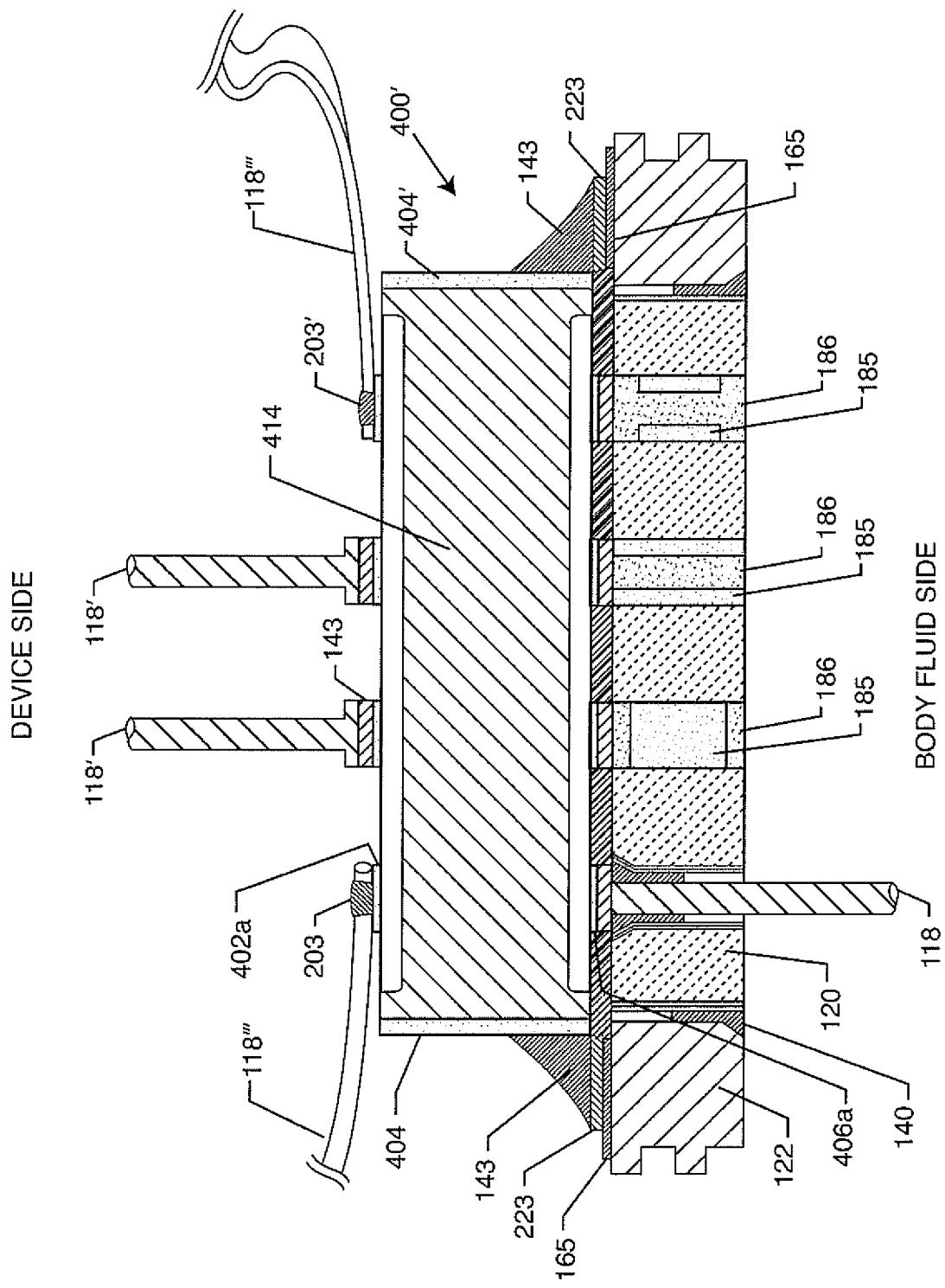
FIG. 39A illustrates the flat-thru capacitor of FIG. 37 mounted in a tombstone position to ECA stripes disposed on a hermetic seal ferrule.

FIG. 39A shows the flat-thru capacitor 400' of FIG. 37 mounted in a tombstone position to an insulator and ferrule for an AIMD hermetic terminal assembly. One can see in this unique construct that the flat-thru capacitor ground terminations 404 are electrically connected 143 to the ECA layer 223 and the oxide-resistant sputter layer 165 of the present invention. Referring once again to FIG. 39A, one can see various types of co-sintered vias that include a CRMC material and a pure platinum material 186.

Figure 39B:
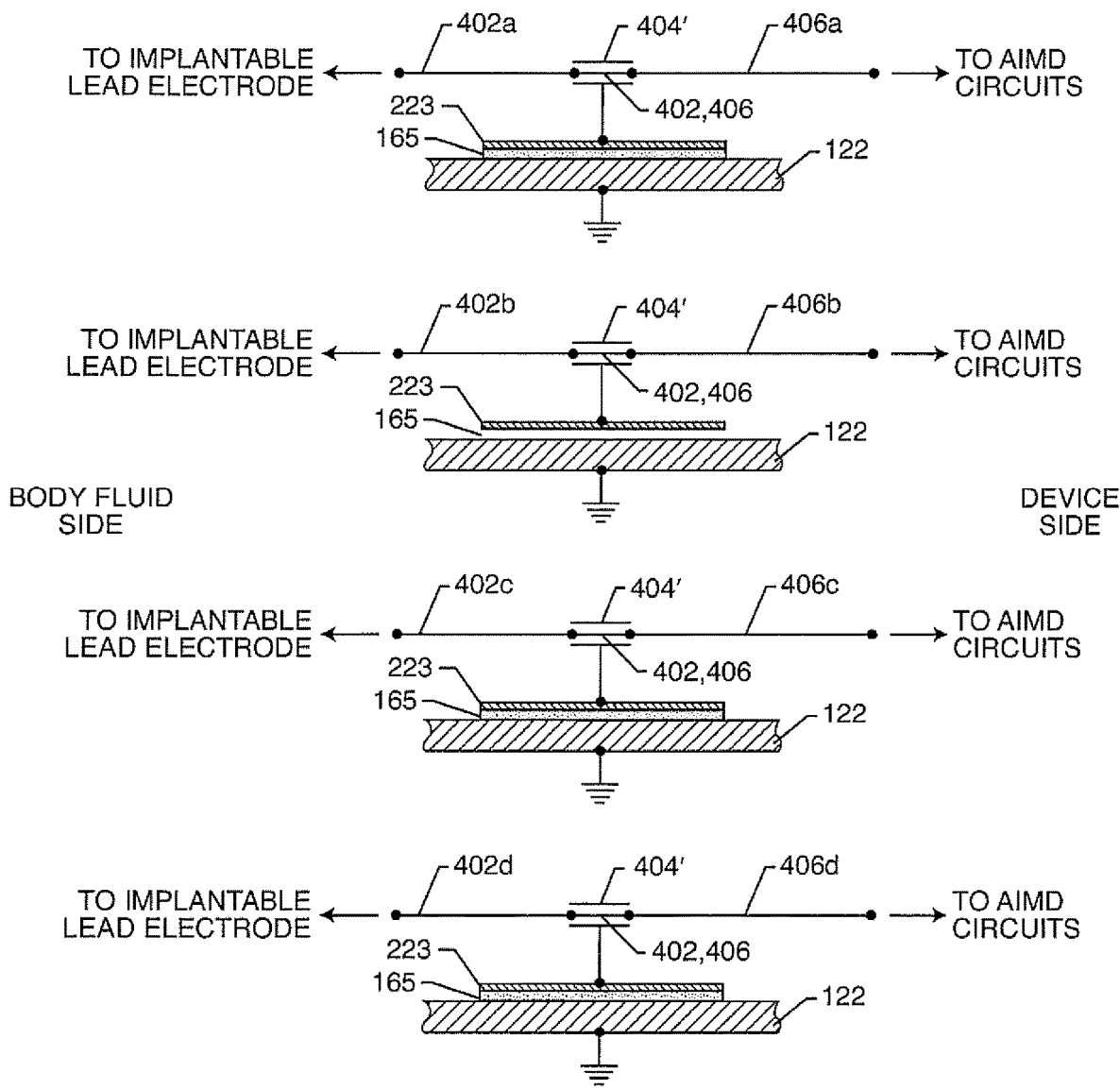
FIG. 39B illustrates the schematic of the flat-thru filter capacitor of FIGS. 37 and 39A.

FIG. 39B illustrates the schematic diagram of the flat-thru capacitor of FIGS. 37 and 39. Referring once again to FIG. 39A, one can see that the flat-thru capacitor ground is connected to the ECA stripe and, in turn, to the oxide-resistant sputter layer 165 and then to ferrule 122.

Figure 40:
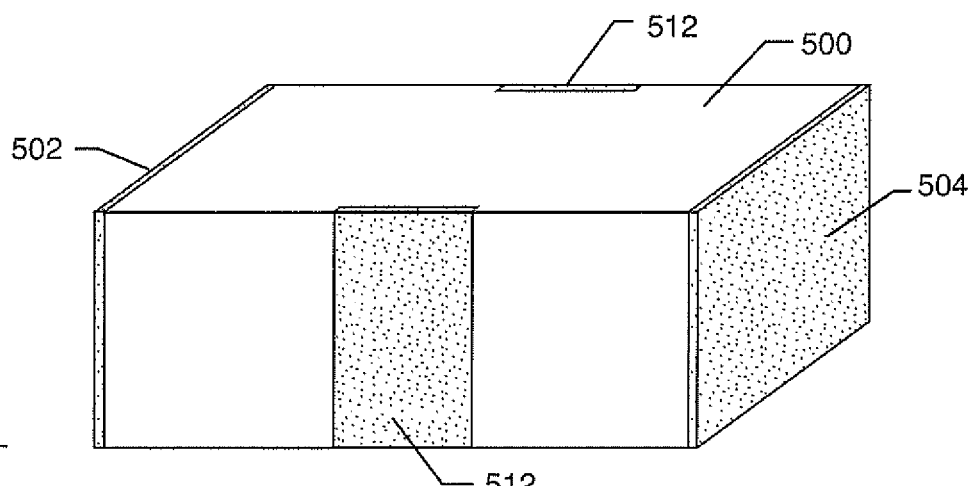
FIG. 40 is a pictorial view of a prior art X2Y attenuator.

FIG. 40 illustrates a prior art X2Y attenuator 500. As indicated, it has active metallizations 502 and 504 and ground metallizations 512.

Figure 40A:
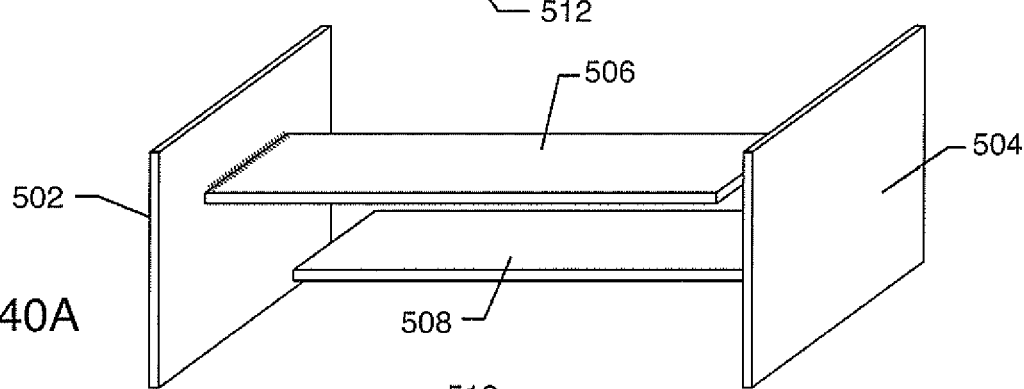
FIG. 40A is an exploded section showing the active electrode plates of the X2Y attenuator of FIG. 40.

FIG. 40A illustrates the two active electrode plates 506 and 508 of the X2Y attenuator. Terminations 502 and 504 connect to the active plates 506 and 508.

Figure 40B:
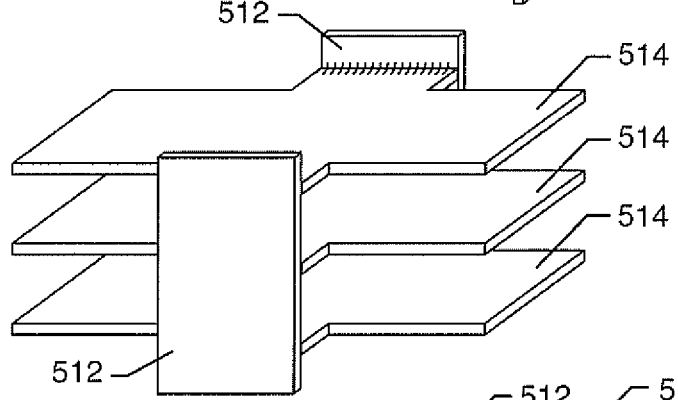
FIG. 40B is an exploded view showing the ground electrode plates of the X2Y attenuator of FIG. 40.

FIG. 40B illustrates the X2Y attenuator ground electrode plate set 514. These ground electrode plates are connected to ground terminations 512, as shown.

Figure 40C:
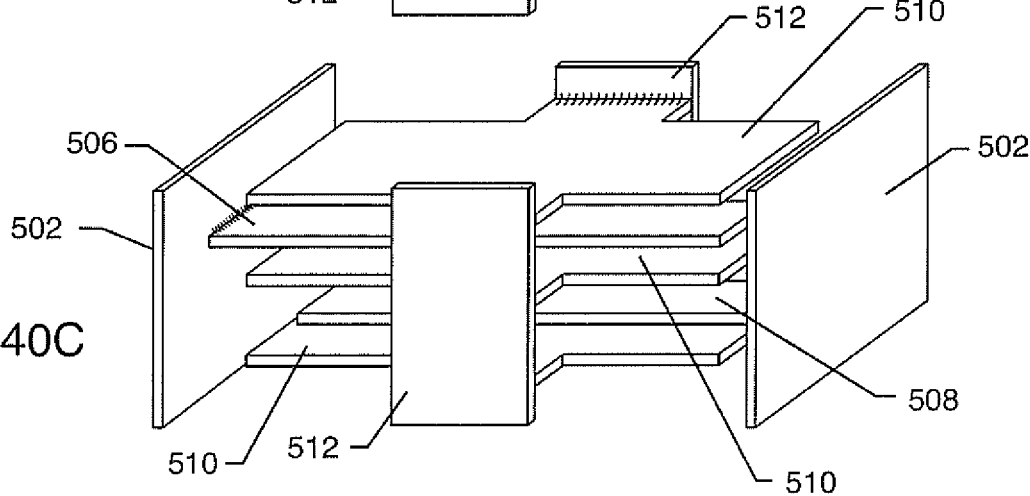
FIG. 40C is an exploded view showing how the ground and active electrode plates are interleaved for the X2Y attenuator of FIG. 40.

FIG. 40C illustrates the entire X2Y attenuator with the ground electrode plates 510 interleaved with the active electrode plates 506 and 508.

Figure 40D:
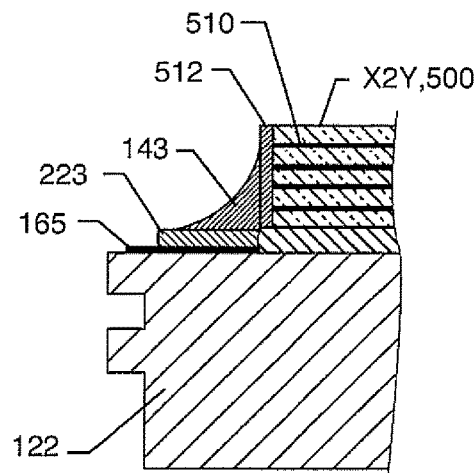
FIG. 40D illustrates the X2Y attenuator of FIG. 40 with a ground connection to the ECA stripe of the present invention.

FIG. 40D is a sectional view of the X2Y attenuator 500 of FIG. 40 attached to ferrule 122. As can be seen, the ground metallization 512 is electrically connected 143 to the ECA stripe 223 and, in turn, to the oxide-resistant sputter layer 165 of the present invention. Referring once again to FIG. 40D, one can see that the ground termination 512 connects to the X2Y attenuator ground plates 510.

Figure 40E:
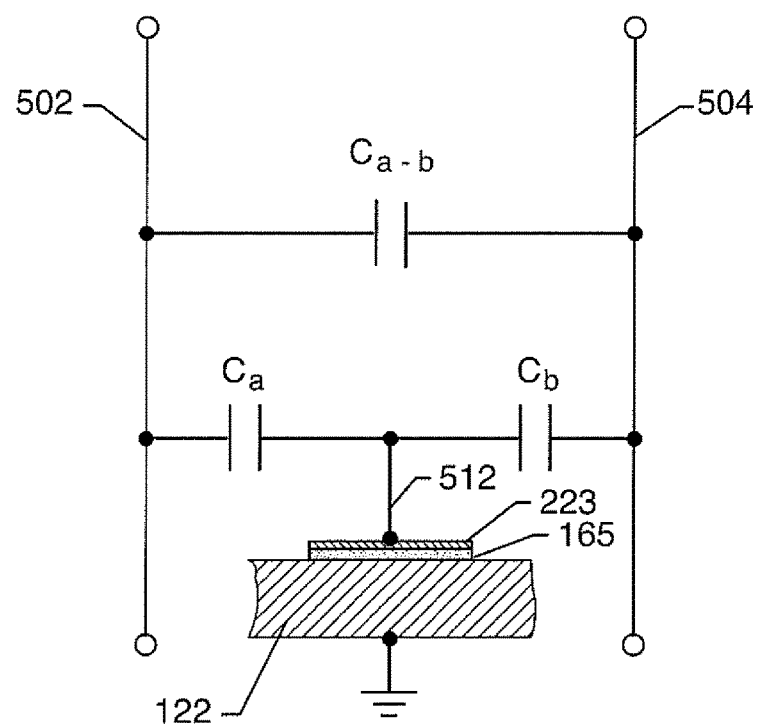
FIG. 40E illustrates the schematic diagram for the X2Y attenuator of FIG. 40D.

FIG. 40E illustrates the schematic diagram of the X2Y attenuator 500 of FIGS. 40 and 40D. Importantly, the ground electrical connection 512 is to the ECA stripe 223 and the oxide-resistant sputter layer 165 and to ferrule 122. This is the same as a system ground 144 electrical connection 123 (3). In general, all of the filter components of the present invention are disposed on the device side of the hermetic seal insulator ferrule to protect said components from body fluid.

Figure 41:
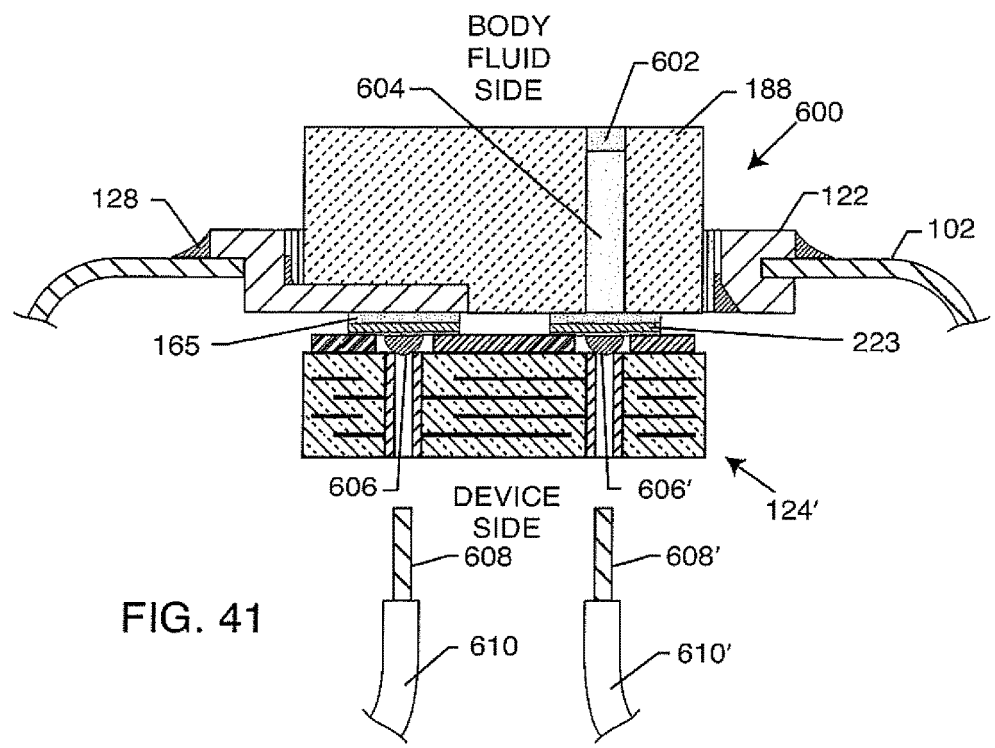
FIG. 41 illustrates internally grounded feedthrough capacitor attached to an ECSA stripe on a ferrule peninsula.

FIG. 41 illustrates a ceramic body or insulator 188 that has been gold brazed to ferrule 122. On the left-hand side of FIG. 41, there is a peninsula structure, which is very similar to the ground peninsula structure taught in FIGS. 13A, 13B and 13C. Instead of the leadwires taught in FIGS. 13A, 13B and 13C, the peninsula provides a ground for an internally grounded feedthrough capacitor 124'. The internally grounded feedthrough capacitor ground electrode plates are connected to the left-hand feedthrough capacitor via hole through electrical connection 606 to the ECA stripe 223 and the oxide-resistant sputter layer 165 of the present invention. This provides the system ground 144 for the internally grounded feedthrough capacitor. Internally grounded feedthrough capacitors are taught by U.S. Pat. No. 5,905,627, the contents of which are incorporated herein fully by reference. Referring now again to FIG. 41, one can see that the active via on the right-hand side is a co-sintered conductive via consisting of conductive material 602 and 604. In one embodiment, the end cap 602 is of substantially pure platinum and the fill 604 is of CRMC. The conductive via can also have an oxide-resistant sputter layer 165 and an ECA stripe 223 for convenient mounting of the internally grounded feedthrough capacitor through electrical connection material 606 and 606'.

Figure 42:
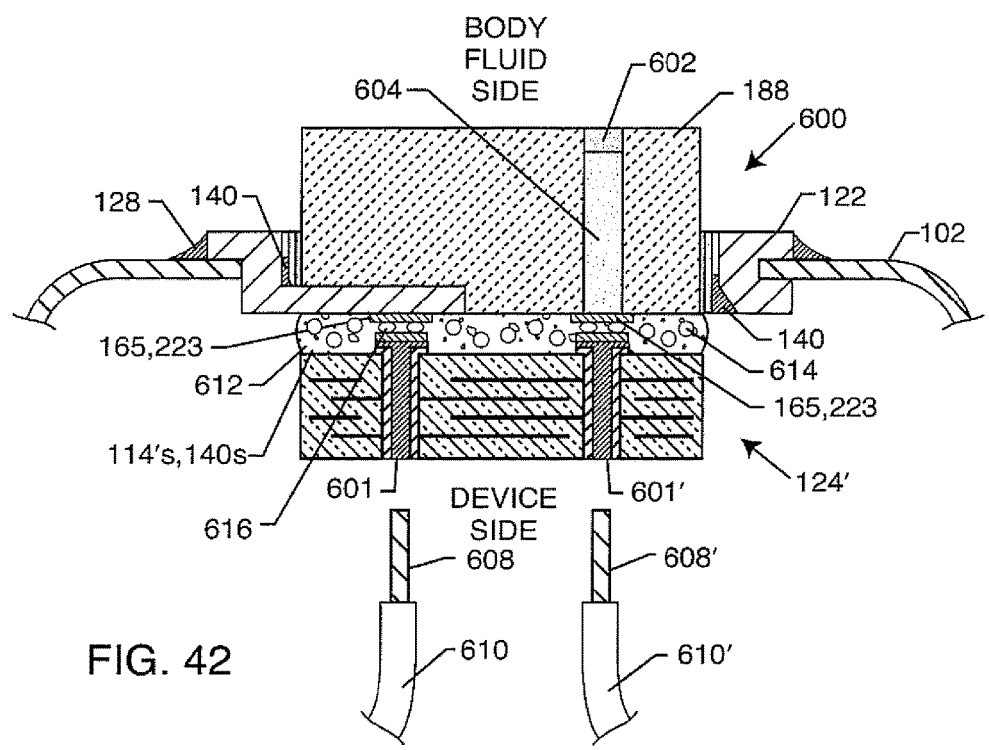
FIG. 42 is similar to FIG. 41 wherein, the electrical connection to the ECA stripe is accomplished by anisotropic conductive film.

FIG. 42 is very similar to FIG. 41, except that the internally grounded feedthrough capacitor is electrically attached to the ECA stripes using an anisotropic conductive film 612. One can see that the ECA stripes stand proud of the insulator and the ferrule to aid in compressing conductive spheres 616. In the areas where the conductive spheres are not compressed, they are not conductive 614. For simplicity, the oxide-resistant sputter layers 165 have been omitted from FIG. 42. Referring back to FIG. 42, one can see a nail headed structure is inserted or soldered or filled into the internally grounded feedthrough capacitor 124' via holes. Noble oxide-resistant sputter layer 164 alone, or in combination with the ECA stripe 223, is shown proud of a ferrule 122 bottom surface. These proud areas compress the conductive particles 616 of the ACF film 612. Therefore, electric conductivity only occurs in these areas. In general, uncompressed ACF sphere 614 do not electrically connect or only electrically connect horizontally for a very short space. ACF films are ideal in the present application, as unlike molten solder, they do not tend to dissolve the adjacent terminations. This makes the use of a relatively thick, but proud noble material 165 (without the ECA stripe 223) an ideal and low-cost alternative.

FIG. 43 provides further detail regarding embodiments and materials that can be used in any of the embodiments of the present application. Included within this table are patents assigned to the present Applicant regarding EMI filter capacitor, EMI filter circuit boards, and hermetic co-sintered feedthroughs, all of which benefit from the low ESR low inductance oxide-resistant attachment of the present application. The contents of the patents listed in this table are herein incorporated fully by this reference.

What is claimed is:

1. A feedthrough, comprising:
   a) a ferrule, comprising:
      i) a ferrule opening extending to a ferrule first side opposite a ferrule second side;
      ii) a gold layer overlaying at least a portion of the ferrule second side; and
      iii) an electrically conductive adhesive (ECA) overlaying and directly contacted to the gold layer;
   b) an insulator hermetically sealed to the ferrule in the ferrule opening, the insulator extending to an insulator first side at or adjacent to the ferrule first side and an insulator second side at or adjacent to the ferrule second side;
   c) at least one via hole extending through the insulator to the insulator first and second sides;
   d) an electrically conductive pathway disposed in and hermetically sealed to the insulator in the at least one via hole; and
   e) a gold braze hermetically sealing the insulator to the ferrule.

2. The feedthrough of claim 1, wherein the ferrule is of titanium.

3. The feedthrough of claim 1, wherein the electrically conductive adhesive (ECA) is selected from a thermal-setting electrically conductive adhesive, an electrically conductive polymer, an electrically conductive epoxy, an electrically conductive silicone, an electrically conductive polyimide, a thermal-setting electrically conductive polyimide, and mixtures thereof.

4. The feedthrough of claim 1, further comprising a barrier layer selected from palladium, platinum and titanium-nitride directly contacting at least a portion of the ferrule second side, and wherein the gold layer directly contacts the barrier layer.

5. The feedthrough of claim 1, wherein the gold layer has a thickness ranging from 10 nm to 400 nm.

6. The feedthrough of claim 1, wherein the electrically conductive pathway hermetically sealed to the insulator in the at least one via hole is selected from a lead conductor, a terminal pin, a circuit trace, and a platinum-containing sintered material.

7. A filtered feedthrough, comprising:
   a) a feedthrough, comprising:
      i) a ferrule, comprising:
         A) a ferrule opening extending to a ferrule first side opposite a ferrule second side;
         B) a gold layer overlaying at least a portion of the ferrule second side; and
         C) an electrically conductive adhesive (ECA) overlaying and directly contacted to the gold layer;
      ii) an insulator hermetically sealed to the ferrule in the ferrule opening, the insulator extending to an insulator first side at or adjacent to the ferrule first side and an insulator second side at or adjacent to the ferrule second side;
      iii) at least one via hole extending through the insulator to the insulator first and second sides;

iv) a terminal pin disposed in and hermetically sealed to the insulator in the at least one via hole, wherein at least a second side portion of the terminal pin extends outwardly beyond the insulator second side; and v) a gold braze hermetically sealing the insulator to the ferrule;

b) at least one capacitor disposed on or adjacent to the ferrule and insulator second sides, the capacitor comprising:

i) a capacitor dielectric supporting at least one active electrode plate and at least one ground electrode plate in a spaced and interleaved relationship with each other;

ii) at least one active passageway extending through the capacitor dielectric, wherein a capacitor active metallization in the active passageway is electrically connected to the at least one active electrode plate, and wherein the terminal pin second side portion extends into the capacitor active passageway; and iii) a capacitor ground metallization attached to the capacitor dielectric and electrically connected to the at least one ground electrode plate;

c) an active electrical connection electrically connecting the terminal pin second side portion in the active passageway to the capacitor active metallization electrically connected to the at least one active electrode plate; and d) a ground electrical connection electrically connecting the capacitor ground metallization to the ECA directly contacting the gold layer overlaying at least a portion of the ferrule device side.

8. The filtered feedthrough of claim 7, wherein the ferrule is of titanium.

9. The filtered feedthrough of claim 7, wherein the electrically conductive adhesive (ECA) is selected from a thermal-setting electrically conductive adhesive, an electrically conductive polymer, an electrically conductive epoxy, an electrically conductive silicone, an electrically conductive polyimide, a thermal-setting electrically conductive polyimide, and mixtures thereof.

10. The filtered feedthrough of claim 7, further comprising a barrier layer contacting at least a portion of the ferrule second side, and wherein the gold layer directly contacts the barrier layer.

11. The filtered feedthrough of claim 10, wherein the barrier layer is selected from palladium, platinum and titanium-nitride, nickel, rhodium, ruthenium, molybdenum, chromium, nickel-vanadium, nichrome, nickel-iron, palladium-cobalt, cobalt-tantalum, zirconium nitride, hafnium nitride, vanadium nitride, tantalum nitride, molybdenum nitride, tungsten nitride, and mixtures thereof.

12. The filtered feedthrough of claim 7, wherein the at least one capacitor is selected from a three-terminal device feedthrough capacitor, a multilayer ceramic chip capacitor, a monolithic ceramic capacitor, a flat-thru capacitor, and an X2Y attenuator.

13. The filtered feedthrough of claim 7, further comprising an insulative washer disposed between the insulator hermetically sealed to the ferrule and the at least one capacitor.

14. A filtered feedthrough that is configured for attachment to a housing for an active implantable medical device (AIMD), the filtered feedthrough comprising:

a) a feedthrough, comprising:

i) a ferrule, comprising:

A) a ferrule opening extending to a ferrule body fluid side opposite a ferrule device side;

B) a gold layer overlaying at least a portion of the ferrule device side; and

C) an electrically conductive adhesive (ECA) overlaying and directly contacting the gold layer; and ii) an insulator hermetically sealed to the ferrule in the ferrule opening, the insulator extending to an insulator body fluid side at or adjacent to the ferrule body fluid side and an insulator device side at or adjacent to the ferrule device side, wherein, when the ferrule hermetically sealed to the insulator is attached to an opening in a housing of an AIMD, the ferrule and insulator body fluid sides, and the ferrule and insulator device sides reside outside and inside the AIMD, respectively;

iii) at least one via hole extending through the insulator to the insulator body fluid and device sides;

iv) a terminal pin disposed in and hermetically sealed to the insulator in the at least one via hole, wherein at least a device side portion of the terminal pin extends outwardly beyond the insulator device side; and v) a gold braze hermetically sealing the insulator to the ferrule;

b) at least one capacitor disposed on or adjacent to the ferrule and insulator device sides, the capacitor comprising:

i) a capacitor dielectric supporting at least one active electrode plate and at least one ground electrode plate in a spaced and interleaved relationship with each other;

ii) at least one active passageway extending through the capacitor dielectric, wherein a capacitor active metallization in the active passageway is electrically connected to the at least one active electrode plate, and wherein the terminal pin device side portion extends into the capacitor active passageway; and iii) a capacitor ground metallization attached to the capacitor dielectric and electrically connected to the at least one ground electrode plate;

c) an active electrical connection electrically connecting the terminal pin device side portion in the active passageway to the capacitor active metallization electrically connected to the at least one active electrode plate; and d) a ground electrical connection electrically connecting the capacitor ground metallization to the ECA directly contacting the gold layer overlaying at least a portion of the ferrule device side.

15. The filtered feedthrough of claim 14, wherein the ferrule is of titanium.

16. The filtered feedthrough of claim 14, wherein the electrically conductive adhesive (ECA) is selected from a thermal-setting electrically conductive adhesive, an electrically conductive polymer, an electrically conductive epoxy, an electrically conductive silicone, an electrically conductive polyimide, a thermal-setting electrically conductive polyimide, and mixtures thereof.

17. The filtered feedthrough of claim 14, further comprising a barrier layer directly contacting at least a portion of the ferrule device side, and wherein the gold layer directly contacts the barrier layer.

18. The filtered feedthrough of claim 7, wherein the barrier layer is selected from palladium, platinum and titanium-nitride, nickel, rhodium, ruthenium, molybdenum, chromium, nickel-vanadium, nichrome, nickel-iron, palladium-cobalt, cobalt-tantalum, zirconium nitride, hafnium nitride, vanadium nitride, tantalum nitride, molybdenum nitride, tungsten nitride, and mixtures thereof.

19. The filtered feedthrough of claim 14, wherein the at least one capacitor is selected from a three-terminal device feedthrough capacitor, a multilayer ceramic chip capacitor, a monolithic ceramic capacitor, a flat-thru capacitor, and an X2Y attenuator.

20. The filtered feedthrough of claim 14, further comprising an insulative washer disposed between the insulator hermetically sealed to the ferrule and the at least one capacitor.

* * * * *